(12) United States Patent
Aljuri et al.

(10) Patent No.: US 12,582,297 B2
(45) Date of Patent: Mar. 24, 2026

(54) ELONGATE TREATMENT PROBE FOR ROBOTIC SURGERY

(71) Applicant: PROCEPT BioRobotics Corporation, Redwood City, CA (US)

(72) Inventors: Nikolai Aljuri, Hillsborough, CA (US); Surag Mantri, East Palo Alto, CA (US); Peter Bentley, Reno, NV (US); Luis Baez, Mountain View, CA (US); James Luis Badia, Redwood City, CA (US)

(73) Assignee: PROCEPT BioRobotics Corporation, Redwood City, CA (US)

( * ) Notice: Subject to any disclaimer, the term of this patent is extended or adjusted under 35 U.S.C. 154(b) by 755 days.

(21) Appl. No.: 17/303,287

(22) Filed: May 26, 2021

(65) Prior Publication Data

US 2021/0282868 A1     Sep. 16, 2021

Related U.S. Application Data

(63) Continuation of application No. 15/446,853, filed on Mar. 1, 2017, now Pat. No. 11,406,453, which is a
(Continued)

(51) Int. Cl.
   *A61B 18/04*        (2006.01)
   *A61B 1/00*         (2006.01)
   (Continued)

(52) U.S. Cl.
   CPC .......... *A61B 5/055* (2013.01); *A61B 1/00045* (2013.01); *A61B 1/00087* (2013.01);
   (Continued)

(58) Field of Classification Search
   CPC ......... A61B 18/14; A61B 34/20; A61B 34/25; A61B 34/30; A61B 2034/2048; A61B 2034/2059; A61B 2034/252
   See application file for complete search history.

(56) References Cited

U.S. PATENT DOCUMENTS 3,818,913 A     6/1974   Wallach
3,821,510 A     6/1974   Muncheryan
                (Continued)

FOREIGN PATENT DOCUMENTS

CN     1511007 A     7/2004
CN     1861010 A     11/2006
                (Continued)

OTHER PUBLICATIONS

Botto et al., "Electrovaporization of the Prostate with the Gyrus Device," J. Endourol. (Apr. 2001) 15(3):313-316.
(Continued)

*Primary Examiner* — Daniel W Fowler
(74) *Attorney, Agent, or Firm* — Knobbe, Martens, Olson & Bear, LLP

(57)              ABSTRACT

A surgical treatment apparatus comprises an elongate support, an elongate tube, and a movable endoscope having a stiff distal portion, in which the stiff distal portion of the endoscope is configured to move one or more components of the apparatus when the support remains substantially fixed. The support may comprise a plurality of spaced apart aspiration openings near the distal end in order to facilitate alignment with the treatment site. In many embodiments, an image guided treatment apparatus is configured for use with an imaging device. In many embodiments, a target resection profile is provided. The target resection profile and one or more tissue structures are displayed on an image, and the target resection profile displayed on the image is adjusted with user input.

19 Claims, 56 Drawing Sheets

Related U.S. Application Data continuation of application No. PCT/US2015/048695, filed on Sep. 4, 2015.

(60) Provisional application No. 62/046,674, filed on Sep. 5, 2014, provisional application No. 62/046,652, filed on Sep. 5, 2014.

(51) Int. Cl.

| | |
|---|---|
| *A61B 1/005* | (2006.01) |
| *A61B 1/018* | (2006.01) |
| *A61B 5/00* | (2006.01) |
| *A61B 5/055* | (2006.01) |
| *A61B 5/06* | (2006.01) |
| *A61B 17/32* | (2006.01) |
| *A61B 17/3203* | (2006.01) |
| *A61B 18/14* | (2006.01) |
| *A61B 34/00* | (2016.01) |
| *A61B 34/20* | (2016.01) |
| *A61B 17/00* | (2006.01) |
| *A61B 17/34* | (2006.01) |
| *A61B 34/10* | (2016.01) |
| *A61B 34/30* | (2016.01) |
| *A61B 90/00* | (2016.01) |

(52) U.S. Cl.

CPC ...... *A61B 1/00135* (2013.01); *A61B 1/00137* (2013.01); *A61B 1/005* (2013.01); *A61B 1/018* (2013.01); *A61B 5/064* (2013.01); *A61B 5/7425* (2013.01); *A61B 17/320016* (2013.01); *A61B 17/3203* (2013.01); *A61B 18/14* (2013.01); *A61B 34/20* (2016.02); *A61B 34/25* (2016.02); *A61B 5/066* (2013.01); *A61B 2017/00274* (2013.01); *A61B 2017/00991* (2013.01); *A61B 2017/3409* (2013.01); *A61B 2017/345* (2013.01); *A61B 2034/107* (2016.02); *A61B 2034/2048* (2016.02); *A61B 2034/2059* (2016.02); *A61B 2034/2068* (2016.02); *A61B 2034/252* (2016.02); *A61B 34/30* (2016.02); *A61B 2090/3782* (2016.02)

(56) References Cited

U.S. PATENT DOCUMENTS

| | | | |
|---|---|---|---|
| 3,847,988 | A | 11/1974 | Gold |
| 3,875,229 | A | 4/1975 | Gold |
| 4,097,578 | A | 6/1978 | Perronnet |
| 4,220,735 | A | 9/1980 | Dieck |
| 4,239,776 | A | 12/1980 | Bayles |
| 4,377,584 | A | 3/1983 | Rasmusson |
| 4,386,080 | A | 5/1983 | Crossley |
| 4,389,071 | A | 6/1983 | Johnson, Jr. |
| 4,461,283 | A | 7/1984 | Doi |
| 4,474,251 | A | 10/1984 | Johnson, Jr. |
| 4,560,373 | A | 12/1985 | Sugino |
| 4,636,505 | A | 1/1987 | Tucker |
| 4,672,963 | A | 6/1987 | Barken |
| 4,760,071 | A | 7/1988 | Rasmusson |
| 4,776,349 | A | 10/1988 | Nashef |
| 4,913,698 | A | 4/1990 | Ito |
| 5,037,431 | A | 8/1991 | Summers |
| 5,055,100 | A * | 10/1991 | Olsen ..................... A61B 18/00 606/32 |
| 5,116,615 | A | 5/1992 | Gokcen |
| 5,135,482 | A | 8/1992 | Neracher |
| 5,207,672 | A | 5/1993 | Roth |
| 5,257,991 | A | 11/1993 | Fletcher |
| 5,267,341 | A | 11/1993 | Shearin |
| 5,269,785 | A | 12/1993 | Bonutti |
| 5,322,503 | A | 6/1994 | Desai |
| 5,322,504 | A | 6/1994 | Doherty |
| 5,413,575 | A * | 5/1995 | Haenggi ........... A61B 18/1402 606/45 |
| 5,454,782 | A | 10/1995 | Perkins |
| 5,496,267 | A | 3/1996 | Drasler |
| 5,505,729 | A | 4/1996 | Rau |
| 5,514,669 | A | 5/1996 | Selman |
| 5,527,330 | A | 6/1996 | Tovey |
| 5,558,634 | A | 9/1996 | Mitchell |
| 5,562,703 | A | 10/1996 | Desai |
| 5,620,414 | A | 4/1997 | Campbell, Jr. |
| 5,630,794 | A | 5/1997 | Lax |
| 5,649,923 | A | 7/1997 | Gregory |
| 5,672,153 | A | 9/1997 | Lax |
| 5,672,171 | A | 9/1997 | Andrus |
| 5,729,914 | A | 3/1998 | Aloisi |
| 5,741,225 | A * | 4/1998 | Lax ..................... A61B 18/1477 604/22 |
| 5,753,641 | A | 5/1998 | Gormley |
| 5,770,603 | A | 6/1998 | Gibson |
| 5,772,657 | A | 6/1998 | Hmelar |
| 5,773,791 | A | 6/1998 | Kuykendal |
| 5,782,848 | A | 7/1998 | Lennox |
| 5,785,521 | A | 7/1998 | Rizoiu |
| 5,817,649 | A | 10/1998 | Labrie |
| 5,833,701 | A | 11/1998 | Gordon |
| 5,836,941 | A | 11/1998 | Yoshihara |
| 5,861,002 | A | 1/1999 | Desai |
| 5,871,462 | A | 2/1999 | Yoder |
| 5,872,150 | A | 2/1999 | Elbrecht |
| 5,902,499 | A | 5/1999 | Richerzhagen |
| 5,957,849 | A * | 9/1999 | Munro ................... A61B 8/445 600/463 |
| 5,994,362 | A | 11/1999 | Gormley |
| 6,022,860 | A | 2/2000 | Engel |
| 6,066,130 | A | 5/2000 | Gregory |
| 6,071,284 | A | 6/2000 | Fox |
| 6,117,128 | A | 9/2000 | Gregory |
| 6,142,991 | A | 11/2000 | Schatzberger |
| 6,179,831 | B1 | 1/2001 | Bliweis |
| 6,200,573 | B1 | 3/2001 | Locke |
| 6,217,543 | B1 | 4/2001 | Anis |
| 6,217,860 | B1 | 4/2001 | Woo |
| 6,228,046 | B1 | 5/2001 | Brisken |
| 6,231,591 | B1 | 5/2001 | Desai |
| 6,254,597 | B1 | 7/2001 | Rizoiu |
| 6,285,903 | B1 | 9/2001 | Rosenthal |
| 6,296,639 | B1 | 10/2001 | Truckai |
| 6,375,365 | B1 | 4/2002 | Chau |
| 6,375,635 | B1 * | 4/2002 | Moutafis ........... A61B 17/3203 604/35 |
| 6,378,525 | B1 | 4/2002 | Beyar |
| 6,413,256 | B1 | 7/2002 | Truckai |
| 6,425,877 | B1 | 7/2002 | Edwards |
| 6,440,105 | B1 | 8/2002 | Menne |
| 6,451,017 | B1 | 9/2002 | Moutafis |
| 6,471,637 | B1 | 10/2002 | Chatenever |
| 6,565,555 | B1 | 5/2003 | Ryan |
| 6,572,578 | B1 | 6/2003 | Blanchard |
| 6,607,524 | B1 | 8/2003 | Labudde |
| 6,611,141 | B1 | 8/2003 | Schulz |
| 6,720,745 | B2 | 4/2004 | Lys |
| 6,814,731 | B2 | 11/2004 | Swanson |
| 6,821,275 | B2 | 11/2004 | Truckai |
| 6,890,332 | B2 | 5/2005 | Truckai |
| 6,953,461 | B2 | 10/2005 | Mcclurken |
| 6,960,182 | B2 | 11/2005 | Moutafis |
| 6,986,764 | B2 | 1/2006 | Davenport |
| 7,008,421 | B2 | 3/2006 | Daniel |
| 7,015,253 | B2 | 3/2006 | Escandon |
| 7,115,100 | B2 | 10/2006 | Mcrury |
| 7,122,017 | B2 | 10/2006 | Moutafis |
| 7,163,875 | B2 | 1/2007 | Richerzhagen |
| 7,326,054 | B2 | 2/2008 | Todd |
| 7,882,841 | B2 | 2/2011 | Aljuri |
| 8,092,507 | B2 | 1/2012 | Tomasello |
| 8,788,019 | B2 | 7/2014 | Downey |
| 8,795,194 | B2 | 8/2014 | Howard |
| 8,814,921 | B2 | 8/2014 | Aljuri |

(56)　　　　　　References Cited

U.S. PATENT DOCUMENTS

| 9,232,959 B2 | 1/2016 | Aljuri |
| 9,232,960 B2 | 1/2016 | Aljuri |
| 9,237,902 B2 | 1/2016 | Aljuri |
| 9,364,250 B2 | 6/2016 | Aljuri |
| 9,364,251 B2 | 6/2016 | Aljuri |
| 9,510,771 B1 | 12/2016 | Finley |
| 9,510,853 B2 | 12/2016 | Aljuri |
| 9,668,764 B2 | 6/2017 | Aljuri |
| 9,848,904 B2 | 12/2017 | Aljuri |
| 9,867,635 B2 | 1/2018 | Alvarez |
| 9,931,445 B2 | 4/2018 | Pustilnik |
| 11,406,453 B2 | 8/2022 | Aljuri |
| 2001/0002562 A1 | 6/2001 | Moutafis |
| 2001/0048942 A1 | 12/2001 | Weisman |
| 2002/0010502 A1 | 1/2002 | Trachtenberg |
| 2002/0022869 A1 | 2/2002 | Hareyama |
| 2002/0040220 A1 | 4/2002 | Zvuloni |
| 2002/0045911 A1 | 4/2002 | Fletcher |
| 2002/0087101 A1 | 7/2002 | Barrick |
| 2002/0111617 A1 | 8/2002 | Cosman |
| 2002/0128637 A1 | 9/2002 | Von Der Heide |
| 2003/0036768 A1 | 2/2003 | Hutchins |
| 2003/0060819 A1 | 3/2003 | Mcgovern |
| 2003/0065321 A1 | 4/2003 | Carmel |
| 2003/0073902 A1 | 4/2003 | Hauschild |
| 2003/0097060 A1* | 5/2003 | Yanof ..................... A61B 34/76 600/424 |
| 2003/0135205 A1 | 7/2003 | Davenport |
| 2003/0139041 A1 | 7/2003 | Leclair |
| 2003/0216722 A1 | 11/2003 | Swanson |
| 2004/0024311 A1 | 2/2004 | Quaid |
| 2004/0097829 A1 | 5/2004 | Mcrury |
| 2004/0133254 A1 | 7/2004 | Sterzer |
| 2004/0153098 A1* | 8/2004 | Chin ...................... A61B 90/11 600/374 |
| 2004/0158127 A1* | 8/2004 | Okada .................... A61B 18/14 600/104 |
| 2004/0230211 A1 | 11/2004 | Moutafis |
| 2005/0004516 A1 | 1/2005 | Vanney |
| 2005/0187537 A1* | 8/2005 | Loeb ................ A61B 17/32002 606/49 |
| 2005/0240124 A1* | 10/2005 | Mast ...................... A61N 7/022 601/2 |
| 2005/0256517 A1 | 11/2005 | Boutoussov |
| 2005/0261674 A1 | 11/2005 | Nobis |
| 2006/0030787 A1 | 2/2006 | Quay |
| 2006/0074489 A1 | 4/2006 | Bryan |
| 2006/0089626 A1 | 4/2006 | Vlegele |
| 2006/0118495 A1 | 6/2006 | Kondratalv |
| 2006/0149193 A1 | 7/2006 | Hall |
| 2006/0182596 A1* | 8/2006 | Dent ...................... A61B 34/70 414/699 |
| 2007/0118104 A1* | 5/2007 | Wallace ................. A61B 18/18 606/41 |
| 2007/0156019 A1 | 7/2007 | Larkin |
| 2007/0230757 A1 | 10/2007 | Trachtenberg |
| 2007/0239153 A1* | 10/2007 | Hodorek ................ A61B 34/20 606/41 |
| 2007/0250000 A1* | 10/2007 | Magnin ................ A61B 8/4461 600/114 |
| 2008/0058836 A1 | 3/2008 | Moll |
| 2008/0178654 A1 | 7/2008 | Hochmitz |
| 2008/0195003 A1* | 8/2008 | Sliwa ....................... A61N 7/02 601/3 |
| 2008/0253527 A1 | 10/2008 | Boyden |
| 2008/0262486 A1 | 10/2008 | Zvuloni |
| 2009/0018533 A1 | 1/2009 | Perkins |
| 2009/0088775 A1 | 4/2009 | Swarup |
| 2009/0105579 A1 | 4/2009 | Garibaldi |
| 2009/0143677 A1 | 6/2009 | Govari |
| 2009/0190815 A1 | 7/2009 | Dam |
| 2009/0192519 A1* | 7/2009 | Omori .................... A61B 34/37 606/130 |
| 2009/0227998 A1 | 9/2009 | Aljuri |
| 2010/0010524 A1 | 1/2010 | Barrington |
| 2010/0036384 A1 | 2/2010 | Gorek |
| 2010/0076269 A1 | 3/2010 | Makower |
| 2010/0145254 A1 | 6/2010 | Shadduck |
| 2010/0179522 A1 | 7/2010 | Companion |
| 2010/0179528 A1 | 7/2010 | Shadduck |
| 2010/0204713 A1 | 8/2010 | Ruiz Morales |
| 2010/0305439 A1 | 12/2010 | Shai et al. |
| 2010/0324414 A1 | 12/2010 | Harlev |
| 2011/0015628 A1 | 1/2011 | Dalal |
| 2011/0026786 A1 | 2/2011 | Mohamed |
| 2011/0054293 A1 | 3/2011 | Markowitz |
| 2011/0065984 A1 | 3/2011 | Ravo |
| 2011/0087087 A1 | 4/2011 | Peacock, III |
| 2011/0104800 A1 | 5/2011 | Kensy |
| 2011/0137156 A1 | 6/2011 | Razzaque |
| 2011/0139851 A1* | 6/2011 | McCuen .......... A61B 17/07207 227/175.1 |
| 2011/0172526 A1 | 7/2011 | Lachaine |
| 2011/0178389 A1 | 7/2011 | Kumar |
| 2011/0184291 A1 | 7/2011 | Okamura |
| 2011/0184391 A1 | 7/2011 | Aljuri |
| 2011/0196263 A1 | 8/2011 | Egorov |
| 2011/0201939 A1* | 8/2011 | Hubschman ............. G21K 5/10 600/476 |
| 2011/0245833 A1* | 10/2011 | Anderson ............. B25B 21/002 606/80 |
| 2011/0319815 A1* | 12/2011 | Roelle .................... A61B 34/76 604/95.01 |
| 2012/0065656 A1 | 3/2012 | Karwei |
| 2012/0150021 A1 | 6/2012 | Schwartz |
| 2012/0157841 A1* | 6/2012 | Glaenzer ........... A61B 10/0241 600/439 |
| 2012/0277763 A1 | 11/2012 | Greenblatt |
| 2012/0289973 A1* | 11/2012 | Prisco ................... A61B 34/30 606/130 |
| 2013/0072787 A1 | 3/2013 | Wallace |
| 2013/0090554 A1 | 4/2013 | Zvuloni |
| 2013/0103026 A1* | 4/2013 | Kleshinski ......... A61B 18/1492 606/41 |
| 2013/0113904 A1 | 5/2013 | Wang |
| 2013/0158534 A1 | 6/2013 | Hoey |
| 2013/0253484 A1 | 9/2013 | Aljuri |
| 2013/0253488 A1 | 9/2013 | Aljuri |
| 2013/0261540 A1 | 10/2013 | Crank |
| 2013/0267889 A1 | 10/2013 | Aljuri |
| 2013/0281839 A1 | 10/2013 | Yan |
| 2013/0317353 A1 | 11/2013 | Frank |
| 2013/0317363 A1 | 11/2013 | Case |
| 2013/0345718 A1 | 12/2013 | Crawford |
| 2014/0039519 A1* | 2/2014 | Inoue ..................... A61B 34/37 901/8 |
| 2014/0058361 A1 | 2/2014 | Gordon |
| 2014/0107417 A1 | 4/2014 | Mckinley |
| 2014/0111541 A1 | 4/2014 | Tolkowsky |
| 2014/0193833 A1 | 7/2014 | Srivastava |
| 2014/0206988 A1 | 7/2014 | Ramachandran |
| 2014/0236000 A1* | 8/2014 | Kozuka ................ A61B 6/5235 600/424 |
| 2014/0309649 A1 | 10/2014 | Alvarez |
| 2014/0378763 A1 | 12/2014 | Atarot |
| 2015/0025539 A1 | 1/2015 | Alvarez |
| 2015/0045777 A1 | 2/2015 | Aljuri |
| 2015/0057646 A1 | 2/2015 | Aljuri |
| 2015/0088107 A1 | 3/2015 | Aljuri |
| 2015/0088110 A1 | 3/2015 | Aljuri |
| 2015/0157416 A1 | 6/2015 | Andersson |
| 2015/0294497 A1 | 10/2015 | Ng |
| 2015/0313666 A1 | 11/2015 | Aljuri |
| 2015/0335344 A1 | 11/2015 | Aljuri |
| 2016/0035071 A1 | 2/2016 | Yamada |
| 2016/0074059 A1 | 3/2016 | Aljuri |
| 2016/0140751 A1 | 5/2016 | Jafarkhani |
| 2016/0143778 A1 | 5/2016 | Aljuri |
| 2016/0228141 A1 | 8/2016 | Aljuri |
| 2016/0270757 A1 | 9/2016 | Toma |
| 2016/0296291 A1 | 10/2016 | Chen |
| 2016/0324584 A1 | 11/2016 | Tahmasebi Maraghoosh |

(56)                    References Cited

U.S. PATENT DOCUMENTS

| 2017/0014203 | A1 | 1/2017 | De Mathelin |
|---|---|---|---|
| 2017/0042631 | A1 | 2/2017 | Doo |
| 2017/0172548 | A1 | 6/2017 | Aljuri |
| 2017/0172668 | A1 | 6/2017 | Aljuri |
| 2017/0202625 | A1 | 7/2017 | Bharat |
| 2017/0231655 | A1 | 8/2017 | Aljuri |
| 2017/0281282 | A1 | 10/2017 | Noonan |
| 2017/0301088 | A1 | 10/2017 | Bharat |
| 2018/0263647 | A1 | 9/2018 | Aljuri |

FOREIGN PATENT DOCUMENTS

| CN | 101040769 | | 9/2007 |
|---|---|---|---|
| CN | 101040769 | A | 9/2007 |
| CN | 101394877 | | 3/2009 |
| CN | 101460101 | A | 6/2009 |
| CN | 101472532 | | 7/2009 |
| CN | 101472532 | A | 7/2009 |
| CN | 101795636 | | 8/2010 |
| CN | 102271595 | A | 12/2011 |
| CN | 102271602 | | 12/2011 |
| CN | 102905633 | | 1/2013 |
| CN | 103118611 | | 5/2013 |
| CN | 103764056 | | 4/2014 |
| CN | 103796607 | | 5/2014 |
| EP | 1075853 | A2 | 2/2001 |
| EP | 1721567 | | 11/2006 |
| EP | 1919390 | | 5/2008 |
| EP | 3188667 | A1 | 7/2017 |
| JP | H09154803 | | 6/1997 |
| JP | H10243946 | | 9/1998 |
| JP | H11206778 | | 8/1999 |
| JP | 2001046528 | A | 2/2001 |
| JP | 2007020837 | A | 2/2007 |
| JP | 2010500153 | | 1/2010 |
| JP | 2012508068 | A | 4/2012 |
| JP | 2012523253 | A | 10/2012 |
| JP | 2013518684 | A | 5/2013 |
| JP | 2017532095 | | 11/2017 |
| WO | 03088833 | A1 | 10/2003 |
| WO | 2004004914 | | 1/2004 |
| WO | 2004028592 | A1 | 4/2004 |
| WO | 2004080529 | A2 | 9/2004 |
| WO | 2005055849 | | 6/2005 |
| WO | 2006089426 | | 8/2006 |
| WO | 2006089426 | A1 | 8/2006 |
| WO | 2007017642 | | 2/2007 |
| WO | 2007101015 | A1 | 9/2007 |
| WO | 2007/114917 | A2 | 10/2007 |
| WO | 2008083407 | A1 | 7/2008 |
| WO | 2009029461 | | 3/2009 |
| WO | 2009029461 | A1 | 3/2009 |
| WO | 2009111736 | A1 | 9/2009 |
| WO | 2009152613 | A1 | 12/2009 |
| WO | 2010054220 | A1 | 5/2010 |
| WO | 2010144419 | A2 | 12/2010 |
| WO | 2011097505 | | 8/2011 |
| WO | 2011097505 | A1 | 8/2011 |
| WO | 2011100753 | A2 | 8/2011 |
| WO | 2011141775 | A1 | 11/2011 |
| WO | 2013129657 | A1 | 9/2013 |
| WO | 2013130895 | | 9/2013 |
| WO | 2013130895 | A1 | 9/2013 |
| WO | 2014091347 | | 6/2014 |
| WO | 2014115901 | | 7/2014 |
| WO | 2014127242 | | 8/2014 |
| WO | 2014165703 | | 10/2014 |
| WO | 2015035249 | A2 | 3/2015 |
| WO | 2015200538 | A1 | 12/2015 |
| WO | 2016004071 | A1 | 1/2016 |
| WO | 2016037132 | A1 | 3/2016 |
| WO | 2016037137 | | 3/2016 |

OTHER PUBLICATIONS

Hillegersberg et al., "Water-jet-cooled Nd:YAG laser coagulation: selective destruction of rat liver metastases," Lasers Surg Med. 1991; 11(5):445-454. [Abstract Only].

International Search Report dated Jan. 21, 2016 for International Application No. PCT/US2015/048695.

Jian, et al. The Development of the Water Jet Scalpel With Air Pressure. Trans. ASME (Jun. 2001) 123(2):246-248.

Nishimura, et al. Similarity Law on Shedding Frequency of Cavitation Cloud Induced by a Cavitating Jet. Journal of Fluid Science and Technology, vol. 7, No. 3, 2012, pp. 405-420.

Prajapati, et al., Pluripotent Stem Cell within the Prostate could be Responsible for Benign Prostate Hyperplasia in Human, J Stem Cell Res Ther2014, 4:1.

Prajapati, et al., Prostate Stem Cells in the Development of Benign Prostate Hyperplasia and Prostate Cancer: Emerging Role and Concepts, Biomed Res Int 2013; 2013:107954.

Richerzhagen et al., "Water Jet Guided Laser Cutting: a Powerful Hybrid Technology for Fine Cutting and Grooving," Proceedings of the 2004 Advanced Laser Applications Conference and Exposition, Ann Arbor, Michigan, Sep. 20-22, 2004, ALAC 2004, 2:175-182; retrieved from the Internet <http://www.synova.ch/pdf/ALAC04.pdf>.

Ruggeri, et al., Activation-independent platelet adhesion and aggregation under elevated shear stress. Blood. Sep. 15, 2006; 108(6):1903-1910.

Sander et al., "The water jet-guided Nd:YAG laser in the treatment of gastroduodenal ulcer with a visible vessel. A randomized controlled and prospective study," Endoscopy. Sep. 1989; 21(5):217-220. [Abstract Only].

Sander et al., "Water jet guided Nd:YAG laser coagulation—its application in the field of gastroenterology," Endosc Surg Allied Technol. Aug. 1993; 1(4):233-238. [Abstract Only].

Stalder et al., "Repetitive Plasma Discharges in Saline Solutions," Appl. Phys. Lett. (Dec. 2001), 79(27):4503-4505.

Woloszko et al., "Plasma Characteristics of Repetitively-Pulsed Electrical Discharges in Saline Solutions Used for Surgical Procedures," (2002) IEEE Trans. Plasma Sci. 30(3):1376-1383.

Hutli, Ezddin A.F., et al., "Frequency in Shedding/Discharging Cavitation Clouds Determined by Visualization of a Submerged Cavitating Jet," Journal of Fluids Engineering, vol. 130, pp. 38-45 (Feb. 2008).

Soyama, Hitoshi, et al., "Enhancement of Impact Force around a Cavitating Jet by Changing with Nozzle Outlet Geometry," Japan Society of Mechanical Engineers, pp. 77-85 (2009).

Tang, C., et al., "Effects of Upstream Oscillating Flow on the Self-Excited Oscillation Pulsed Jet," Abstract, 1994-2023 China Academic Journal Electronic Publishing House, 4 pages.

International Preliminary Report on Patentability received for PCT Patent Application No. PCT/US2015/048695, mailed on Mar. 16, 2017, 10 pages.

Wright, et al. Cavitation of a submerged jet. Exp Fluids (2013) 54:1541.

* cited by examiner

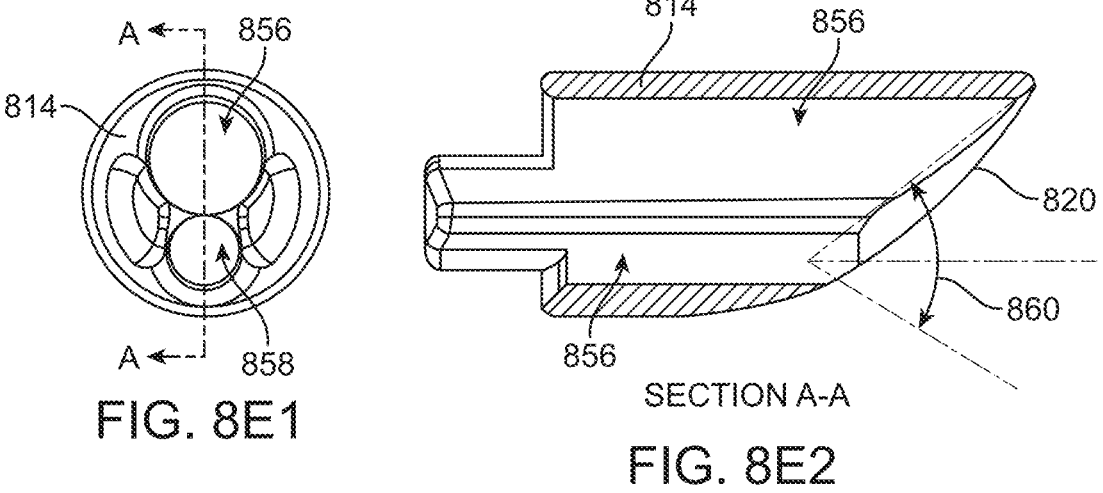
FIG. 8E1
SECTION A-A
FIG. 8E2
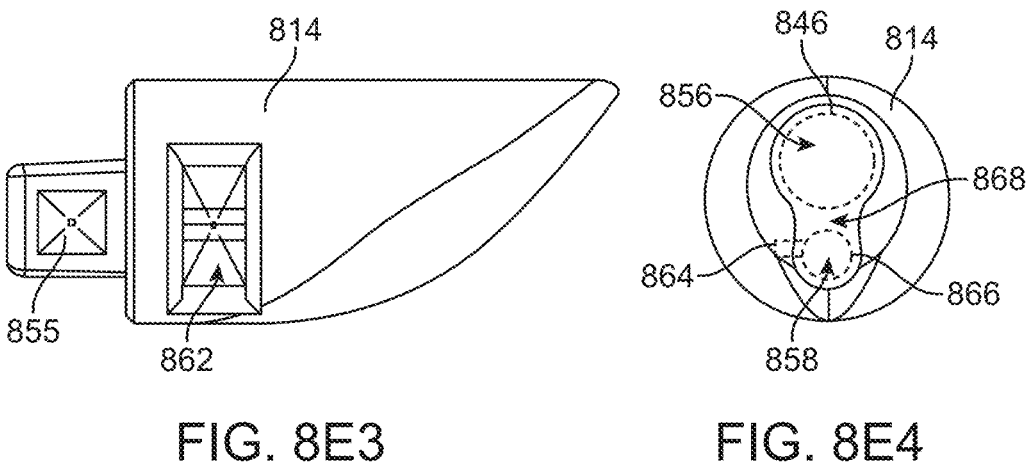
FIG. 8E3
FIG. 8E4

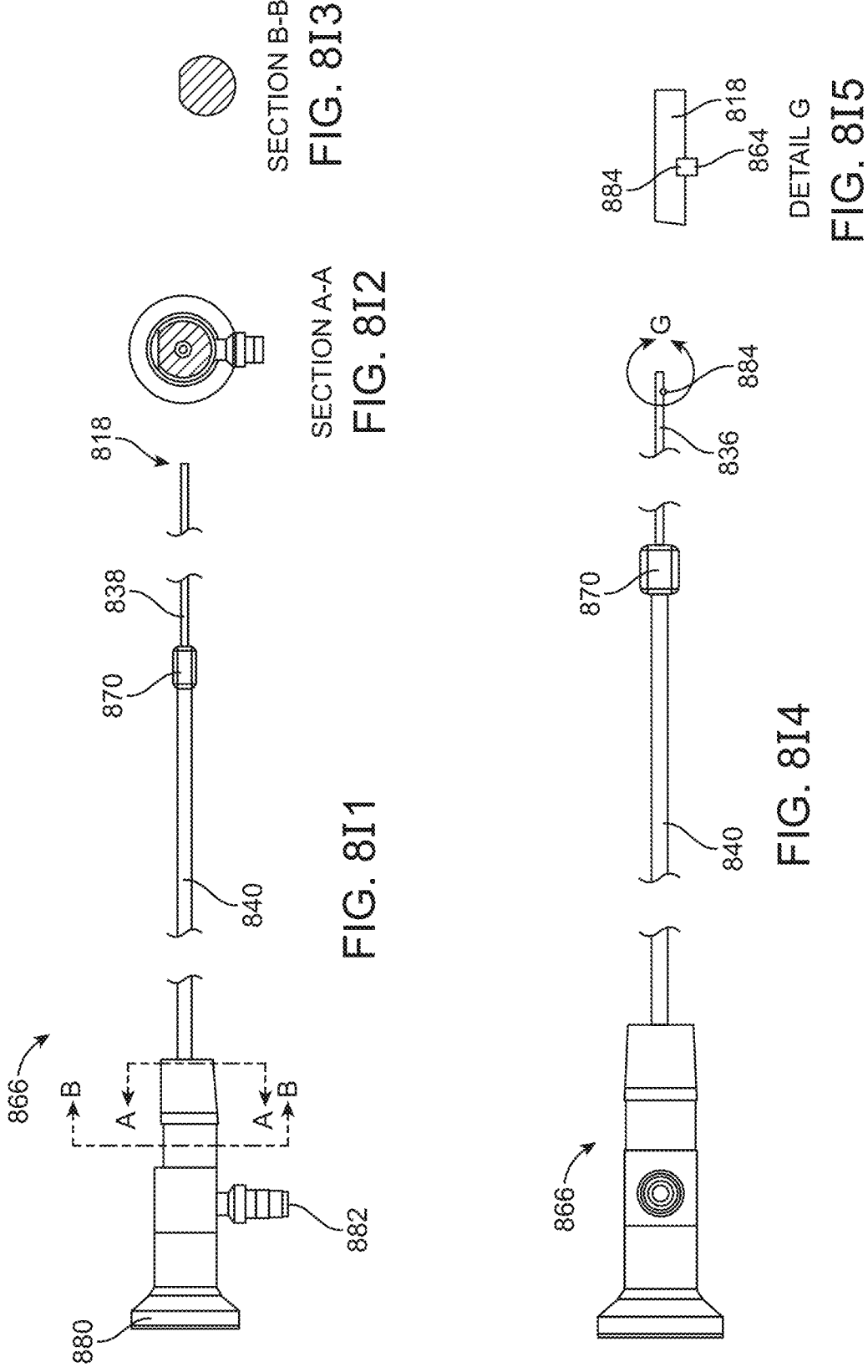
SECTION B-B
FIG. 8I3
DETAIL G
FIG. 8I5
SECTION A-A
FIG. 8I2
FIG. 8I1
FIG. 8I4

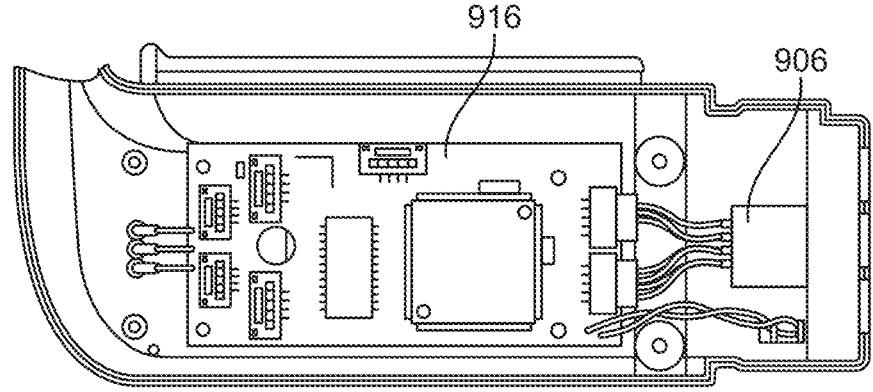
FIG. 8O1
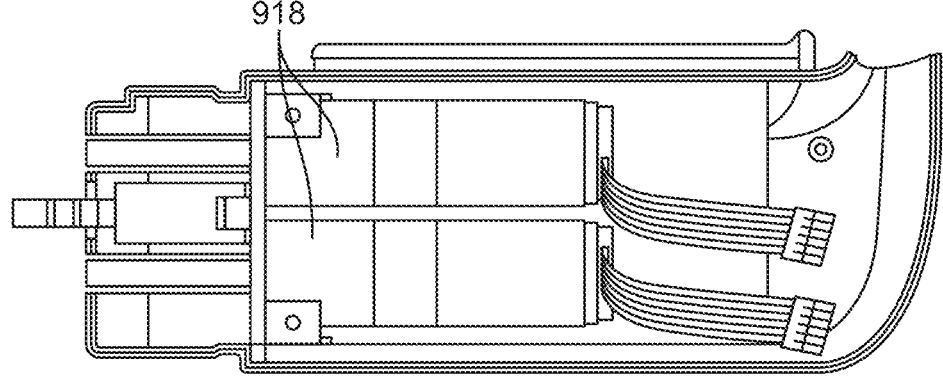
FIG. 8O2

807

846

809

Encoder logic
on = steel tube = white
off = black plastic tube = black
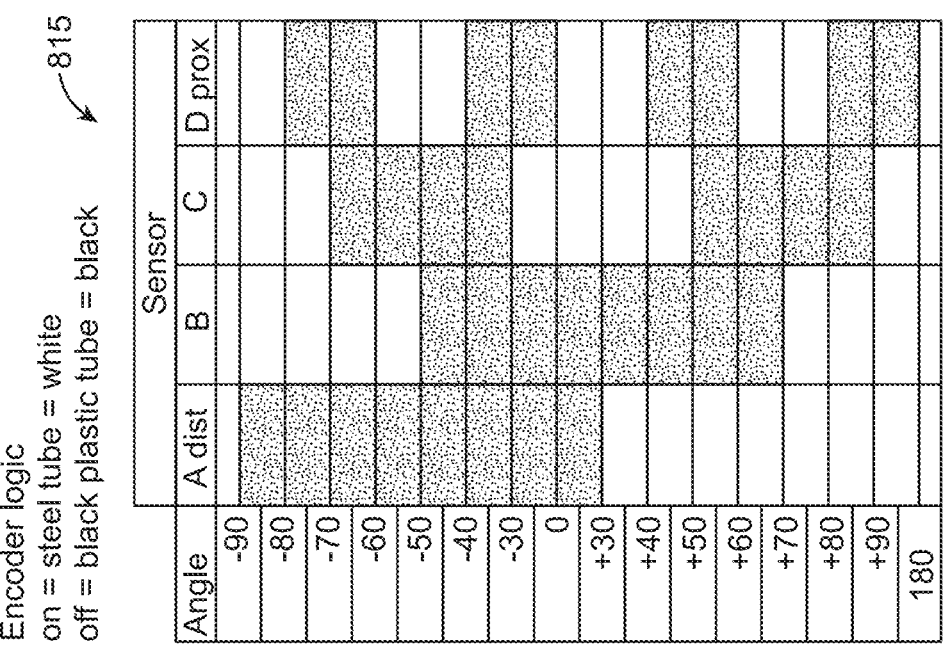
FIG. 8R2
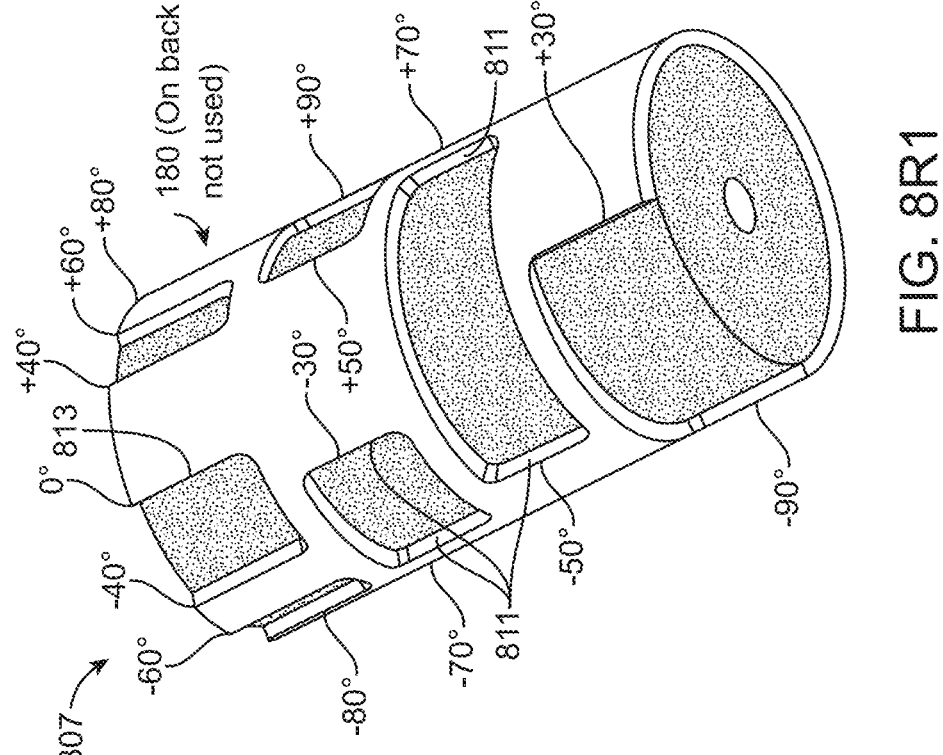
FIG. 8R1

1100

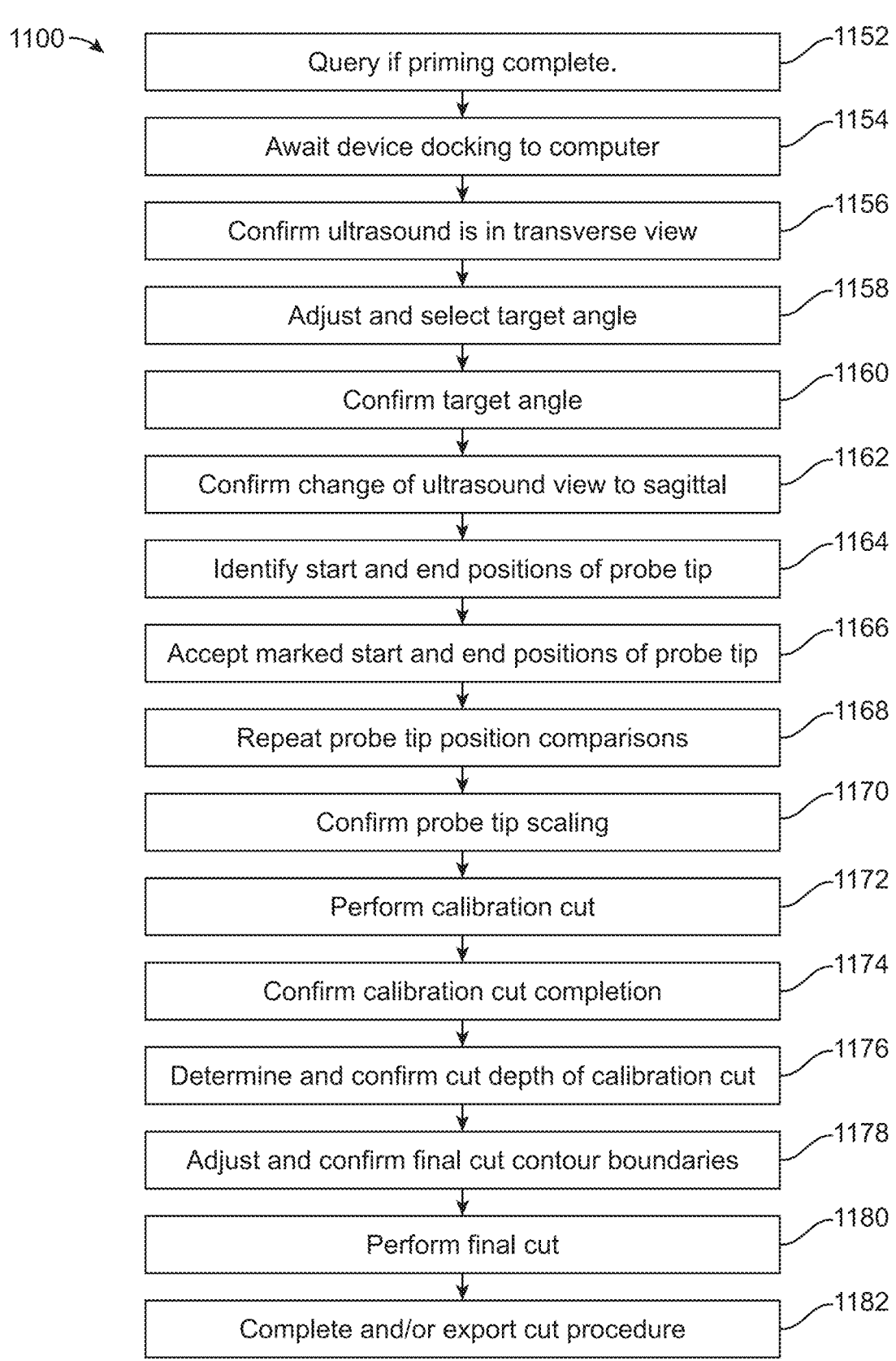

Query if priming complete. —1152

Await device docking to computer —1154

Confirm ultrasound is in transverse view —1156

Adjust and select target angle —1158

Confirm target angle —1160

Confirm change of ultrasound view to sagittal —1162

Identify start and end positions of probe tip —1164

Accept marked start and end positions of probe tip —1166

Repeat probe tip position comparisons —1168

Confirm probe tip scaling —1170

Perform calibration cut —1172

Confirm calibration cut completion —1174

Determine and confirm cut depth of calibration cut —1176

Adjust and confirm final cut contour boundaries —1178

Perform final cut —1180

Complete and/or export cut procedure —1182

FIG. 11

ELONGATE TREATMENT PROBE FOR ROBOTIC SURGERY

CROSS-REFERENCE

This application is a continuation of U.S. patent application Ser. No. 15/446,853, filed Mar. 1, 2017, now U.S. Pat. No. 11,406,453, issued Aug. 9, 2022, which is a continuation of International Application No. PCT/US2015/048695, filed Sep. 4, 2015, published as WO 2016/037137 on Mar. 10, 2016, entitled "PHYSICIAN CONTROLLED TISSUE RESECTION INTEGRATED WITH TREATMENT MAPPING OF TARGET ORGAN IMAGES," which claims priority to U.S. Provisional Patent Application No. 62/046,652, filed Sep. 5, 2014, entitled "INTEGRATED TREATMENT MAPPING WITH ULTRASOUND IMAGES," and U.S. Provisional Patent Application No. 62/046,674, filed Sep. 5, 2014, entitled "PHYSICIAN CONTROLLED TISSUE RESECTION METHODS AND APPARATUS," the entire disclosures of which are incorporated herein by reference.

The subject matter of this patent application is related to U.S. Provisional Patent Application No. 62/046,290, filed Sep. 5, 2014, entitled "GENE ANALYSIS AND GENERATION OF STEM CELL METHODS AND APPARATUS" and U.S. Provisional Patent Application No. 62/046,274, filed Sep. 5, 2014, entitled "TISSUE SAMPLING AND TREATMENT METHODS AND APPARATUS," the entire disclosures of which are incorporated herein by reference and suitable for combination in accordance with embodiments disclosed herein.

This subject matter of this patent application is related to U.S. Provisional Patent Application No. 62/019,305, filed Jun. 30, 2014, entitled "AUTOMATED IMAGE-GUIDED TISSUE RESECTION AND TREATMENT," U.S. Provisional Patent Application No. 61/972,730, filed Mar. 31, 2014, entitled "AUTOMATED IMAGE-GUIDED TISSUE RESECTION AND TREATMENT," and U.S. Provisional Patent Application No. 61/874,849, filed Sep. 6, 2013, entitled "AUTOMATED IMAGE-GUIDED TISSUE RESECTION AND TREATMENT," the entire disclosures of which are incorporated herein by reference and suitable for combination in accordance with embodiments disclosed herein.

The subject matter of this patent application is also related to International Application No. PCT/US2013/028441, filed 28 Feb. 2013, published as WO 2013/130895 on Sep. 6, 2013, entitled "AUTOMATED IMAGE-GUIDED TISSUE RESECTION AND TREATMENT," U.S. Provisional Patent Application No. 61/604,932, filed Feb. 29, 2012, entitled "AUTOMATED IMAGE-GUIDED INTRA-ORGAN RESECTION AND TREATMENT," U.S. Provisional patent application Ser. No. 12/399,585, filed Mar. 6, 2009, now U.S. Pat. No. 8,814,921, issued Aug. 26, 2014, entitled "TISSUE ABLATION AND CAUTERY WITH OPTICAL ENERGY CARRIED IN FLUID STREAM," U.S. patent application Ser. No. 12/700,568, filed Feb. 4, 2010, now U.S. Pat. No. 9,232,959, issued Jan. 12, 2016, entitled "MULTI FLUID TISSUE RESECTION METHODS AND DEVICES," U.S. patent application Ser. No. 11/968,445, filed Jan. 2, 2008, now U.S. Pat. No. 7,882,841, issued Feb. 8, 2011, entitled "MINIMALLY INVASIVE METHODS AND DEVICES FOR THE TREATMENT OF PROSTATE DISEASES," and International Application No. PCT/US2011/023781, filed Apr. 8, 2007, published as WO 2011/097505 on Nov. 8, 2011, entitled "MULTI FLUID TISSUE RESECTION METHODS AND DEVICES", the full disclosures of which are incorporated herein by reference and suitable for combination in accordance with embodiments disclosed herein.

BACKGROUND

Prior methods and apparatus for tissue removal can be less than ideal in at least some respects. The prior methods and apparatus for tissue removal can produce less than ideal results in at least some instances. Also, the prior methods and apparatus can be somewhat more complicated to use than would be ideal, and can be somewhat less reliable than would be ideal. The prior methods and apparatus can be somewhat more costly than would be ideal, such that a less than desirable number of people can receive beneficial treatments.

Work in relation to embodiments suggests that prior methods and apparatus that use an endoscope in a surgical procedure can be less than ideal in at least some respects. For example, the prior methods and apparatus may have less than ideal viewing of the surgical site in at least some instances. Also, the alignment of the prior treatments with a surgical site can be less than perfect in at least some instances. The prior surgical apparatus can provide a less than ideal cross-sectional width to access a surgical site, and the prior apparatus can be less than ideally configured to enter a surgical access path such as through a body lumen.

In light of the above, it would be desirable to provide improved methods and apparatus for tissue removal. Ideally, such devices would be easier to use, easier to align with the surgical site, be smaller, more reliable, and provide improved patient results.

SUMMARY

Embodiments of the present disclosure provide improved methods and apparatus to treat a patient. In many embodiments, an image guided treatment apparatus is configured for use with an imaging device. In many embodiments, a target resection profile is provided. The target resection profile and one or more tissue structures are displayed on an image, and the target resection profile displayed on the image is adjusted with user input. The image guided treatment apparatus can be configured to provide one or more reference structures with images obtained with the imaging device in order to allow the treatment apparatus to be used with the imaging device. The one or more reference structures may comprise a movable probe tip, or markers of the treatment apparatus. In many embodiments, the treatment apparatus is configured to move a probe tip with a calibrated movement in order to determine mapping of the image to physical coordinates of the treatment probe. The calibrated movement of the probe can determine magnification of the image and correct for errors of the magnification of the imaging probe, and can allow the imaging device to be used with many configurations and settings independently of the treatment device. The treatment apparatus may comprise one or more reference markers visible in the image that can be used to determine mapping, and the reference markers may comprise one or more structures of the treatment probe. Also, the treatment apparatus can be configured to correct for less than ideal alignment between the treatment probe and the imaging probe in order to facilitate use of the imaging device with the treatment apparatus. In many embodiments, the apparatus comprise a processor having instructions to adjust images in order to correct residual alignment errors. In many embodiments, the treatment probe is substantially aligned with a sagittal plane of an ultrasound probe such that an elongate axis of the treatment probe extends within a field of view of sagittal images, such that a substantial portion of the elongate probe appears in the sagittal image in order to show the targeted treatment zone and the elongate probe in the sagittal image. In many embodiments the elongate axis of the treatment probe extending within the sagittal image field of view may extend at a non-parallel angle to the elongate axis of the imaging probe, such that the treatment probe may appear inclined at an angle to an axis of the image, e.g. tilted in the sagittal image. In many embodiments, the sagittal images can be rotated such that an elongate axis of a treatment probe appears to be aligned with an axis of the sagittal image in order for the user to plan a treatment.

In many embodiments, a treatment table is stored on a tangible medium such as a computer readable memory. The treatment table comprises a plurality of reference locations that can be used to define the treatment.

In many embodiments, a method of resecting tissue comprises resecting tissue to a tissue resection profile. The tissue resection profile is measured, and the tissue is resected to a target profile in response to the measured tissue resection profile.

Although reference is made to treatment with the prostate, the embodiments disclosed herein are well suited for combination with other uses such as endometrial ablation, fibroid removal, prostate cancer, tumor removal, and any treatment where need catheter and precise 3D removal may be helpful.

Embodiments of the present disclosure provide improved methods and apparatus for tissue removal. In many embodiments, a surgical treatment apparatus comprises an elongate support, an elongate tube, and a movable endoscope having a stiff distal portion, in which the stiff distal portion of the endoscope is configured to move one or more components of the apparatus when the support remains substantially fixed. The support can be fixedly connected to a proximal portion of the tube to add stiffness and rigidity to the elongate tube and the support, and the support can be separated from the elongate tube with a gap extending therebetween so as to define a leakage path out of the patient which can help to inhibit over pressurization of the surgical site. The support can extend axially outside the tube and may comprise an inner concave side facing the tube in order to decrease cross-sectional size. The support may comprise a plurality of spaced apart aspiration openings near the distal end in order to facilitate alignment with the treatment site. The aspiration openings may be visible ultrasound to facilitate alignment with the patient. The endoscope configured to move distal structures of the apparatus can provide a decreased cross sectional size. In many embodiments, the stiff endoscope is configured to move at least a portion of the elongate tube. One or more components moved with the endoscope may comprise openings of a fluid delivery channel that remain a fixed distance from the endoscope when the endoscope moves in order to provide improved viewing of the surgical site when fluid released from the openings urges removed tissue away from a distal end of the endoscope. In many embodiments, a coupling connected to a distal portion of the endoscope is connected to the fluid delivery channel in order to advance and retract the openings of the fluid delivery channel with the endoscope. The coupling can be configured to receive an elongate carrier that directs energy to a target and stabilize a distal end of the elongate carrier. While the fluid delivery channel can be configured in many ways, in many embodiments the elongate telescopic tube at least partially defines the fluid channel and is connected to the distal end of the endoscope with the coupling in order to move the distal end of the elongate tube having the openings with the endoscope. The elongate telescopic tube may comprise an internal diameter sized to fit the stiff portion of the endoscope and an elongate carrier configured to direct energy to a target site. The elongate carrier can carry an energy delivery element such as a nozzle or an electrode that can be directed toward the treatment site. The coupling may comprise a guide sized to receive the elongate carrier in combination with the endoscope and allow independent motion of the carrier relative to the endoscope in order to treat the patient with rotational and translation movement of the carrier relative to the endoscope when the endoscope remains substantially stationary for at least a portion of the treatment.

In many embodiments, the coupling comprises a carrier channel to receive the carrier probe and an endoscope channel to receive the endoscope, each channel extending through the coupling. The channels may comprise a "FIG. 8" configuration with the carrier channel above the endoscope channel in a manner similar to "FIG. 8". In many embodiments, at least a portion of the carrier channel and the endoscope channel overlap. In many embodiments, the carrier channel comprises a larger cross sectional diameter than the endoscope channel.

In many embodiments, the arrangement of the support, the treatment energy carrier probe and the endoscope can allow the user to see the support, the treatment energy probe and the surgical site at the same time with the endoscope, which can make the apparatus easier to align with an anatomical reference of the patient.

In many embodiments, the support comprises an enlarged distal tip portion to reduce pressure, such as a ball shaped portion. In many embodiments, the enlarged tip provides ease of insertion. The coupling may comprise a tip portion that fits behind the enlarged distal tip as the probe is advanced to facilitate insertion into the patient.

In many embodiments, the tip of the stiff elongate support sized cross-sectionally larger than the portion of the support with aspiration with aspiration ports will urge urethra outward, and the coupling will be placed all the way forward, such that a distance of about 4 mm extends from a tip of the inclined surface of the coupling to the ball shaped tip. This configuration can allow the allow physician to see lower part of ball shaped tip during insertion.

In many embodiments, the endoscope comprises an engagement structure to engage a complementary structure of the attachment. The complementary structure of the attachment can be moved along the attachment to allow the endoscope to be removed from the attachment. The complementary structure may comprise a component of a sliding structure, such as a carriage on a rail, for example, which allows the user to articulate scope back and forth.

In many embodiments, the elongate support comprises openings arranged as fiducial markers. The openings can be spaced at regular intervals, for example about 1 cm apart, such that the support comprises a ruler capable of measuring the treatment. The openings can be visualized with ultrasound to help the user position the elongate support in the patient. While the elongate support can be positioned in many ways, in many embodiments the markers of the support can be accurately visualized with ultrasound such that the probe is capable of being positioned with ultrasound without the use of the endoscope. In many embodiments, the movement of the carrier probe tip comprising the moving energy source can be seen relative to the markers defined with the openings during treatment. In many embodiments, the openings comprise openings of an aspiration channel coupled to an aspiration source to remove resected tissue.

In many embodiments, the user of the system can visualize a plurality of markers, such as five markers of seven markers on the elongate support. In many embodiments, the user visualizes the five most proximal markers and aligns the most proximal marker with an anatomical reference such as a veramontanum of the prostate. This most proximal marker of the support may correspond to zero of the coordinate reference frame of the surgical attachment used to treat the patient.

In many embodiments, one or more of the endoscope or the carrier probe is configured to align the treatment with an anatomical reference such as veramontanum of the urethra. The veramontanum may comprise an elevation in the floor of the prostatic portion of the urethra where the seminal ducts enter the urethra, which can be seen with ultrasound or the endoscope. In many embodiments, the adjustable endoscope comprises an adjustable scope that can be advanced and retracted. The adjustable scope may comprise a mechanical stop that limits movement of the scope proximally, such that the distal end of the endoscope can be aligned with the veramontanum in order to align the reference frame of the image guided treatment with the anatomical reference such as the veramontanum. Alternatively or in combination, the energy source carried on the probe can be aligned with the reference structure such as the veramontanum. In many embodiments circuitry coupled to the probe is configured to place the probe at a location corresponding to an axial boundary of the treatment in order to align the treatment apparatus with the target surgical size. The axial boundary of the treatment can be defined as zero for the coordinate reference frame of the treatment apparatus. In many embodiments, the treatment is zeroed in on the veramontanum in order to align the surgery with the patient. Positive numbers along the treatment axis correspond to axial locations distal to the veramontanum for the treatment probe reference frame and which are proximal to the veramontanum from the patient anatomy reference frame.

In many embodiments, the markers of the elongate support comprising openings to an aspiration cannel can be aligned with an elongate ultra sound probe such as a trans rectal ultrasound probe. The markers can be aligned with the ultrasound probe in sagittal mode with in sagittal plane of the ultrasound probe extending along an elongate axis of the ultrasound probe. The handpiece can be adjusted by the user to position the plurality of markers in the sagittal plane image. If user does not see the markers in the sagittal plane image, the elongate axis of the may not be properly aligned with the sagittal plane of the ultrasound probe, and one or more of the ultrasound probe or the plurality of markers adjusted to bring the plurality of markers into the sagittal plane ultrasound image.

In many embodiments with the ultrasound probe in transverse mode, the elongate support can be moon shaped, and the user can tell if the elongate support defining the treatment axis is rotated left or right if the moon shape is distorted.

In many embodiments, the support comprising the markers is aligned to lie substantially within the sagittal plane ultrasound image such that several markers are visible in the ultrasound image. However, the plurality of markers may appear rotated at an angle in the ultrasound image in response to the markers extending along the sagittal plane in a non-parallel configuration and at an angle with respect to the ultrasound probe axis. This rotation of the markers can be adjusted with rotation of the ultrasound image, for example.

In many embodiments, the apparatus comprise a disposable attachment comprising the elongate support and the elongate tube extending from the attachment with the coupling attached to the distal end. The attachment may comprise a hand piece configured to insert the elongate support, the elongate tube and the carrier probe into the patient. The attachment may comprise a unique ID for device, which can be provided with a tangible medium such as a bar code, magnetic strip, radio frequency identification (RFID), or computer readable memory of the attachment. In many embodiments the attachment is configured for a single use. The attachment can be configured for the single use in one or more of many ways such as a processor configured to disable the attachment after being disconnected from the arm or upon receiving a signal from the processor indicating that the treatment has been completed. The single use device has the advantage of providing increased sterility to the patient. In many embodiments, the attachment comprises circuitry that stores treatment parameters. The parameters can be stored in a non-volatile memory such as flash ram. The treatment parameters may comprise one or more parameters related to treatment energy delivery such fluid flow, pressure, current, treatment locations, and the parameters can be stored as a treatment table used to treat the patient. The stored parameters can be useful for troubleshooting in the unlikely event that the treatment were to be less than ideal. The attachments can store the treatment table and other parameters, such as store aquablation flow rate and pressure. The attachment may comprise part of a tool kit customized based on the organ to be treated. In many embodiments, the attachment is configured to couple to comprises circuitry configured oscillate of drive couplings in order to align the drive couplings of the arm with the attachment.

In many embodiments, the coupling of the endoscope as described herein provides user friendly manual or automate use of the endoscope, and provides ease of use for interacting with endoscope and retracting when helpful. In many embodiments, the endoscope can be retracted prior to initiating resection, and may remain retracted during tissue resection. Upon completion of tissue resection, the endoscope can be advanced to see the surgical site without detaching the arm, and the site can be visualized without using the support the arm manually. Also the scope can be moved back and forth along axis of resection to effectively inspect the resected tissue. The endoscope can be sealed on a proximal end of a stiff portion in order to inhibit fluid from the surgical site interfering with used of the handpiece.

In many embodiments, an encoder is provided on an elongate rotating treatment shaft, which can increase accuracy and inhibit backlash. The system can be configured to drive the elongate carrier probe until the elongate carrier probe is in position. The encoder on the shaft can provide accurate reliable placement. The encoder can be located on a face of the shaft. The pattern fixed to shaft can provides improved reliability. In many embodiments, the treatment probe shaft is configured for removal. A surface intensity boundary of the encoder can be aligned with the probe tip.

In many embodiments, one or more of a hand piece or the arm comprises an adjustable power input to allow the user to adjust treatment energy in real time during the treatment.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 8E1-8E4 show the coupling in accordance with embodiments;

FIG. 8I1 shows a side view of the endoscope in accordance with embodiments;

FIG. 8I2 shows a side view along section AA as in FIG. 8I1;

FIG. 8I3 shows section BB of the endoscope of FIG. 8I1;

FIG. 8I4 shows a top view of the endoscope as in FIG. 8I1;

FIG. 8I5 shows a distal end of the endoscope as in FIG. 8I1;

FIG. 8O1 and FIG. 8O2 show internal structures of the arm components shown in FIG. 8N;

FIG. 8R1 shows an encoder in accordance with embodiments;

FIG. 8R2 shows a table showing coordinate references for different transitions measured with a plurality of photo detectors;

FIG. 11 shows a method a treating a patient, in accordance with embodiments;

DETAILED DESCRIPTION

The embodiments disclosed herein can be combined in many ways to provide improved treatments to the patient. Although reference is made to some components in some figures and other components in other figures, it is contemplated that each of these components can be combined with any one or more of the other components in order to provide an improved treatment to the patient.

As used herein, the terms proximal and distal in the context of the apparatus refer to proximal and distal as referenced from the apparatus outside the patient, such that proximal may refer to components outside the patient and distal may refer to components inside the patient.

As used herein like words and characters denote like structures.

As used herein the terms carrier probe and treatment probe are used interchangeably.

INCORPORATION BY REFERENCE

Figure 1:
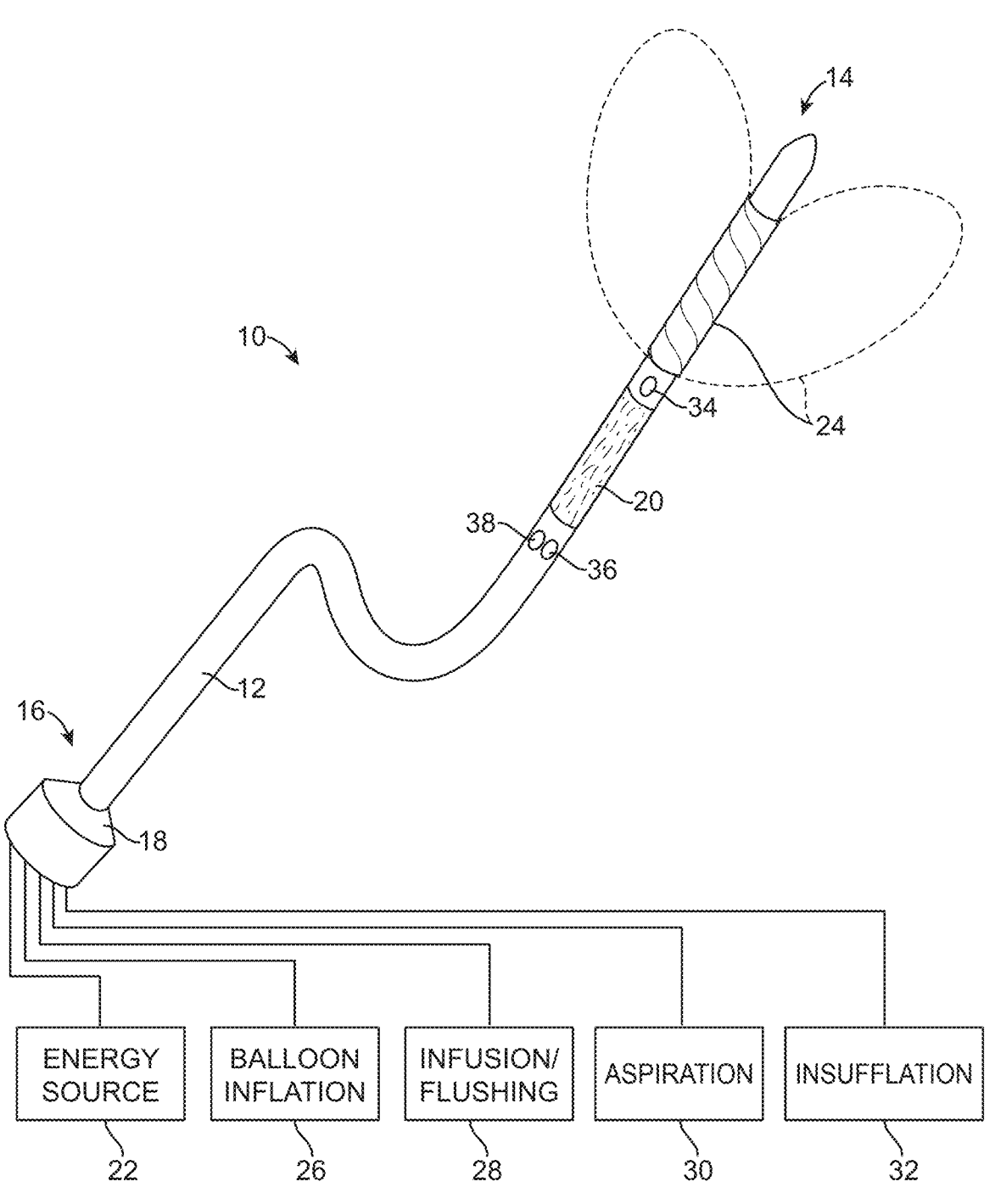
FIG. 1 is a schematic illustration of a device suitable for performing intraurethral prostatic tissue debulking in accordance with embodiments.
Figure 2A:
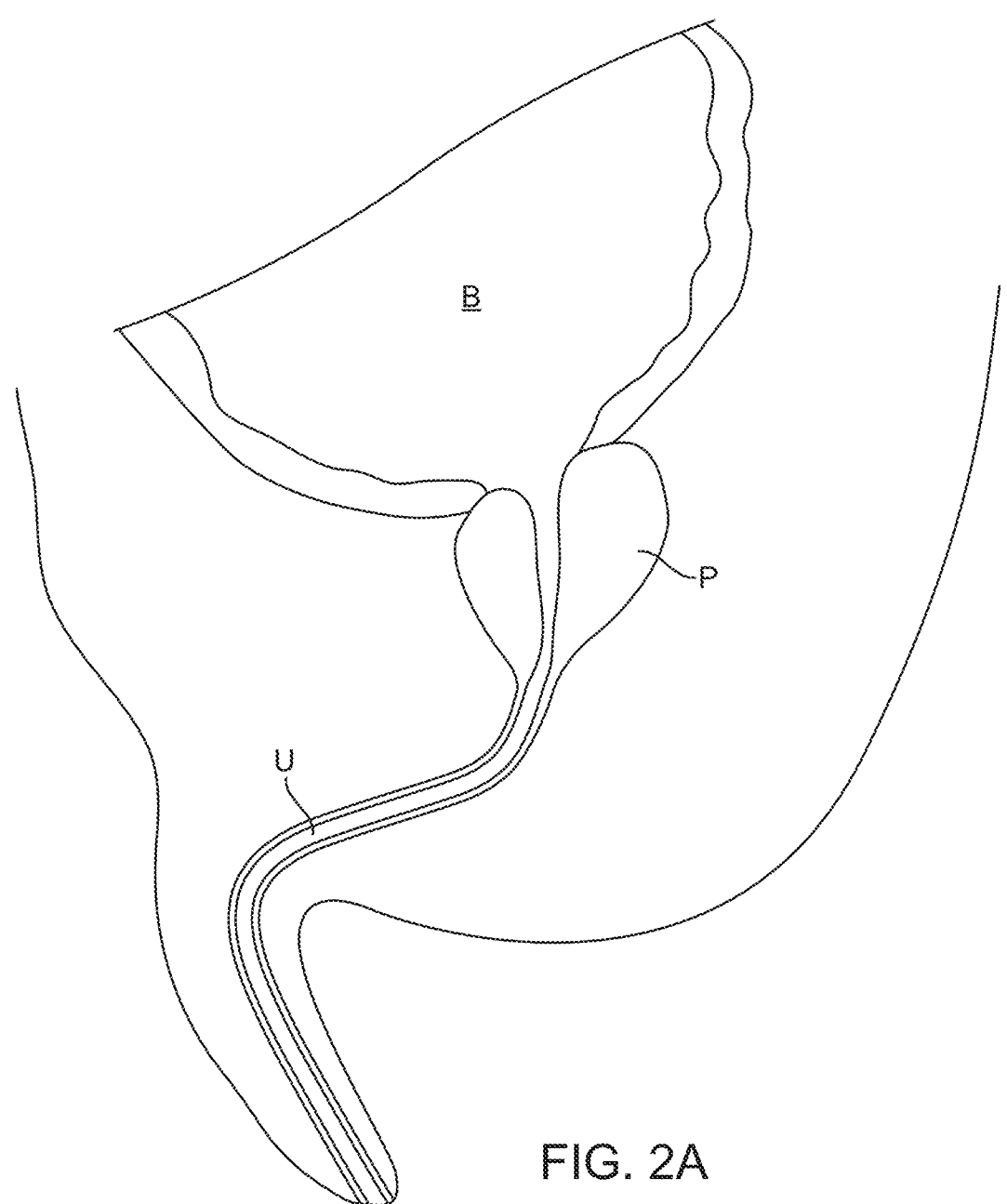
FIGS. 2A-2D illustrate use of the device of FIG. 1 in performing prostatic tissue debulking.
Figure 2B:
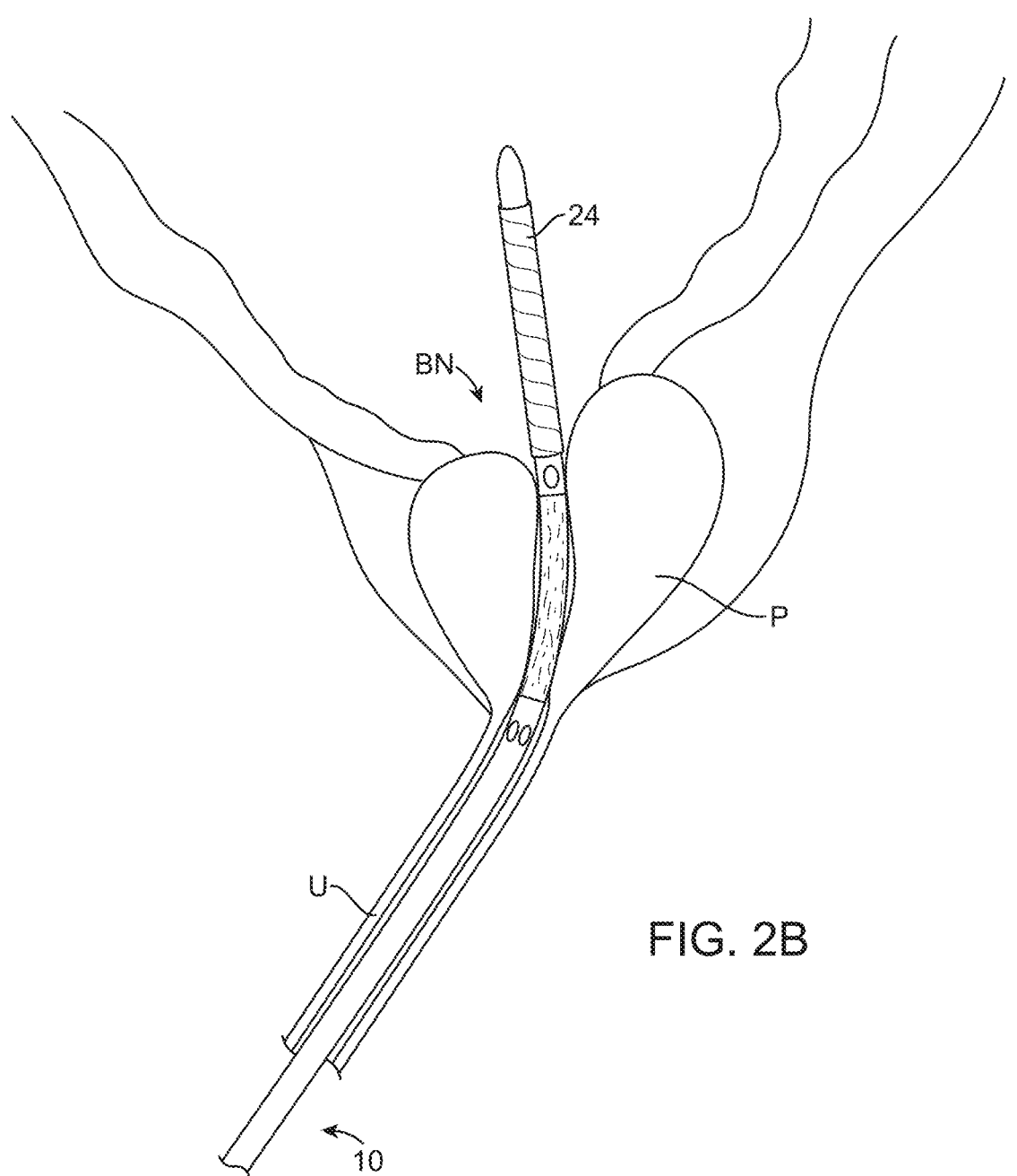
Figure 2C:
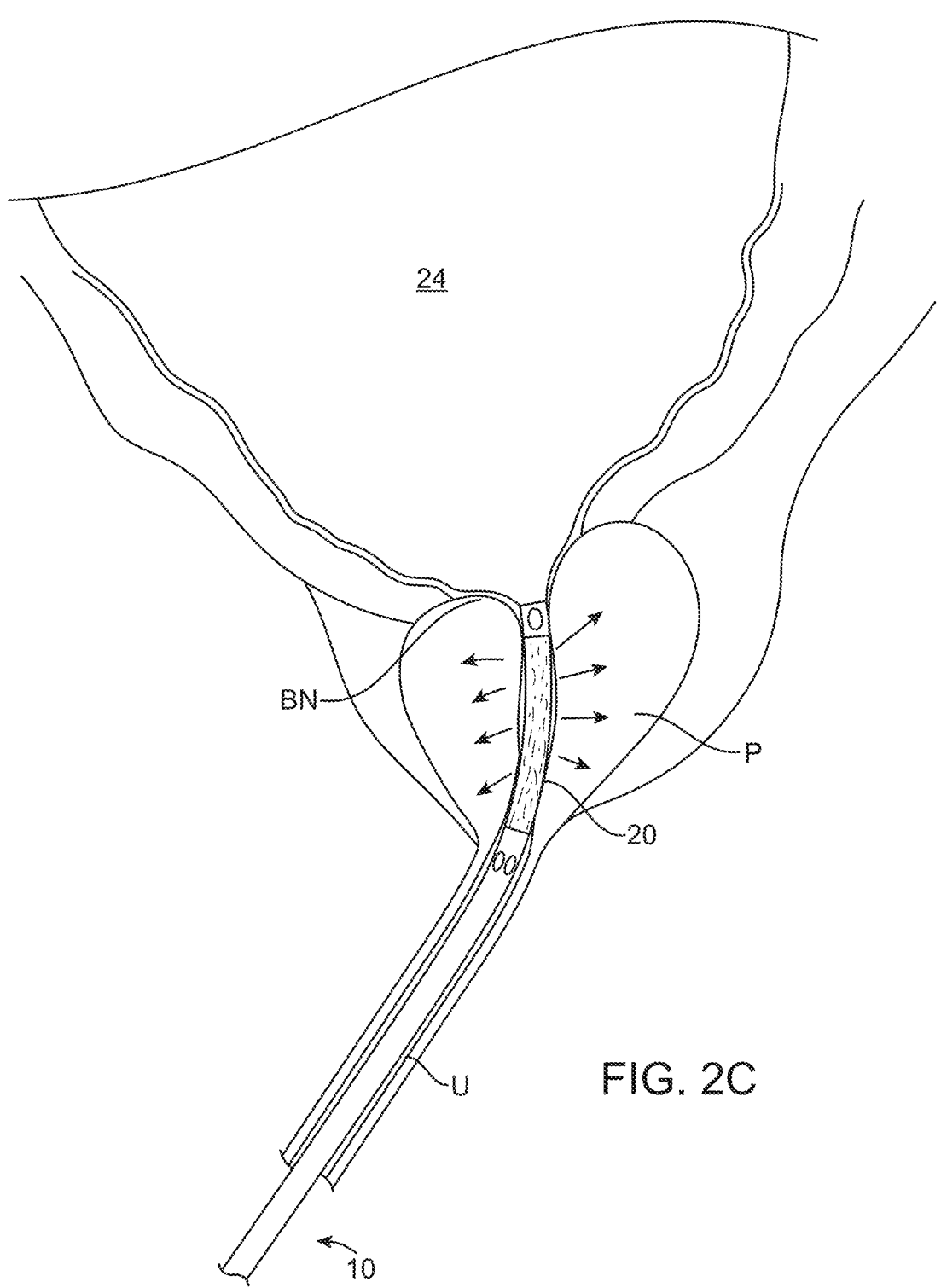
Figure 2D:
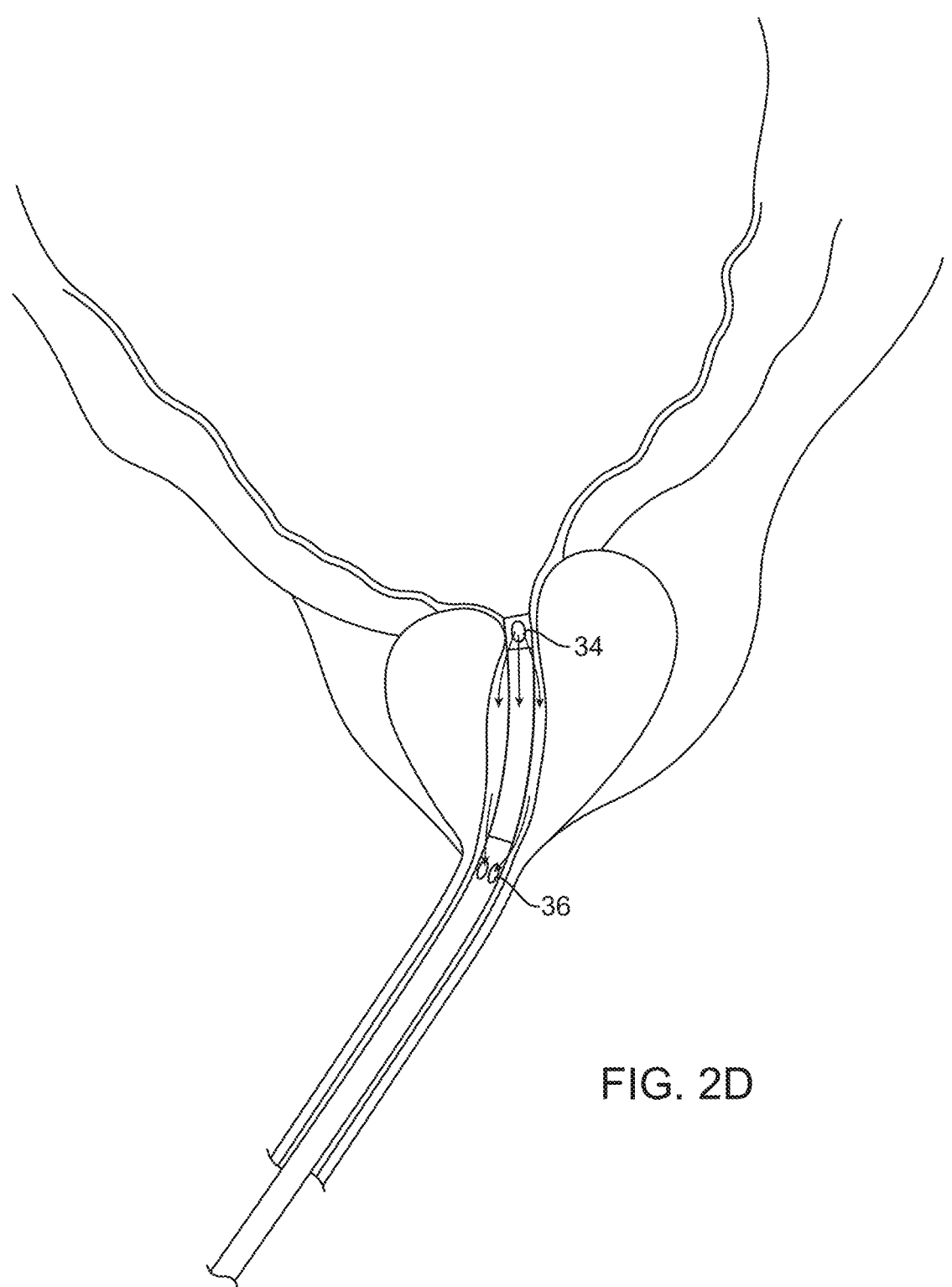

The subject matter of FIGS. 1 to 2D and the corresponding text have been incorporated by reference as described in:

U.S. application Ser. No. 12/700,568, filed Feb. 4, 2010, entitled "MULTI FLUID TISSUE RESECTION METHODS AND DEVICES", published as US 20110184391; and PCT Application PCT/US2011/023781 filed on Feb. 4, 2011, published as WO2011097505 on Nov. 8, 2011, entitled "MULTI FLUID TISSUE RESECTION METHODS AND DEVICES"; the full disclosures of which have been previously incorporated herein by reference.

Referring to FIG. 1, an exemplary prostatic tissue debulking device 10 constructed in accordance with the principles of the present invention comprises a catheter assembly generally including a shaft 12 having a distal end 14 and a proximal end 16. The shaft 12 will typically be a polymeric extrusion including one, two, three, four, or more axial lumens extending from a hub 18 at the proximal end 16 to locations near the distal end 14. The shaft 12 will generally have a length in the range from 15 cm to 25 cm and a diameter in the range from 1 mm to 10 mm, usually from 2 mm to 6 mm. The shaft will have sufficient column strength so that it may be introduced upwardly through the male urethra, as described in more detail below.

The shaft will include an energy source positioned in the energy delivery region 20, where the energy source can be any one of a number of specific components as discussed in more detail below. Distal to the energy delivery region, an inflatable anchoring balloon 24 will be positioned at or very close to the distal end 14 of the shaft. The balloon will be connected through one of the axial lumens to a balloon inflation source 26 connected through the hub 18. In addition to the energy source 22 and the balloon inflation source 26, the hub will optionally further include connections for an infusion/flushing source 28, an aspiration (a vacuum) source 30, and/or an insufflation (pressurized $CO_2$ or other gas) source 32. In the exemplary embodiment, the infusion or flushing source 28 can be connected through an axial lumen (not shown) to one or more delivery ports 34 proximal to the balloon anchor 24 and distal to the energy delivery region 20. The aspiration source 30 can be connected to a second port or opening 36, usually positioned proximally of the energy delivery region 20, while the insufflation source 32 can be connected to an additional port 38, also usually located proximal of the energy delivery region. It will be appreciated that the locations of the ports 34, 36, and 38 are not critical, although certain positions may result in particular advantages described herein, and that the lumens and delivery means could be provided by additional catheters, tubes, and the like, for example including coaxial sleeves, sheathes, and the like which could be positioned over the shaft 12.

While the present embodiments are described with reference to the human prostate, it is understood that they may be used to treat mammal prostates in general. Referring now to FIGS. 2A-2D, the prostatic tissue debulking device 10 is introduced through the male urethra U to a region within the prostate P which is located immediately distal to the bladder B. The anatomy is shown in FIG. 2A. Once the catheter 10 has been positioned so that the anchoring balloon 24 is located just distal of the bladder neck BN (FIG. 2B) the balloon can be inflated, preferably to occupy substantially the entire interior of the bladder, as shown in FIG. 2C. Once the anchoring balloon 24 is inflated, the position of the prostatic tissue debulking device 10 will be fixed and stabilized within the urethra U so that the energy delivery region 20 is positioned within the prostate P. It will be appreciated that proper positioning of the energy delivery region 20 depends only on the inflation of the anchoring balloon 24 within the bladder. As the prostate is located immediately proximal to the bladder neck BN, by spacing the distal end of the energy delivery region very close to the proximal end of the balloon, typically within the range from 0 mm to 5 mm, preferably from 1 mm to 3 mm, the delivery region can be properly located. After the anchoring balloon 24 has been inflated, energy can be delivered into the prostate for debulking, as shown by the arrows in FIG. 2. Once the energy has been delivered for a time and over a desired surface region, the energy region can be stopped and the prostate will be debulked to relieve pressure on the urethra, as shown in FIG. 2D. At that time, a flushing fluid may be delivered through port 34 and aspirated into port 36, as shown in FIG. 2D. Optionally, after the treatment, the area could be cauterized using a cauterizing balloon and/or stent which could be placed using a modified or separate catheter device.

Figure 3A:
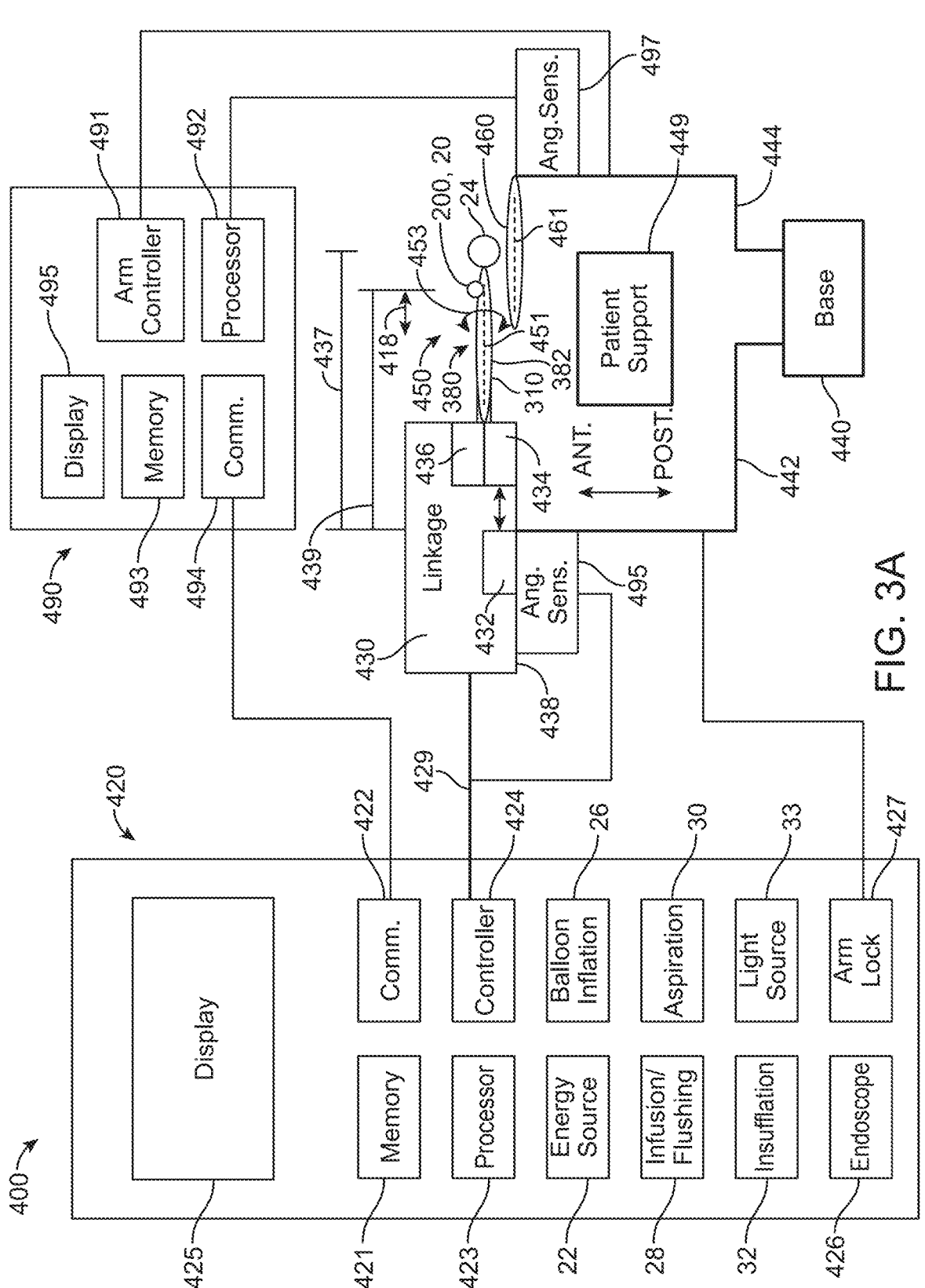
FIGS. 3A and 3B show a system to treat a patient in accordance with embodiments.
Figure 3B:
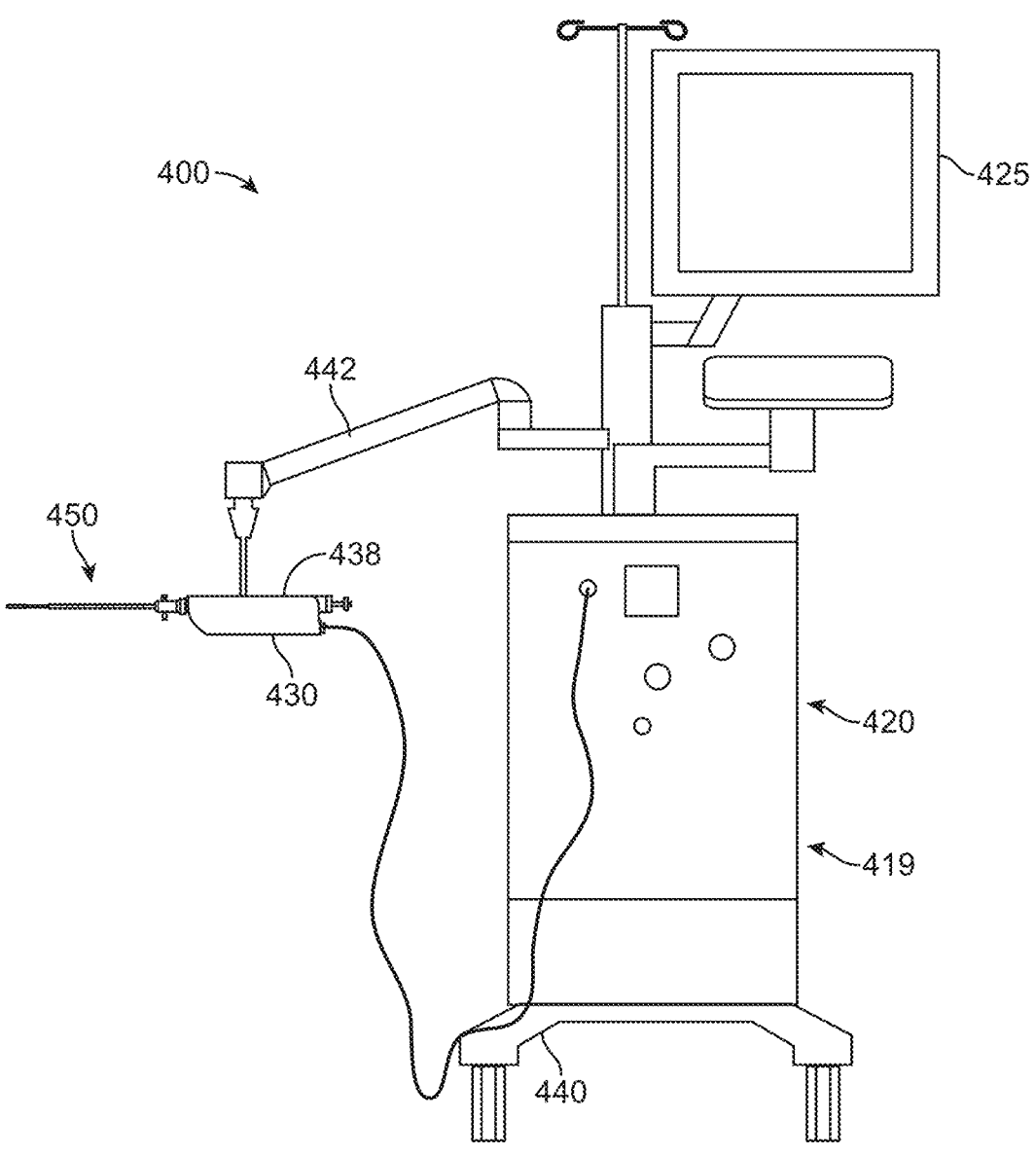

FIGS. 3A and 3B show a system to treat a patient in accordance with embodiments. The system 400 comprises a treatment probe 450 and may optionally comprise an imaging probe 460. The treatment probe 450 is coupled to a console 420 and a linkage 430. The imaging probe 460 is coupled to an imaging console 490. The patient treatment probe 450 and the imaging probe 460 can be coupled to a common base 440. The patient is supported with the patient support 449. The treatment probe 450 is coupled to the base 440 with an arm 442. The imaging probe 460 is coupled to the base 440 with an arm 444.

The patient is placed on the patient support 449, such that the treatment probe 450 and ultrasound probe 460 can be inserted into the patient. The patient can be placed in one or more of many positions such as prone, supine, upright, or inclined, for example. In many embodiments, the patient is placed in a lithotomy position, and stirrups may be used, for example. In many embodiments, the treatment probe 450 is inserted into the patient in a first direction on a first side of the patient, and the imaging probe is inserted into to the patient in a second direction on a second side of the patient. For example, the treatment probe can be inserted from an anterior side of the patient into a urethra of the patient, and the imaging probe can be inserted trans-rectally from a posterior side of the patient into the intestine of the patient. The treatment probe and imaging probe can be placed in the patient with one or more of urethral tissue, urethral wall tissue, prostate tissue, intestinal tissue, or intestinal wall tissue extending therebetween.

The treatment probe 450 and the imaging probe 460 can be inserted into the patient in one or more of many ways. During insertion, each arm may comprise a substantially unlocked configuration such the probe can be desirably rotated and translated in order to insert the probe into to the patient. When a probe has been inserted to a desired location, the arm can be locked. In the locked configuration, the probes can be oriented in relation to each other in one or more of many ways, such as parallel, skew, horizontal, oblique, or non-parallel, for example. It can be helpful to determine the orientation of the probes with angle sensors as described herein, in order to map the image date of the imaging probe to treatment probe coordinate references. Having the tissue image data mapped to treatment probe coordinate reference space can allow accurate targeting and treatment of tissue identified for treatment by an operator such as the physician.

In many embodiments, the treatment probe 450 is coupled to the imaging probe 460. In order to align the treatment with probe 450 based on images from imaging probe 460. The coupling can be achieved with the common base 440 as shown. Alternatively or in combination, the treatment probe and/or the imaging probe may comprise magnets to hold the probes in alignment through tissue of the patient. In many embodiments, the arm 442 is a movable and lockable arm such that the treatment probe 450 can be positioned in a desired location in a patient. When the probe 450 has been positioned in the desired location of the patient, the arm 442 can be locked with an arm lock 427. The imaging probe can be coupled to base 440 with arm 444, can be used to adjust the alignment of the probe when the treatment probe is locked in position. The arm 444 may comprise a lockable and movable probe under control of the imaging system or of the console and of the user interface, for example. The movable arm 444 may be micro-actuable so that the imaging probe 440 can be adjusted with small movements, for example a millimeter or so in relation to the treatment probe 450.

In many embodiments the treatment probe 450 and the imaging probe 460 are coupled to angle sensors so that the treatment can be controlled based on the alignment of the imaging probe 460 and the treatment probe 450. An angle sensor 495 is coupled to the treatment probe 450 with a support 438. An angle sensor 497 is coupled to the imaging probe 460. The angle sensors may comprise one or more of many types of angle sensors. For example, the angle sensors may comprise goniometers, accelerometers and combinations thereof. In many embodiments, angle sensor 495 comprises a 3-dimensional accelerometer to determine an orientation of the treatment probe 450 in three dimensions. In many embodiments, the angle sensor 497 comprises a 3-dimensional accelerometer to determine an orientation of the imaging probe 460 in three dimensions. Alternatively or in combination, the angle sensor 495 may comprise a goniometer to determine an angle of treatment probe 450 along an elongate axis of the treatment probe. Angle sensor 497 may comprise a goniometer to determine an angle of the imaging probe 460 along an elongate axis of the imaging probe 460. The angle sensor 495 is coupled to a controller 424. The angle sensor 497 of the imaging probe is coupled to a processor 492 of the imaging system 490. Alternatively, the angle sensor 497 can be coupled to the controller 424 and also in combination.

The console 420 comprises a display 425 coupled to a processor system in components that are used to control treatment probe 450. The console 420 comprises a processor 423 having a memory 421. Communication circuitry 422 is coupled to processor 423 and controller 422. Communication circuitry 422 is coupled to the imaging system 490. The console 420 comprises components of an endoscope 35 that is coupled to anchor 24. Infusion flashing control 28 is coupled to probe 450 to control infusion and flushing. Aspiration control 30 is coupled to probe 450 to control aspiration. Endoscope 426 can be components of console 420 and an endoscope insertable with probe 450 to treat the patient. Arm lock 427 of console 420 is coupled to arm 422 to lock the arm 422 or to allow the arm 422 to be freely movable to insert probe 450 into the patient.

The console 420 may comprise a pump 419 coupled to the carrier and nozzle as described herein.

The processor, controller and control electronics and circuitry can include one or more of many suitable components, such as one or more processor, one or more field-programmable gate array (FPGA), and one or more memory storage devices. In many embodiments, the control electronics controls the control panel of the graphic user interface (hereinafter "GUI") to provide for pre-procedure planning according to user specified treatment parameters as well as to provide user control over the surgery procedure.

The treatment probe 450 comprises an anchor 24. The anchor 24 anchors the distal end of the probe 450 while energy is delivered to energy delivery region 20 with the probe 450. The probe 450 may comprise a nozzle 200 as described herein. The probe 450 is coupled to the arm 422 with a linkage 430.

The linkage 430 comprises components to move energy delivery region 20 to a desired target location of the patient, for example, based on images of the patient. The linkage 430 comprises a first portion 432 and a second portion 434 and a third portion 436. The first portion 432 comprises a substantially fixed anchoring portion. The substantially fixed anchoring portion 432 is fixed to support 438. Support 438 may comprise a reference frame of linkage 430. Support 438 may comprise a rigid chassis or frame or housing to rigidly and stiffly couple arm 442 to treatment probe 450. The first portion 432 remains substantially fixed, while the second portion 434 and third portion 436 move to direct energy from the probe 450 to the patient. The first portion 432 is fixed to the substantially constant distance 437 to the anchor 24. The substantially fixed distance 437 between the anchor 24 and the fixed first portion 432 of the linkage allows the treatment to be accurately placed. The first portion 424 may comprise the linear actuator to accurately position the high pressure nozzle in treatment region 20 at a desired axial position along an elongate axis of probe 450.

The elongate axis of probe 450 generally extends between a proximal portion of probe 450 near linkage 430 to a distal end having anchor 24 attached thereto. The third portion 436 controls a rotation angle around the elongate axis. During treatment of the patient, a distance 439 between the treatment region 20 and the fixed portion of the linkage varies with reference to anchor 24. The distance 439 adjusts in response to computer control to set a target location along the elongate axis of the treatment probe referenced to anchor 24. The first portion of the linkage remains fixed, while the second portion 434 adjusts the position of the treatment region along the axis. The third portion of the linkage 436 adjusts the angle around the axis in response to controller 424 such that the distance along the axis at an angle of the treatment can be controlled very accurately with reference to anchor 24. The probe 450 may comprise a stiff member such as a spine extending between support 438 and anchor 24 such that the distance from linkage 430 to anchor 24 remains substantially constant during the treatment. The treatment probe 450 is coupled to treatment components as described herein to allow treatment with one or more forms of energy such as mechanical energy from a jet, electrical energy from electrodes or optical energy from a light source such as a laser source. The light source may comprise infrared, visible light or ultraviolet light. The energy delivery region 20 can be moved under control of linkage 430 such as to deliver an intended form of energy to a target tissue of the patient.

The imaging system 490 comprises a memory 493, communication circuitry 494 and processor 492. The processor 492 in corresponding circuitry is coupled to the imaging probe 460. An arm controller 491 is coupled to arm 444 to precisely position imaging probe 460.

Figure 4A:
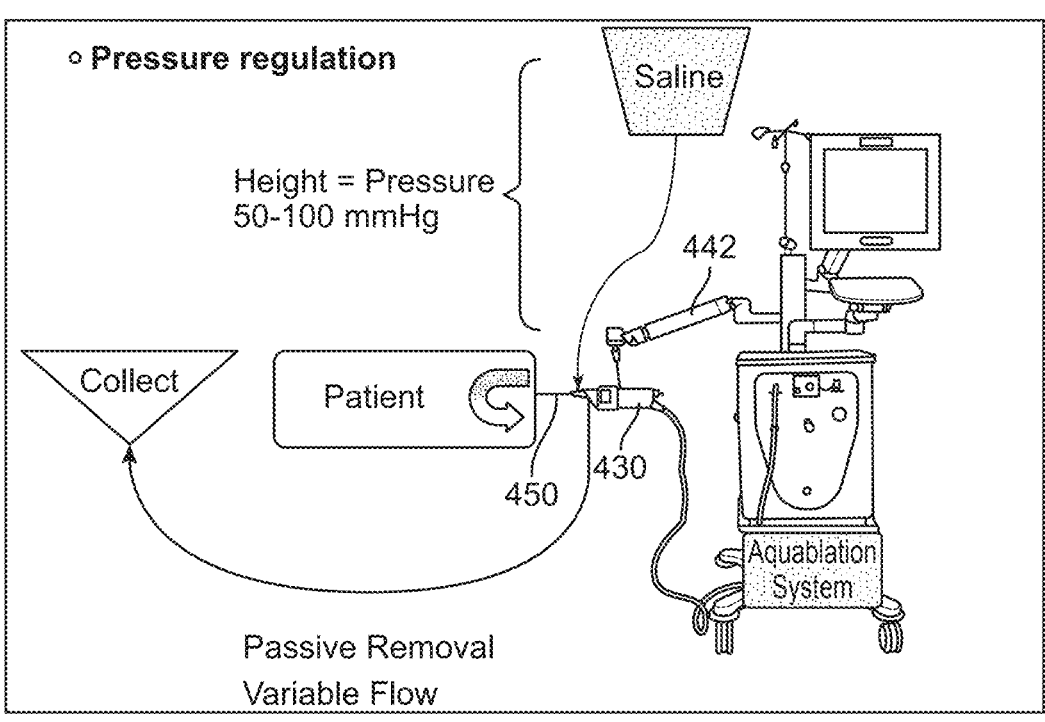
FIG. 4A shows pressure regulation of the surgical site with a substantially constant pressure and variable flow, in accordance with embodiments.

FIG. 4A shows pressure regulation of the surgical site with a substantially constant pressure and variable flow. The saline bag is placed at a height to provide substantially constant pressure regulation. The bag of saline can be placed at a height corresponding to about 50 to 100 mm of Mercury (hereinafter "mmHg"). The saline bag is coupled to the irrigation port as described herein. A collection bag is coupled to one or more of the irrigation port, the aspiration port, or the suction port as described herein. The collection bag collects tissue removed with the water jet ablation probe 450 as described herein.

Figure 4B:
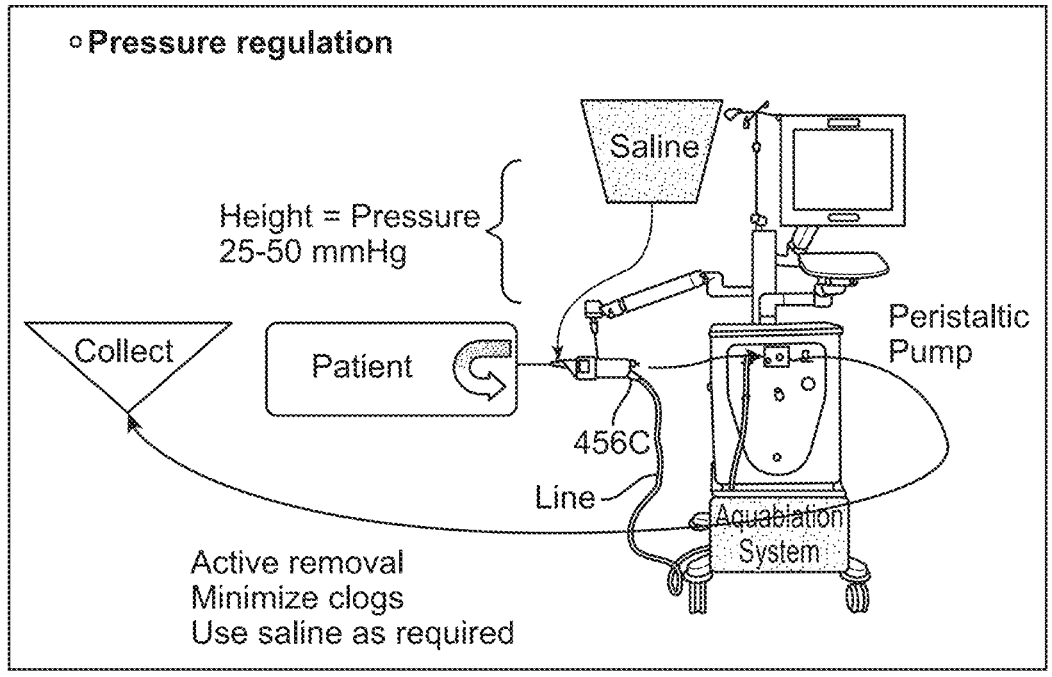
FIG. 4B shows flow regulation of the surgical site with a pump providing a substantially fixed fluidic flow and a substantially constant pressure, in accordance with embodiments.

FIG. 4B shows flow fluidic regulation of the surgical site with a pump providing a substantially fixed fluidic flow. A pump removes fluid from the surgical site at a substantially fixed flow rate. The pump may comprise a peristaltic pump, for example. The pump is configured to remove fluid at the substantially the same rate or greater than the Aquablation™ saline flow rate, in order to inhibit pressure build up at the surgical site. The peristaltic pump can be coupled to the aspiration port of the manifold comprising tissue removal port 456C as described herein, for example. Providing the pump having the flow rate that is at least the flow rate of the tissue ablation jet provides improve suction as ablated tissue that might otherwise block the tissue removal openings and channel can be subjected to greater amounts of pressure when the pump maintains the substantially fixed flow rate in order to remove the material that would otherwise block the channel.

The irrigation flow from the saline bag may remain open in order to provide at least two functions: 1) maintain pressure based on the height of the saline bag; and 2) provide a safety check valve in case the peristaltic pump is not functioning correctly as visually a person would see flow entering the bag as a pink color.

In alternate embodiments, the flow of the pump comprises a variable rate in order to provide a substantially constant pressure within the patient near the surgical site. The active sensing of pressure of the treated organ and variable flow rate of the pump may comprise a closed loop pressure regulation system. The pump can be coupled to a sensor such as a pressure sensor, and the flow rate varied to maintain substantially constant pressure. The pressure sensor can be located in one or more of many places such as on the treatment probe, within the aspiration channel of the probe, in a recess of an outer surface the probe, on an inner surface of the probe coupled to the surgical site, or near the inlet to the pump on the console for example.

Figure 5A:
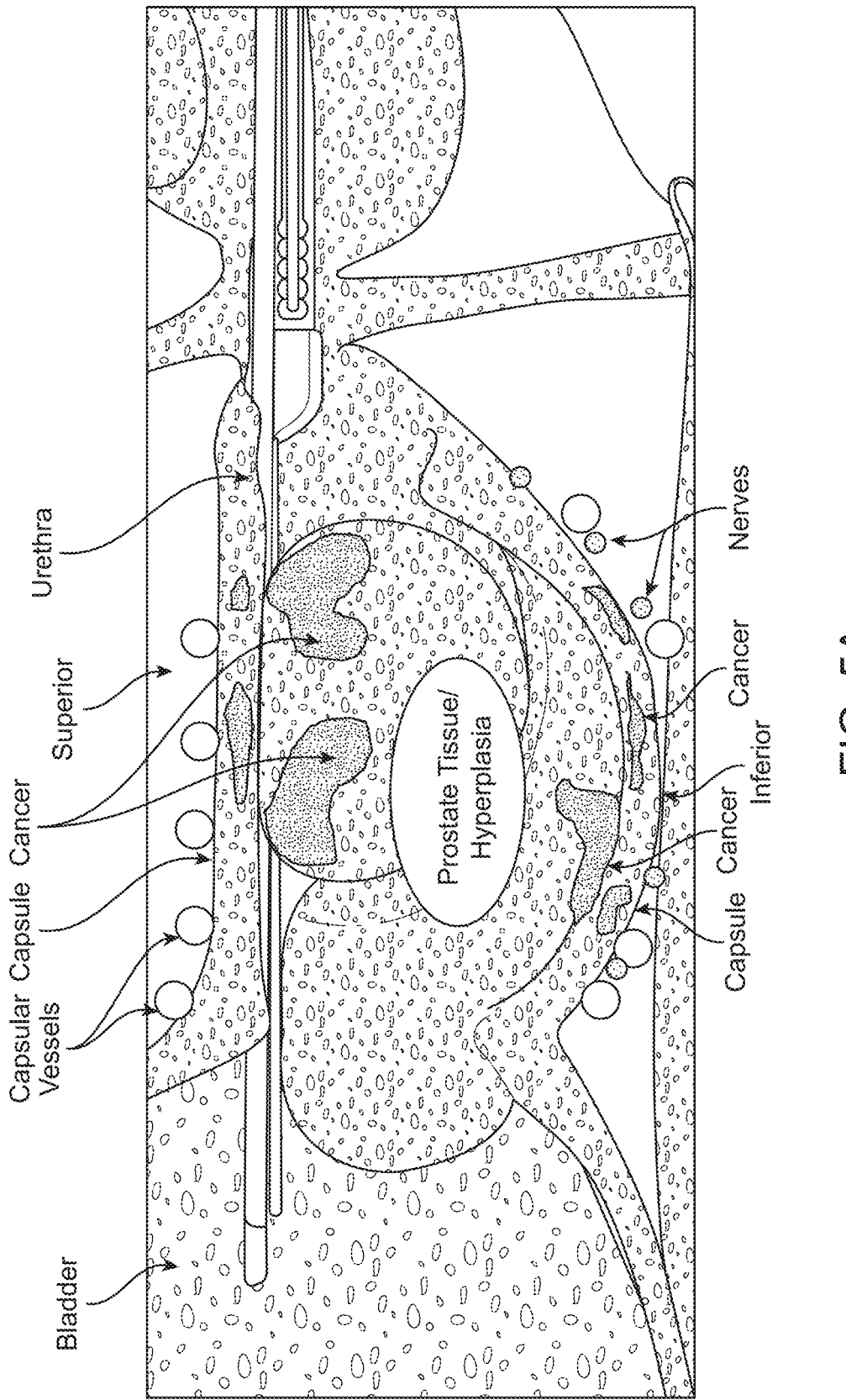
FIG. 5A shows an organ suitable for incorporation in accordance with many embodiments.

FIG. 5A shows an organ suitable for incorporation in accordance with embodiments. The organ may comprise one or more of many organs as described herein, for example, the prostate. In many embodiments the organ comprises a capsule and tissue contained within the capsule and capsular vessels and nerves located on an exterior of the capsule, for example. In many embodiments the organ comprises a prostate. The prostate may comprise hyperplasia such as benign prostate hyperplasia or cancer and combinations thereof, for example. In many embodiments the hyperplasic tissue may comprise tissue located within the patient in which the cancer may not have been detected. In many embodiments capsular vessels and nerves extend along an exterior surface of the prostate. In many embodiments the hyperplasic tissue can be located superiorly on the prostate. In the many embodiments the hyperplasic tissue may comprise tissue of unknown specificity with respect to whether the tissue comprises cancerous tissue or benign tissue.

Figure 5B:
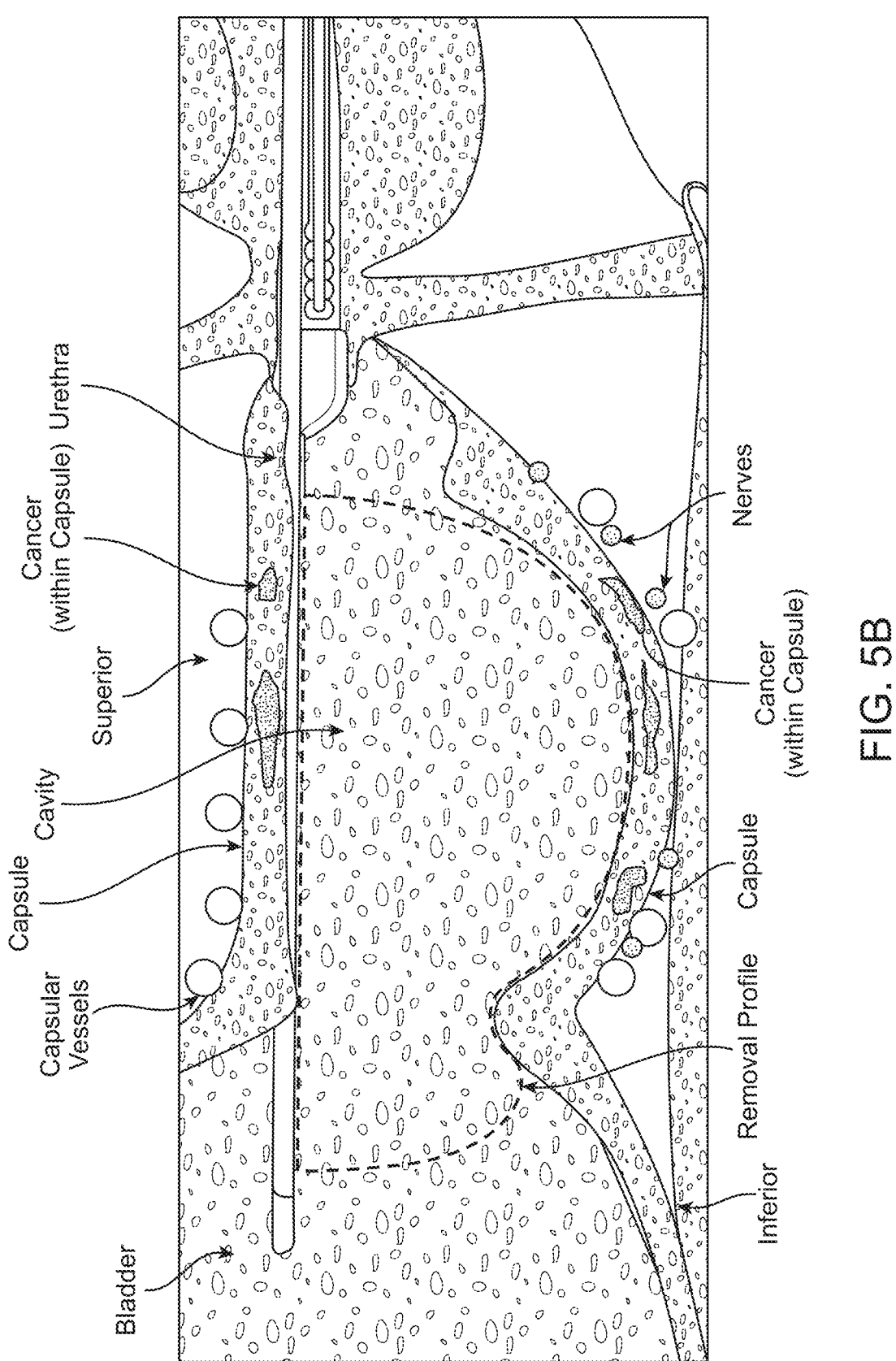
FIG. 5B shows the prostate of FIG. 5a treated with an apparatus in accordance with many embodiments.

FIG. 5B shows the prostate of FIG. 5A treated with an apparatus in accordance with embodiments. In many embodiments the tissue of the prostate is removed in accordance with a tissue removal profile. The tissue removal profile may comprise of predetermined tissue removal profile based on image-guided tissue removal as described herein, for example. Alternatively the tissue removal profile may comprise of removal profile of tissue removed with a handheld tissue removal apparatus. In many embodiments the tissue of the organ, such as the prostate, is removed to within the capsule in order to decrease the distance from the tissue removable profile to the exterior of the capsule, for example.

An apparatus for tissue removal may comprise a nozzle configured to deliver a fluid stream, wherein the fluid stream may comprise one or more of a liquid or a gas. A liquid fluid stream may comprise one or more of water or saline, for example. A liquid fluid stream may be configured to exit the nozzle in the form a liquid ablation jet, causing cavitations in the prostate tissue and dissociating the tissue into a plurality of fragments. The liquid fluid stream can be released into a liquid in which the nozzle is immersed in order to provide cavitation with shedding pulses as described herein. The liquid in which the nozzle is immersed may comprise one or more of water or saline, for example.

Figure 6A:
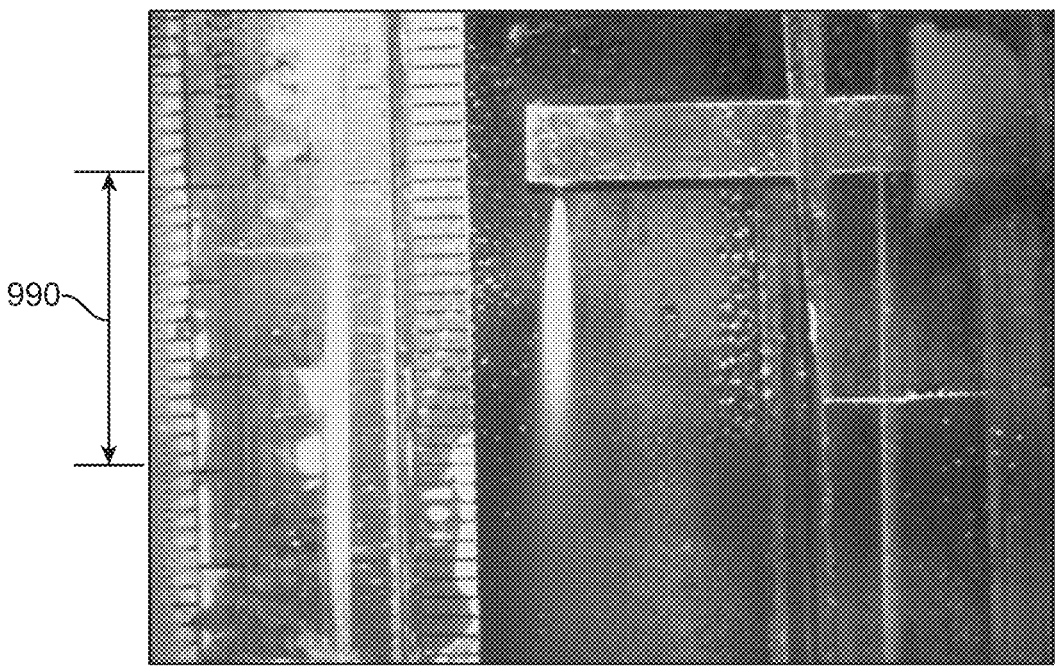
FIG. 6A shows an ablative flame visible to the human eye, in accordance with embodiments.

FIG. 6A shows an ablative flame visible to the human eye, in accordance with embodiments.

Figure 6B:
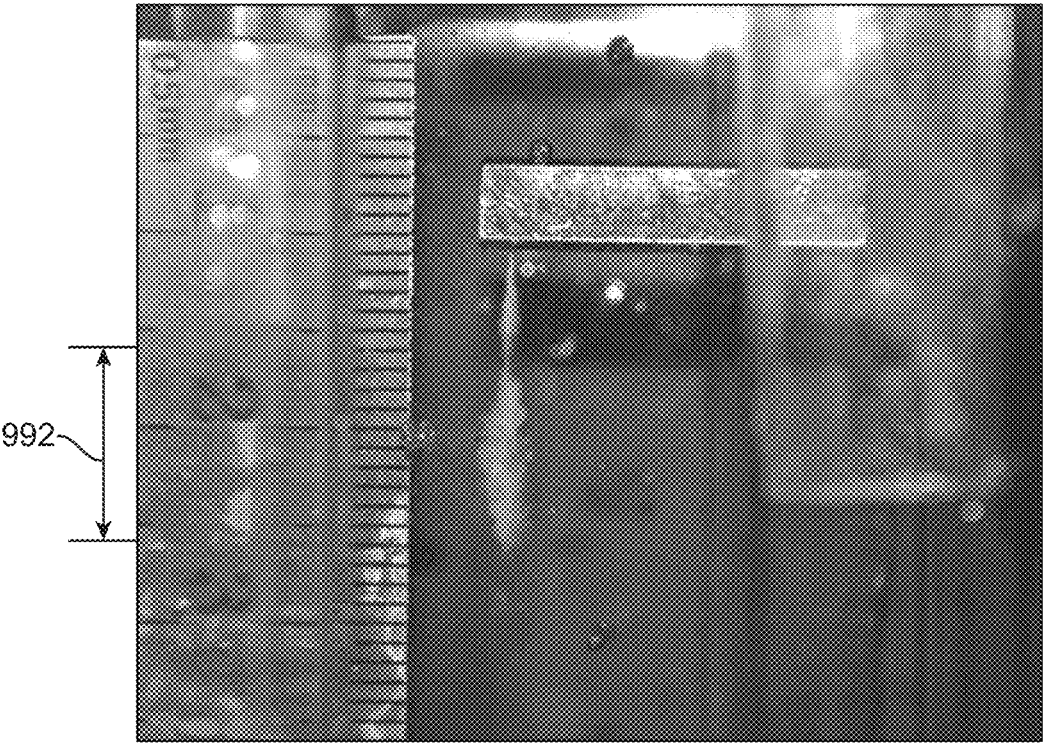
FIG. 6B shows a high speed image of the ablative flame as in FIG. 6A.

FIG. 6B shows a high speed image of the ablative flame as in FIG. 6A. The image was taken at a speed of about $\frac{1}{400}$ of a second.

The data of FIGS. 6A and 6B show that the ablative flame comprises a plurality of white clouds generated with the ablative stream when released from the nozzle. Work in relation to embodiments has shown that the cavitating cloud can shed from the jet at a characteristic shedding frequency. A length 992 of each cloud is related to the shedding frequency and the velocity of the cloud. The relatively cool ablative flame of the jet comprises a length 990 corresponding to the cutting length of the jet which can be adjusted to cut tissue to controlled depth as described herein. In many embodiments, nozzle of the jet is placed at least about a quarter of the length 992 of a shed cloud in an non-cutting configuration as shown in FIG. 6B, in order to allow the shedding cloud to substantially form prior to the cloud striking tissue. This divergence of the shed cloud to a larger cross sectional size can also provide improved tissue removal as the cloud can be distributed to a larger region of tissue and provide improved overlap among the pulses of the jet.

In addition to the impact pressure of the jet, the highly turbulent and aggressive region corresponding to the white cloud of the image contributes substantially to the ablation of tissue as described herein. The white cloud comprises a plurality of cavitation regions. When pressurized water is injected into water, small cavitations are generated in areas of low pressure in the shear layer, near the nozzle exit. The small cavitations may comprise cavitation vortices. The cavitation vortices merge with one another, forming large discrete cavitation structures that appear in the high speed images as cavitation clouds. These cavitation clouds provide effective ablation when interacting with tissue. Without being bound by any particular theory, it is believed that the cavitation clouds striking tissue cause substantial erosion of tissue related to the cavitations in combination of the high velocity fluid that defines the cavitations striking tissue.

The nozzle and pressure as described herein can be configured to provide the pulsatile clouds, for example with control of the angle of the nozzle, by a person of ordinary skill on the art based on the teachings provided herein. In many embodiments, the nozzle of the fluid delivery element comprises a cavitating jet in order to improve ablation of tissue.

The fluid delivery element nozzle and pressure can be arranged to provide a shedding frequency suitable for removal of tissue.

In many embodiments, the "white cloud" of "flame" comprises an "entrainment" region where surrounding water is drawn in or "entrained" into the jet. Work in relation to embodiments suggests that the entrainment of fluid can be related to the shedding frequency.

The shedding frequency and size of the cloud shed from the jet can be used to provide tissue ablation in accordance with embodiments. The shedding frequency can be combined with the angular sweep rate of the probe around the longitudinal axis to provide overlap of the locations where each cloud interacts with the tissue.

Figure 7:
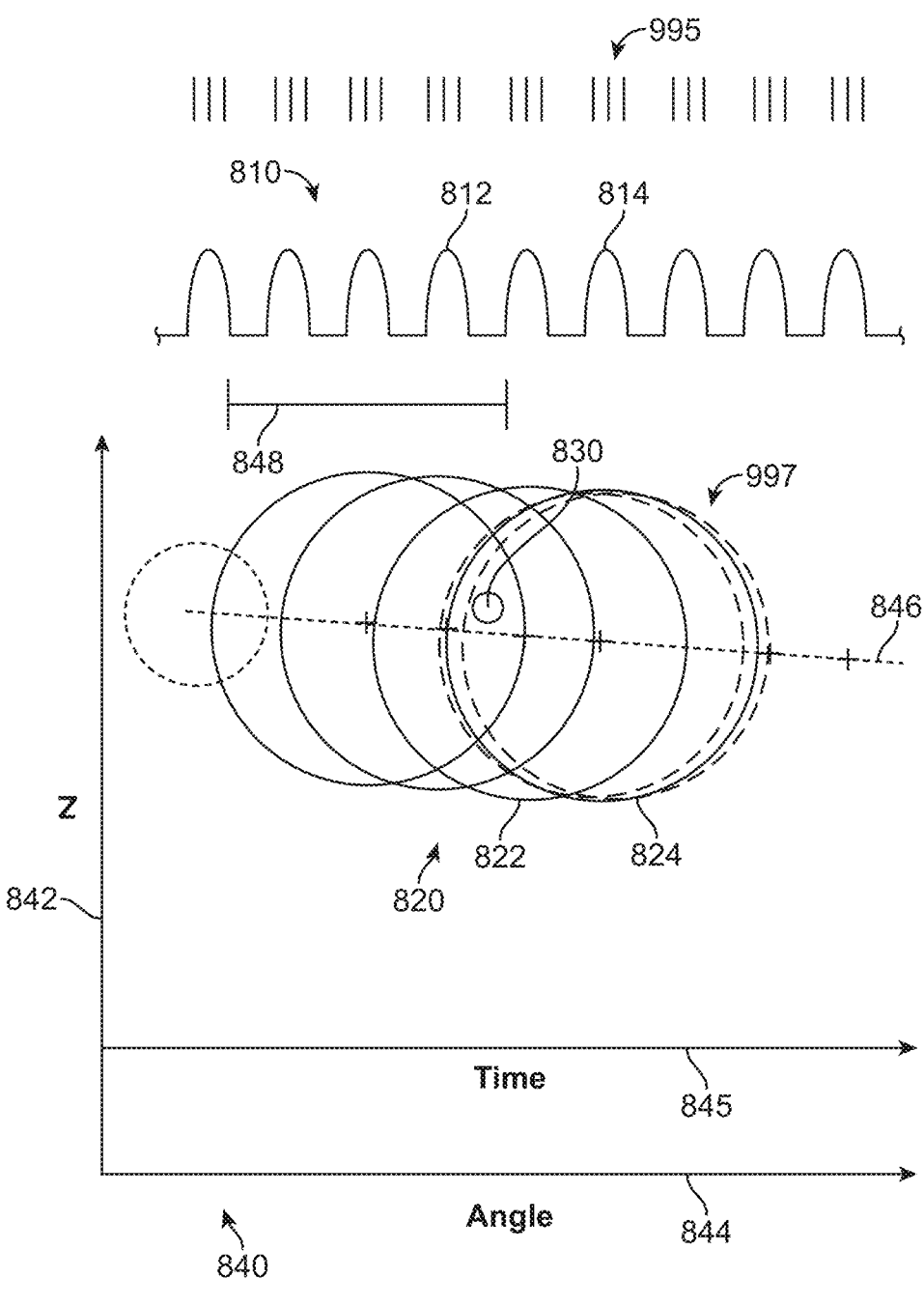
FIG. 7 shows a plurality of shedding pulses and sweeping of the ablative jet to provide smooth and controlled tissue erosion at a plurality of overlapping locations in accordance with embodiments.

FIG. 7 shows a plurality of shedding pulses 995 and sweeping of the ablative jet to provide smooth and controlled tissue erosion at a plurality of overlapping locations 997 in accordance with embodiments. This shedding frequency can be substantially faster than the pump frequency, when a pump is used, such that a plurality of shedding clouds are provided for each pulse of the pulsatile pump. The sweep rate of the probe can be related to shedding frequency to provide improved tissue removal, for example with the shedding clouds configured to provide overlapping pulses.

In many embodiments, the system comprises a pump having a frequency less than a frequency of the shedding pulses, in order to provide a plurality of shedding pulses for each pulse of the pump. The pump can have a pulse rate of at least about 50 Hz, for example within a range of about 50 Hz to about 200 Hz, and the shedding pulses comprise a frequency of at least about 500 Hz, for example within a range from about 1 kHz to about 10 kHz.

Although pulses of a pump are illustrated, similar scanning of pulsed clouds can be provided with a continuous flow pump.

While the nozzle can be configured in one or more of many ways, in many embodiments the nozzle comprises a Strouhal number (hereinafter "St") within a range from about 0.02 to about 0.3, for example within a range from about 0.10 to about 0.25, and in many embodiments within a range from about 0.14 to about 0.2.

In many embodiments, the Strouhal number is defined by:

$$St=(Fshed)*(W)/U$$

where Fshed is the shedding frequency, W is the width of the cavitating jet, and U is the velocity of the jet at the exit. A person of ordinary skill in the art can modify nozzles as described herein in order to obtain shedding frequencies suitable for combination in accordance with embodiments described herein, and experiments can be conducted to determine the cloud lengths and shedding frequencies suitable for tissue removal.

The nozzle configurations providing plurality of shedding clouds are suitable for use with one or more of the probes as described herein.

Figure 8A:
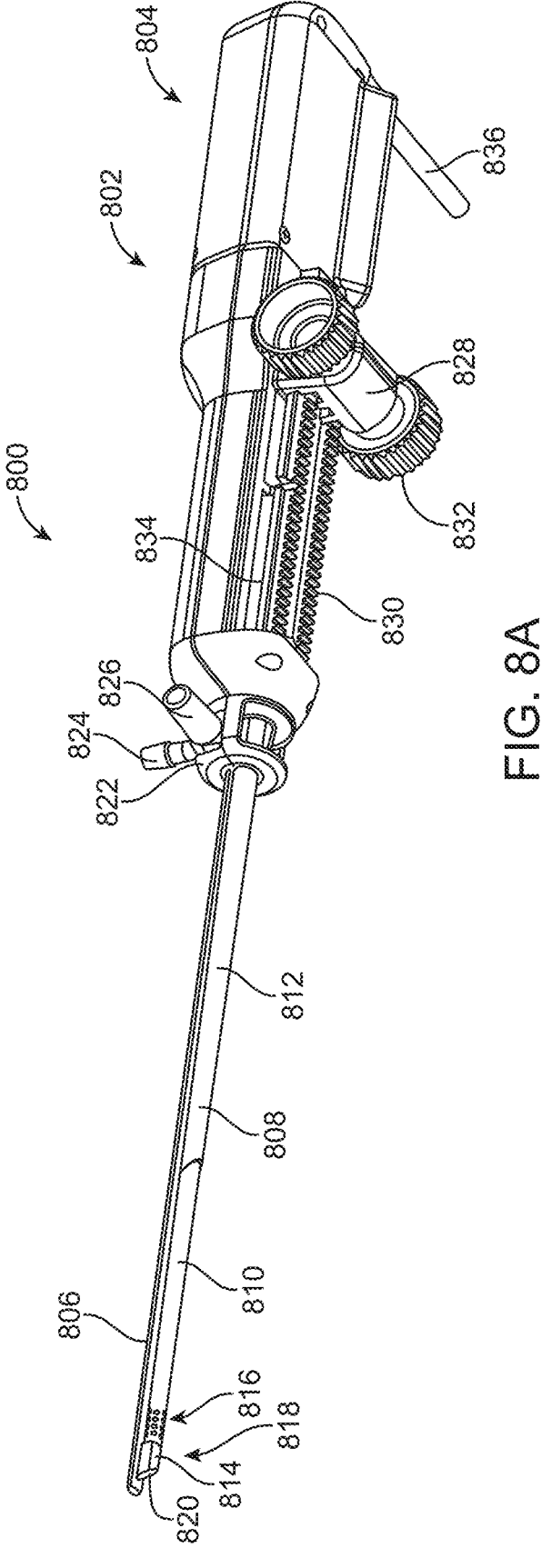
FIG. 8A shows an attachment device in accordance with embodiments.

FIG. 8A shows an attachment device 800 in accordance with embodiments. The attachment device is configured to attach to an arm as described herein. The attachment device comprises one or more components of the surgical system to treat the patient as described herein. In many embodiments the attachment device comprises a handpiece 802 for the surgeon to manipulate the attachment device with the arm in the unlocked position in order to insert the distal end of the attachment device into the patient. In many embodiments the attachment device comprises a linkage 804 comprising rotatable bodies configured to receive torque in rotation from the arm as described herein.

The attachment device comprises a plurality of components sized to fit within a surgical access site of the patient such as a urethra, for example. The attachment device may comprise the elongate support 806, the elongate tube 808 and the coupling 814 as described herein, for example. The elongate support 806 comprises a stiff support configured for insertion into the patient. The elongate support may comprise a rounded distal end in order to facilitate insertion into the patient along an access path in order to expand the path to allow and facilitate insertion of the coupling. The elongate support may comprise a plurality of aspiration channels located to remove tissue excised from the surgical site. The elongate support may comprise a plurality of channels extending from an aspiration port 828 to the openings on the distal end of the elongate support.

The elongate tube 808 may comprise a telescopic tube comprising a first distal portion 810 and a second proximal portion 812. The second portion can be sized larger than the first portion in order to receive the first portion and allow sliding of the tube. The coupling 814 on the distal end of the distal portion of the tube can be connected to an endoscope. The endoscope connected to the coupling can be moved proximally and distally and the elongate tube can shorten and decrease in length as the coupling moves proximally and distally with the distal tip 818 of the endoscope.

The coupling 814 may comprise inclined distal surfaces 820 or at least one surface that is shaped to facilitate the insertion of the coupling into the patient. The coupling can be placed adjacent to the distal end of the elongate support when the attachment device is inserted into the patient. The endoscope tip 818 can be coupled to the coupling with structures of the coupling. For example, the coupling may comprise an engagement structure shaped to receive a corresponding engagement structure on the endoscope tip such that the coupling mates with the endoscope tip and is effectively keyed and locked to the endoscope tip. Proximal and distal movement of the endoscope can move the coupling proximally and distally with a corresponding decrease or increase in the length of the elongate tube.

The attachment device may comprise a hub 822 comprising the irrigation port 824 and the aspiration port 826. The irrigation port can be coupled to the internal channel of the elongate tube in order to direct fluid such as saline to irrigation openings 816 located on the distal end of the elongate tube. The irrigation openings can provide fluid to the surgical site such as saline. Alternatively, a fluid such as a gas can be provided to the surgical site with insufflation. The aspiration port on the hub can be connected to openings on the elongate support with channels extending axially along the elongate support.

The elongate tube 808 of the endoscope comprises a first distal portion 810 of the tube and a second proximal portion 812 of the elongate telescopic tube. The second proximal portion is sized larger than the first distal portion in order to slidingly receive the first distal portion to allow the coupling to move proximally and distally with the endoscope.

The attachment device comprises a plurality of structures that allow a user such as a physician to adjust the endoscope independently of other components of the device. In many embodiments, the endoscope is coupled to an endoscope carriage 828. The endoscope carriage can be advanced and retracted in order to move the distal end of the endoscope connected to the coupling proximally and distally. The attachment device may comprise a rack 830 that is coupled to a pinion gear that allows the endoscope carriage to be moved proximally and distally with rotation of a knob 832 on the endoscope carriage. The attachment device may comprise a rail 834 to engage the endoscope carriage such that the endoscope carriage can slide along the rail with rotation of the knob, for example. In many embodiments the attachment device comprises a connection of a high pressure cable 836 with a carrier that carries a source of treatment energy under control of the linkage.

Figure 8B:
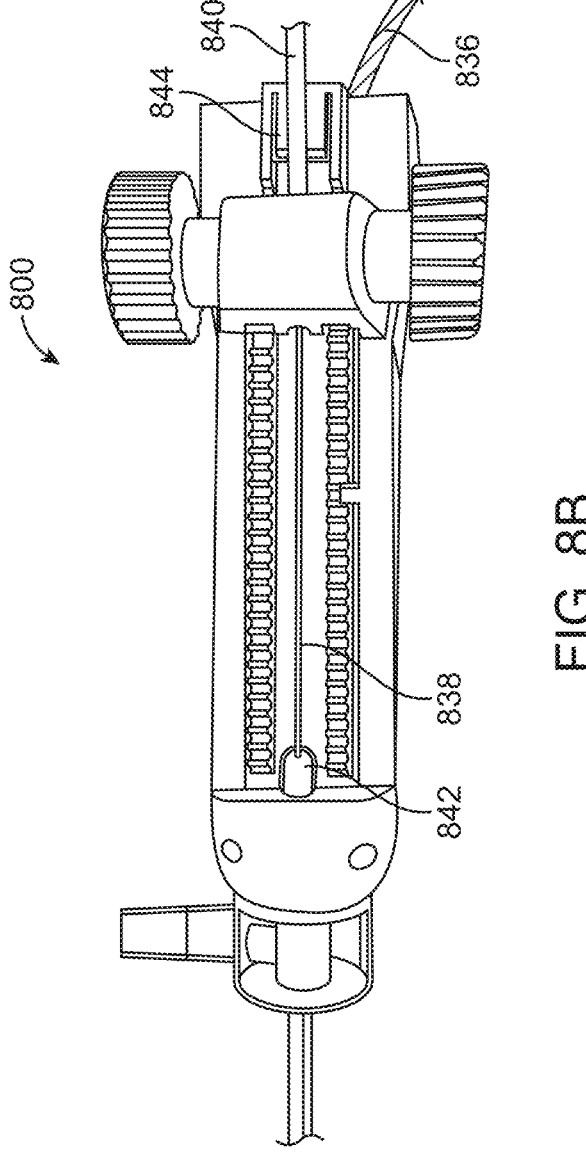
FIG. 8B shows components of the attachment device.

FIG. 8B shows components of the attachment device 800. The endoscope may comprise a stiff distal portion 838 and a flexible proximal portion 840. The stiff portion of the endoscope can extend from the endoscope carriage 828 to the distal tip of the endoscope. The stiff portion of the endoscope can extend through a seal 842 in order to seal and contain fluid from the surgical site. The stiff portion of the endoscope can be coupled to the carriage with an engagement structure on a proximal portion of the endoscope. The stiff portion of the endoscope can also be coupled to the coupling with a distal engagement structure located near the tip of the endoscope. The stiff portion of the endoscope extending between the carriage and the coupling provides proximal and distal motion of the coupling and the distal portion of the telescopic tube.

In many embodiments a flexible high pressure saline tube 836 extends to the attachment device to provide pressurized fluid from an external pump.

In many embodiments, the attachment device is configured for the user to remove components of the device such as the endoscope. For example, a carriage release 844 can be provided on the proximal end of the attachment device that allows the user to slide the carriage off of the rail proximally in order to remove the endoscope from the surgical site.

Figure 8C:
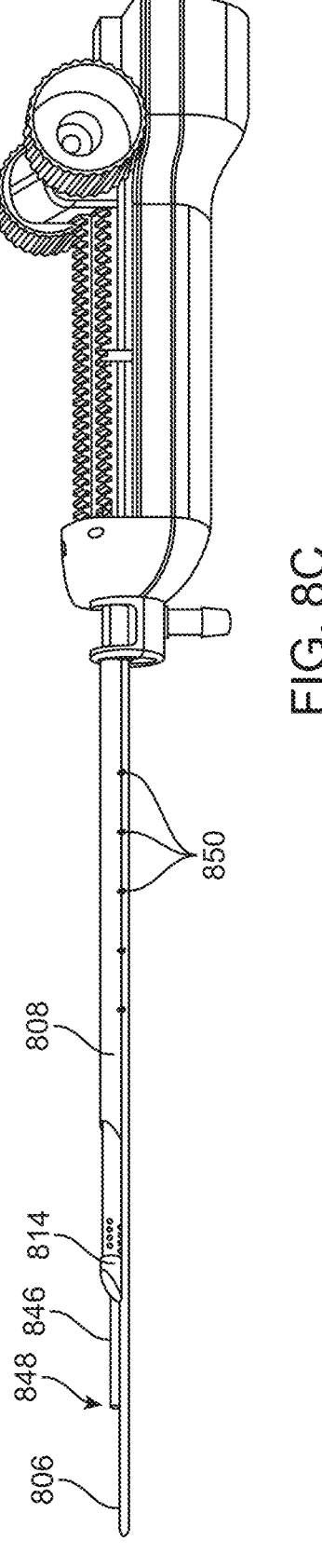
FIG. 8C shows components of the attachment device with the coupling in a partially retracted position and an elongate carrier comprising an energy source extending through the coupling toward the distal end of the elongate support.

FIG. 8C shows components of the attachment device 800 with the coupling 814 in a partially retracted position and an elongate carrier 846 comprising an energy source 848 extending through the coupling toward the distal end of the elongate support 806. In many embodiments, the endoscope tip can be at least partially retracted in order to view the treatment probe 846 in the support. The elongate carrier comprising the treatment probe can have an energy source located thereon to direct energy to a treatment site. The distal portion of the elongate tube 808 can be retracted within the proximal portion of the elongate tube in order to allow the coupling having the endoscope tip attached thereto to view the treatment site. The coupling can be retracted proximally with rotation of the knob to a proximal location, for example.

The elongate support 806 can be connected to the elongate tube 808 in one or more of many ways to add stiffness. For example, the elongate support can be welded to a proximal portion of the elongate tube at a plurality of locations 850 to add stiffness to the combination of the elongate support and the elongate tube.

The welded portion of the elongate tube can remain at a fixed position in relation to the elongate support when the distal portion of the elongate tube slides relative to the proximal fixed portion of the tube.

Figure 8D:
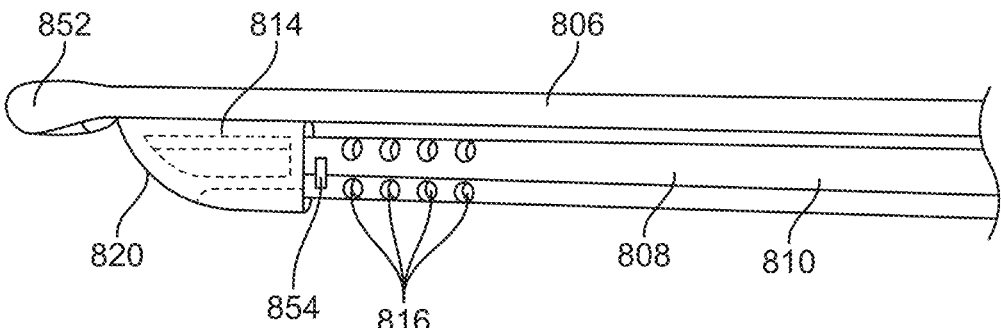
FIG. 8D shows distal portions of the elongate support and the elongate tube having the coupling mounted thereon.

FIG. 8D shows distal portions of the elongate support 806 and the elongate tube 808 having the coupling 814 mounted thereon. The elongate support may comprise a pressure reducing tip such as a rounded distal tip 852 in order to facilitate insertion along a surgical access path such as through the urethra. The inclined distal surface 820 of the coupling can facilitate insertion and urge tissue away from the elongate support. In many embodiments, the elongate support comprises a recess sized to receive a portion of the coupling such that the distal most tip of the coupling fits within the recess behind the pressure-reducing distal tip. The pressure-reducing distal tip can define an access path for the attachment device into the patient and the inclined distal surface of the coupling can follow the pressure-reducing tip and the tip of the coupling can follow a path of the pressure-reducing tip. This combination of the pressure-reducing tip and inclined distal surface can facilitate insertion.

The elongate tube 808 comprising a plurality of openings 816 can move with the coupling 814. The coupling to receive the distal tip of the endoscope can be configured in one or more of many ways to receive the endoscope tip, such as with a channel or slot that receives a protrusion on the endoscope and locks to the endoscope. The distal portion of the elongate telescopic tube may comprise an opening 854 to receive a fastener from the coupling. The fastener from the coupling extending through the opening of the tube can effectively lock the coupling to the distal end of the tube. The distal end 810 of the tube may comprise a plurality of irrigation openings 816. The plurality of irrigation openings can move with the endoscope tip in order to rinse and facilitate viewing with the endoscope tip. The movement of the irrigation openings generally directs fluid towards the surgical site such that the fluid can be directed. The irrigation openings that move with the endoscope tip have the advantage of rinsing the tip and providing fluid to increase visibility when the treatment probe tip is immersed in liquid, for example.

FIGS. 8E1 through 8E4 show the coupling 814 in accordance with embodiments. FIG. 8E1 shows a cross-sectional end view. FIG. 8E2 shows a cross-sectional side view. FIG. 8E3 shows a side view and FIG. 8E4 shows an end view. The coupling comprises a carrier channel 856 to receive the treatment probe on the carrier as described herein. The carrier channel is sized to allow the carrier comprising the treatment probe to slide proximally, distally and rotationally without interference from the coupling. The carrier channel may comprise a guide that facilitates alignment and placement and stabilizes the location of the distal end of the carrier comprising the energy source. The coupling comprises an endoscope channel 858 sized to receive the endoscope. The endoscope channel can be configured to receive the endoscope and an engagement structure of the endoscope and lock the engagement structure of the endoscope to the coupling.

With the side view shown in FIG. 8E2, the field of view 860 of the endoscope is shown. The field of view of the endoscope can be a field of view of a commercially available endoscope such as a 70° field of view, for example. The endoscope can view the surgical site, the elongate support and the treatment probe of the carrier from within the endoscope channel. In many embodiments, the inclined surface 820 of the distal end of the coupling is inclined with an angle so as to define the field of view along an upper portion of the field of view of the endoscope.

As shown in FIG. 8E3, the coupling 814 may comprise a slot 862 to receive a protrusion on the endoscope. The slot can be sized so as to allow the protrusion to enter the slot with rotation of the endoscope, for example. Although a slot is shown, the engagement structure of the coupling that receives the engagement structure on the distal end of the stiff portion of the endoscope can be configured in one or more of many ways such as with locking structures, threaded structures, hubs and threads, for example.

For example, the endoscope tip may comprise a leaf spring or a similar structure, configured to snap into a corresponding catching edge or lip disposed along at least a portion of an inner circumference of the coupling. Using such a mechanism, a user may lock the endoscope tip to the coupling by simply pushing the endoscope tip into the coupling until the leaf spring engages the catching edge. To allow uncoupling of the endoscope tip from the coupling, a portion of the inner circumference of the coupling may comprise a slanted edge configured to allow the leaf spring to slide out. To uncouple the endoscope tip from the coupling, the user may rotate the endoscope until the leaf spring is aligned with the slanted edge, and pull the endoscope out.

Also shown in FIG. 8E3 is a protrusion 855 that extends through the tube.

FIG. 8E4 shows approximate dimensions of the treatment probe carrier 846 and endoscope 866 with dashed lines in the carrier channel 856 and endoscope channel 858 respectively. The carrier channel and endoscope channel can be sized and spaced apart to provide a clearance gap 868 between the carrier and the endoscope. In many embodiments, the stiff distal tip of the endoscope comprises a protrusion 864 as described herein. The protrusion can extend a radial distance from the stiff distal portion to fit into the slot 862 and engage the coupling. In many embodiments, the protrusion is dimensioned to extend a distance greater than the gap in order to lock the coupling to the endoscope when the carrier probe comprising the energy source extends through the carrier channel. This configuration can facilitate assembly and disassembly of the coupling from the endoscope with the carrier removed, and provides locking of the coupling with the carrier inserted into the coupling, for example.

Figure 8F:
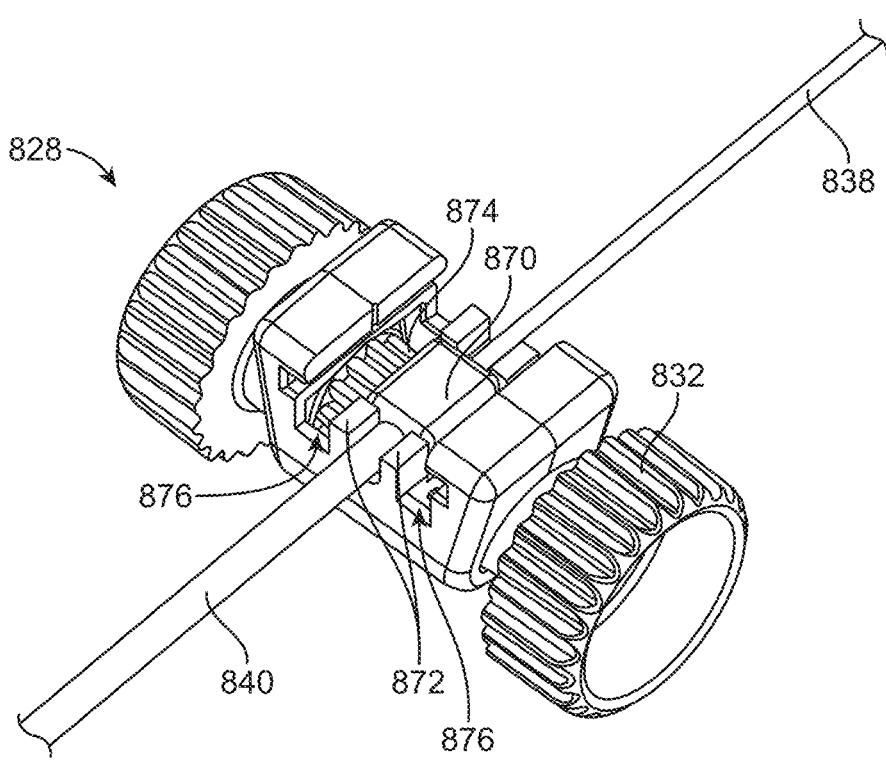
FIG. 8F shows an underside view of the carriage in accordance with embodiments.

FIG. 8F shows an underside view of the carriage 828 in accordance with embodiments. The underside view shows the stiff portion 838 of the endoscope and the flexible portion 840 of the endoscope coupled to the proximal engagement structure 870 of the endoscope. The proximal engagement structure of the endoscope fits within an engagement structure 872 of the carriage such that movement of the carriage proximally and distally moves the stiff portion of the endoscope in the engagement structure. The underside view of the carriage shows a pinion gear 874 which rotates with the knob 832. The pinion gear engages the rack as described herein. Also shown in the underside view is a slot 876 on each side of the carriage that receives a rail of the attachment device as described herein. The engagement structure 872 of the carriage may comprise a plurality of protrusions. For example, the plurality of protrusions can extend on a proximal side of the carriage and a distal side of the carriage in order to move the endoscope proximally and distally.

Figure 8G:
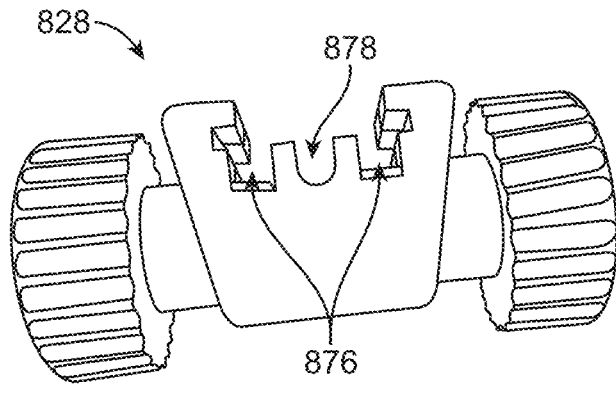
FIG. 8G shows an end view of the carriage in accordance with embodiments.

FIG. 8G shows an end view of the carriage 828 in accordance with embodiments. The carriage comprises a plurality of slots 876 sized to receive the rail of the attachment device. The carriage also comprises a channel 878 sized to receive the endoscope.

The carriage shown in FIGS. 8F and 8G may be configured to have a low profile, in order to facilitate user handling of the attachment device. For example, the carriage can be configured to have a housing with a relatively shorter height, and the knobs can be shaped and dimensioned to have a relatively smaller diameter and longer length (e.g., to facilitate gripping of the knob by a user).

Figure 8H:
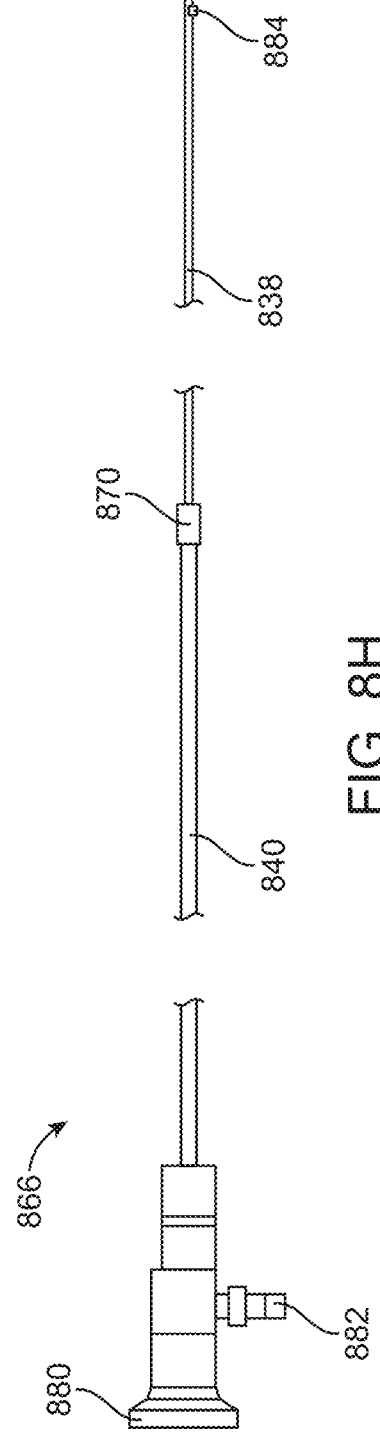
FIG. 8H shows an endoscope in isolation in accordance with embodiments.

FIG. 8H shows an endoscope 866 in isolation in accordance with embodiments. The endoscope comprises an eyepiece 880 that allows a user such as a surgeon to view the surgical site from the distal end of the endoscope, wherein the eyepiece is located on the proximal end of the endoscope. The endoscope comprises an illumination port 882 that allows a camera such as a high definition camera to be coupled to the endoscope. The endoscope comprises the proximal flexible portion 840 as described herein. The endoscope comprises a proximal engagement structure 870. The proximal engagement structure is located between the flexible proximal portion 838 of the endoscope and the stiff distal portion 840 of the endoscope. The endoscope comprises a distal engagement structure 884 as described herein.

FIG. 8I1 shows a side view of the endoscope 866. FIG. 8I2 shows a side view along section AA as in FIG. 8I1. FIG. 8I3 shows section BB of the endoscope of FIG. 8I1, wherein section BB comprises structures similar to those shown in section AA. FIG. 8I4 shows a top view of the endoscope as in FIG. 8I1. FIG. 8I5 shows a distal end of the endoscope as in FIG. 8I. The endoscope comprises the eyepiece 880, the illumination port 882, the flexible portion 840, the proximal engagement structure 870, the stiff distal portion 838 and the distal end 818 of the endoscope as described herein. FIGS. 8I2 and 8I3 show cross-sectional views of the endoscope and structures that provide a fixed alignment of the endoscope with respect to the engagement structures. For example, the flat surfaces shown along section AA and section BB correspond to a maximum of dimension across the proximal engagement structure. Having the proximal engagement structure in a fixed alignment with the endoscope can facilitate alignment and ensure an accurate reference frame when the endoscope is used. FIG. 8I4 in the top view shows the distal engagement structure 884 along section G. Detail G in FIG. 8I5 shows the distal engagement structure 884 extending as a protrusion 864 from the distal end.

In many embodiments, the proximal engagement structure comprises a reference structure such as a maximum dimension across that defines an orientation of the endoscope with respect to the attachment device. The maximum dimension across the proximal engagement structure informs the user or other person assembling the device of the reference frame of the endoscope with respect to the attachment device as described herein. The attachment device may comprise a reference frame for the treatment and surgery as described herein. For example, angular rotation of the treatment probe about an access can be made with respect to the attachment device and components of the attachment device such as encoders as described herein.

Figure 8J:
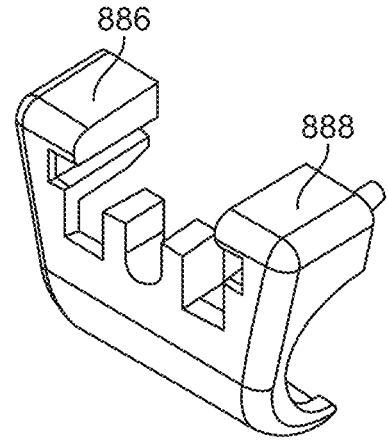
FIG. 8J shows a housing of the carriage as described herein.

FIG. 8J shows a housing 886 of the carriage as described herein. The housing of the carriage may comprise a single piece of injection-molded plastic, for example. A single piece can be provided in duplicate such as a pair of pieces of the single piece in order to allow assembly of the carriage housing. For example with reference to FIG. 8J, a second housing having the same shape as the first component 888 of the housing can be provided such that the two pieces snap together over the knob and axel and pinion gear as described herein so as to define the carriage.

Figure 8K:
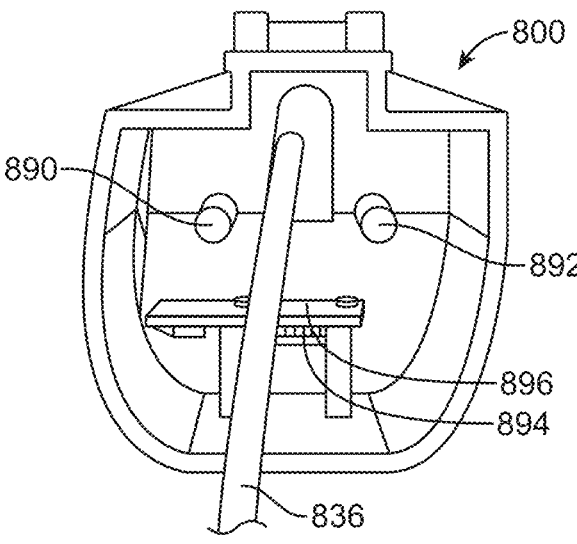
FIG. 8K shows an end view of the attachment device as described herein.

FIG. 8K shows an end view of the attachment device 800 as described herein. The attachment device comprises a plurality of rotatable connectors such as a first rotatable connector 890 and a second rotatable connector 892. A first rotatable connector determines an axial location of the energy source to treat the patient. A second rotatable connector determines an angular location of the energy source with respect to the axis. For example, the energy source may comprise a jewel mounted on a hypo tube in which an axial location of the jewel is determined with a first rotatable connector and an angle of the jewel with respect to the axis is determined with respect to a second rotatable connector. The first and second rotatable connectors can be used to control both the rotation and the axial location of the energy source as described herein. The attachment device comprising the handpiece may comprise an electrical connector 894. The electrical connector can connect to an electrical connector on the arm. The electrical connector can be used to transmit signals to and from the attachment device. The signals transmitted with the electrical connector can comprise electrical signals from the encoder to a controller away from the attachment device. The attachment device may comprise a printed circuit board 896 having the electrical connector disposed thereon in order to connect the attachment device to the arm. The electrical connector may comprise standard connectors known in the industry. The printed circuit board may comprise circuitry 898 of the handpiece. The circuitry may comprise a processor for example in a nonvolatile memory configured to record aspects of the treatment such as the treatment table as described herein and machine parameters such as flow rate and pressure for example. The high pressure saline tube 836 may comprise a flexible tube extending into the proximal end of the handpiece.

Figure 8L:
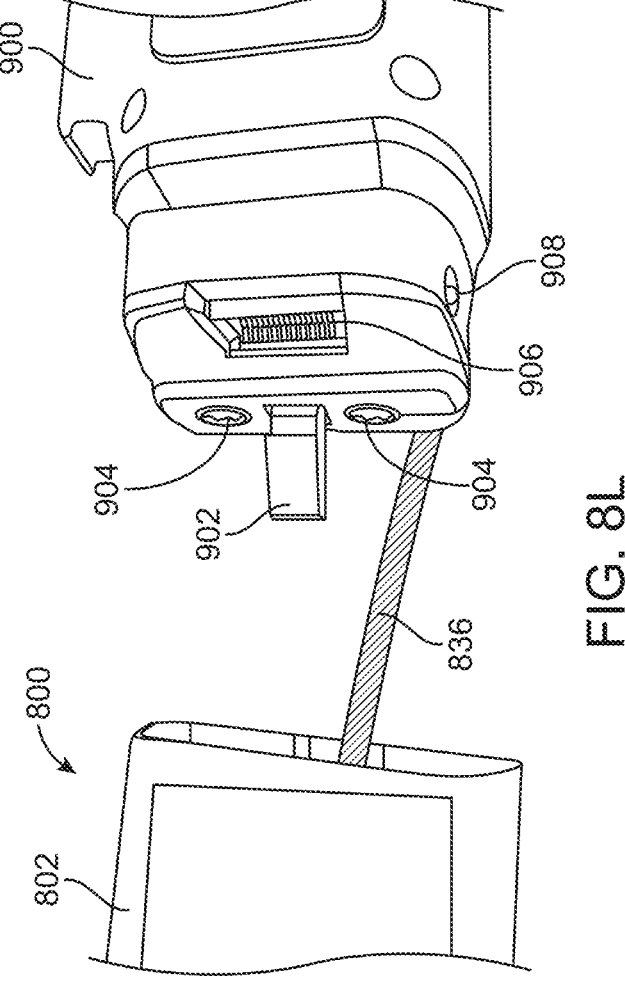
FIG. 8L shows components of the arm configured to couple to the attachment device.

FIG. 8L shows components of the arm 900 configured to couple to the attachment device 800. The arm may comprise a locking mechanical connector 902 configured to couple to the attachment device and lock the attachment device in place. The arm may comprise a plurality of rotatable connectors 904 configured to engage the rotatable connectors of the attachment device. The arm may comprise an electrical connector 906 configured to connect to the attachment device. Although an electrical connector is shown, other connectors can be used such as fiber optics or optical connectors, for example. The arm may also comprise a contact sensor 908 that senses contact of the attachment device with the arm.

The circuitry of the arm and the attachment device can be configured in one or more of many ways to facilitate connection of the attachment device to the arm. Alternatively or in combination, the attachment device can be configured to comprise a consumable device such as a single use device. In many embodiments, the contact sensor is coupled to circuitry configured to rotate the rotatable connectors on the arm in response to the contact sensor engaging the attachment device. When the contact sensor engages the attachment device, the rotatable connectors rotate back and forth through a predetermined range of motion in order to allow a mating connection of the rotatable connector on the arm with the rotatable connector on the attachment device. In many embodiments, the rotatable connector on the arm comprises a plurality of hexagonal sockets and the attachment device comprises a plurality of hexagonal cross-section protrusions to engage the sockets of the arm. Alternatively, the sockets and protrusions can be reversed such that the sockets are provided on the attachment device and the protrusions are provided on the arm or combinations thereof. Once the rotatable connector engages the rotatable connector of the attachment device, the circuitry within the arm can detect movement with sensors located on the attachment device and stop rotation of the rotatable connectors upon completion of the coupling of the arm to the attachment device.

Figure 8M:
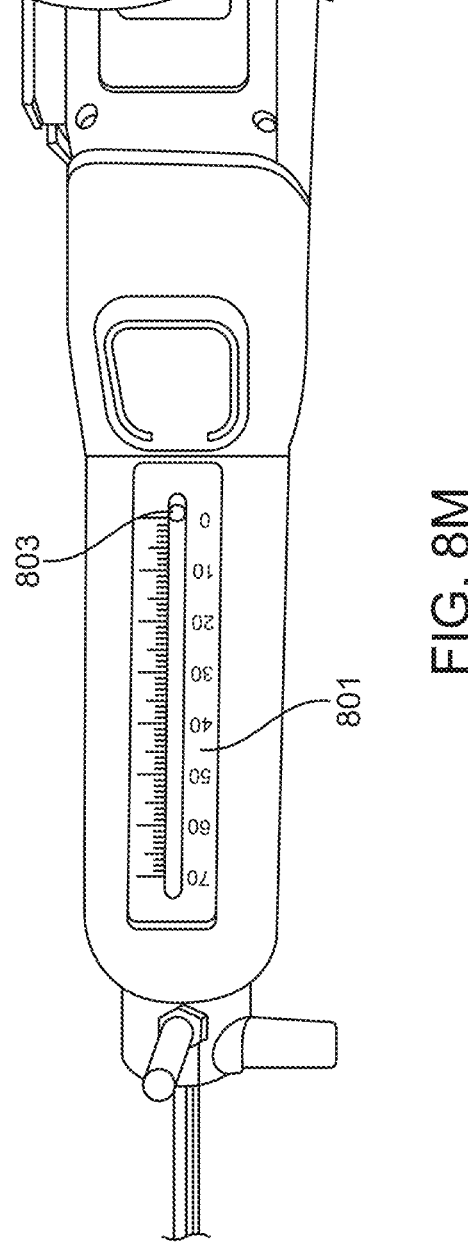
FIG. 8M shows a view of an upper side of the attachment device in accordance with embodiments.

FIG. 8M shows a view of an upper side of the attachment device 800 in accordance with embodiments. The upper side of the attachment device can be located opposite the side having the rack and pinion, for example. The attachment device may comprise a measurement scale 801 and an indicator 803 such as an LED to indicate the location of the energy source on the carrier probe comprising the treatment probe. In many embodiments, the indicator is mounted on the internal linkage that moves axially in order to treat the patient. This LED indicator on the probe can inform the user the location of the treatment probe. The measurement scale may comprise one or more of many units and generally comprises a one-to-one scaling with motion of the probe tip.

The measurement scale can be in units such as centimeters, millimeters or other units of length, for example.

Figure 8N:
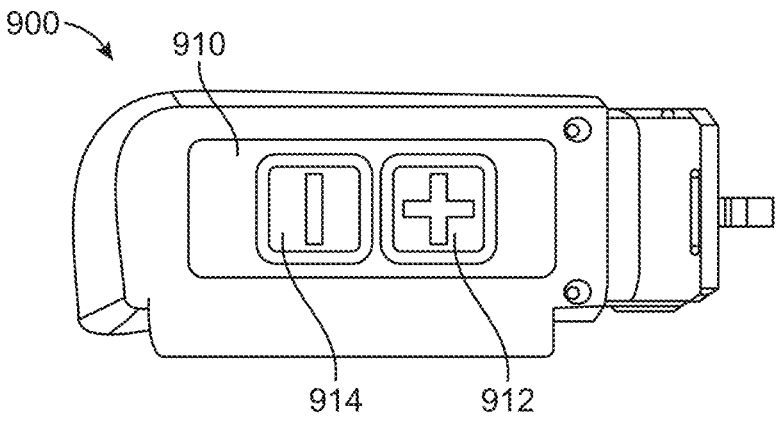
FIG. 8N shows a component of the arm in accordance with embodiments.

FIG. 8N shows a component of the arm 900 in accordance with embodiments. The component of the arm may comprise an attachable component of the arm comprising a user input device 910. The user input device may comprise a first input 912 to increase an intensity of the energy source and a second input 914 to decrease an intensity of the energy source. For example, when the energy source comprises a liquid stream, the increase in the intensity of the energy source may comprise an increased flow rate of the energy source and/or an increased pressure of the energy source. The decreased intensity of the energy source may comprise a decreased flow rate or a decreased pressure of the energy source and combinations thereof, for example.

FIG. 8O2 and FIG. 8O1 show internal structures of the arm components shown in FIG. 8N. FIG. 8O1 shows circuitry 916 of a lower portion of the component. The circuitry can be coupled to the connector 906 that couples to the attachment device. The circuitry may comprise circuitry as described herein and may comprise one or more of many known circuit components such as a processor, memory, such as random access memory, and a gate array, such as a field programmable gate array, for example. The circuitry may comprise one or more of many known components used to control motors. FIG. 8O2 shows motors 918 of the arm in accordance with embodiments. The motors may comprise known motor components capable of driving surgical instruments. The motors may comprise shafts extending to protrusions of the rotatable connector as described herein. The motors can engage the attachment device when the attachment device is connected to the arm.

The circuitry coupled to the connector as shown in FIG. 8O1 can be used to control the motors in order to position the energy source at an intended axial location and rotation angle about the axis. The circuitry may comprise one or more instructions to transmit signals to encoders located on the attachment device in order to measure an angular location of the probe rotated about the axis. The rotation of the energy source about the axis can be fed back to the circuitry and the circuitry can drive the energy source to a plurality of locations in accordance with instructions of a treatment table as described herein. By locating the circuitry and the motors at a reusable location on the arm, the cost and complexity of the attachment device comprising the handpiece can be decreased substantially.

Figure 8P:
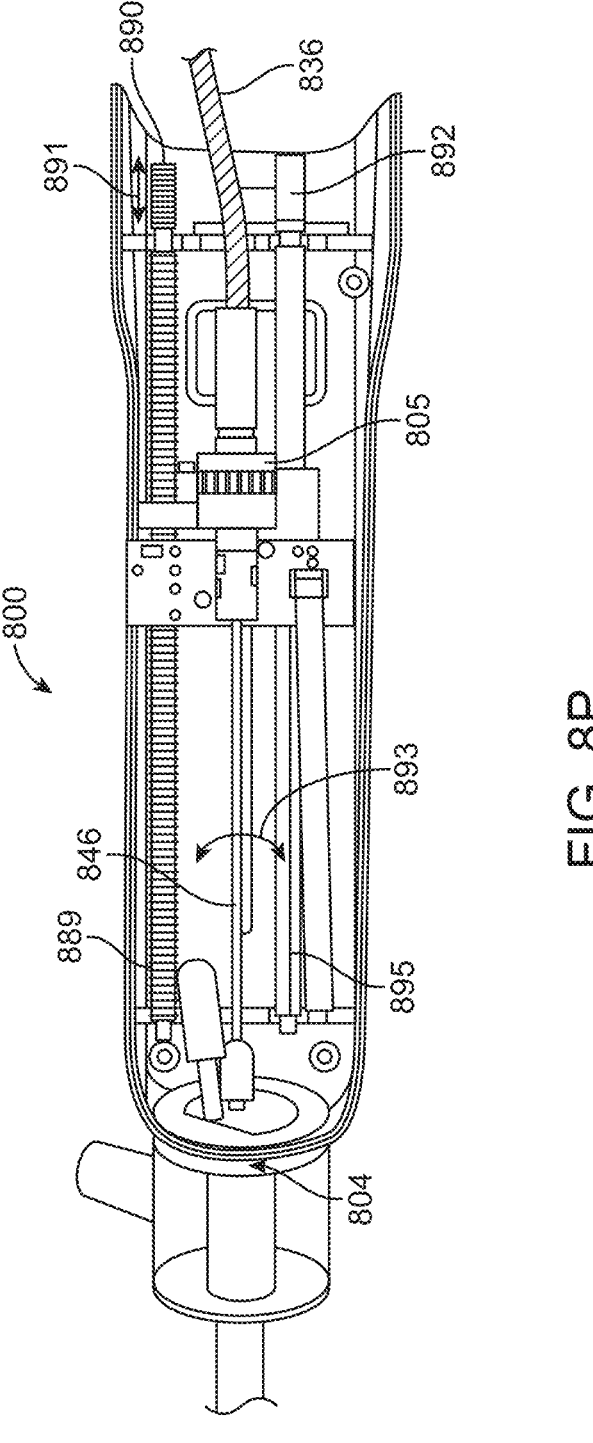
FIG. 8P shows the linkage of the attachment device in accordance with embodiments.

FIG. 8P shows the linkage 804 of the attachment device 800 in accordance with embodiments. The linkage shown in FIG. 8P may comprise one or more components configured to direct the energy source to a desired location and angle on the distal end of the carrier 846 comprising the treatment probe. The carrier that carries the energy source near the distal end is coupled to the linkage so as to control the position and angle of the energy source on the end of the carrier. The carrier may comprise a hypo tube, for example, and the energy source may comprise one or more of many energy sources as described herein. For example, the energy source may comprise a nozzle formed in a material comprising a jewel. The jewel on the hypo tube can receive high pressure fluid from the cable 836. The carrier is connected to a flexible conduit that receives energy with a medium such as high-pressured saline along a flexible high pressure tube. The carrier connects to the linkage such that the carrier translates and rotates in response to commands from the circuitry.

The linkage comprises a first rotating connector 890 to control a Z axis position along the elongate axis of the carrier and a second rotatable connector 892 to control an angle of the energy source with respect to the elongate axis. The first rotatable connector 890 can be rotatably connected to a plurality of threads 889. Rotation of the threads can drive the linkage proximally and distally as indicated with arrow 891. The threads when rotated can induce the carrier 846 to move proximally and distally as shown. As the carrier moves proximally and distally, the second rotatable connector 892 can slide along an elongate structure such as a hexagonal structure 895. The sliding of the carrier in the axial direction can be provided for a range of treatment, for example, up to about 7 millimeters. The second rotatable connector 892 can be rotated so as to induce rotation of the carrier. For example, rotation of the second rotatable connector can cause the angular rotation of the carrier as shown with rotational arrow 893. Rotation of the second rotatable connector can rotate a gear 805 of the linkage that is coupled to the carrier 846. The gear of the linkage can be concentric with the carrier so as to induce rotation of the carrier about an elongate axis of the carrier. The second rotatable connector can comprise a second gear that is concentric to the rotatable connector in order to induce rotation of the gear that is concentric with the carrier. The linkage may comprise an idler gear, for example, between the first gear and the second gear in order to induce angular rotation of the energy source with respect to the elongate axis of the carrier.

Figure 8Q:
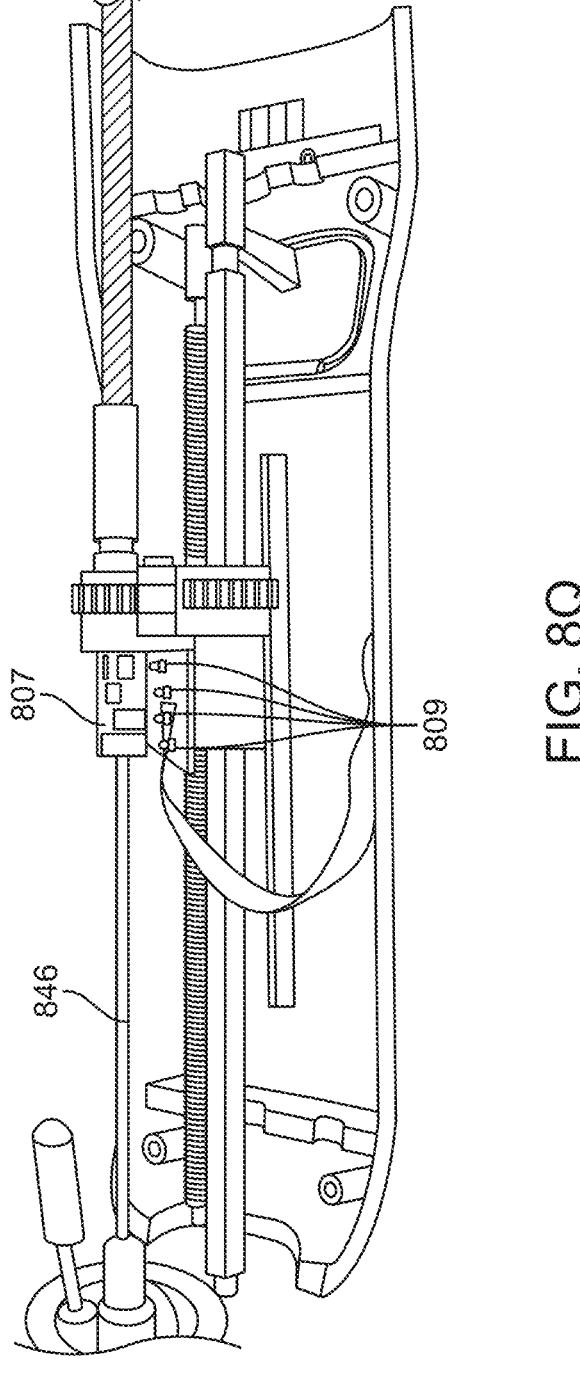
FIG. 8Q shows an encoder mounted on the proximal end of the carrier.

FIG. 8Q shows an encoder 807 mounted on the proximal end of the carrier 846. The encoder on the proximal end of the carrier can allow accurate rotational positioning of the angle of the energy source. The carrier can be rotated to a target position in response to signals measured from the encoder. The encoder on the proximal end of the carrier may comprise one or more of many known encoders. In many embodiments, the encoder comprises a Gray encoder configured to provide quadrature measurements. The encoder can be provided on the face of the carrier, for example, with an annular structure extending from the carrier so as to provide an accurate surface to affix the encoder to. Also, the photo detectors 809 can be arranged in a line extending along the direction of the carrier probe axis. This can facilitate measurements of the angle of the energy source and can allow the detectors to lie on a plane of a printed circuit board. The encoder can extend on a face of the carrier probe and the carrier probe may comprise a removable carrier treatment probe. Removable carrier treatment probe can extend into the seal as described herein. In many embodiments, the encoder comprises an alignment structure that can be aligned with the energy source carried on the distal tip of the probe to ensure accurate alignment during manufacturing. For example, the encoder may comprise a plurality of edge transitions in which each edge extends in an axial direction. One or more of the edges can be preconfigured so as to align with an angle of the energy source extending from the elongate axis of the probe. For example, the energy source can extend in a radial direction from the axis at the same angle as the edge extends radially from the probe or is located along an angle extending radially from the probe.

FIG. 8R1 shows an encoder 807 in accordance with embodiments. As shown with the encoder, each of the edges 811 corresponds to an angular reference with respect to the probe. For example, a zero degree reference 813 is shown. The zero degree reference is aligned with the energy source extending from the distal end of the carrier.

FIG. 8R2 shows a table 815 showing coordinate references for different transitions measured with a plurality of photo detectors. These positions can give an absolute position of the probe within a certain range. The circuitry as described herein can be configured to interpolate within the position shown in FIG. 8R2. The interpolation can be performed in one or more of many ways. For example, the motors may comprise stepper motors to provide interpolation. Alternatively, the motors may comprise encoders within the motors that can be used to provide the interpolation.

White regions of the table 815 correspond to the steel tube portions of the encoder, while black regions correspond to the black plastic tube portions of the encoder. The steel tube and the black plastic tube can form a plurality of rows distributed along the longitudinal axis of the encoder, each row extending about the circumference of the encoder. Each row can be aligned with a photodetector. For each photodetector A (distal), B, C, and D (proximal), rotational positions of the encoder corresponding to the white regions can correspond to an "on" or "1" binary code, whereas rotational positions of the encoder corresponding to the black regions can correspond to an "off" or "0" binary code.

The configuration of the encoder and the photodetectors in FIGS. 8Q, 8R1, and 8R2 is provided by way of example only, and many other configurations are possible. For example, while FIGS. 8Q, 8R1, and 8R2 show an encoder comprising 4 rows with each row aligned with one of 4 photodetectors, an encoder may have any number of rows aligned with any number of photodetectors in any appropriate configuration. The encoder may comprise one or more additional rows and additional photodetectors aligned with each additional encoder row, to increase the resolution of the encoder and thereby provide more finely tunable positional adjustment of the motors and hence the carrier.

Figure 8S:
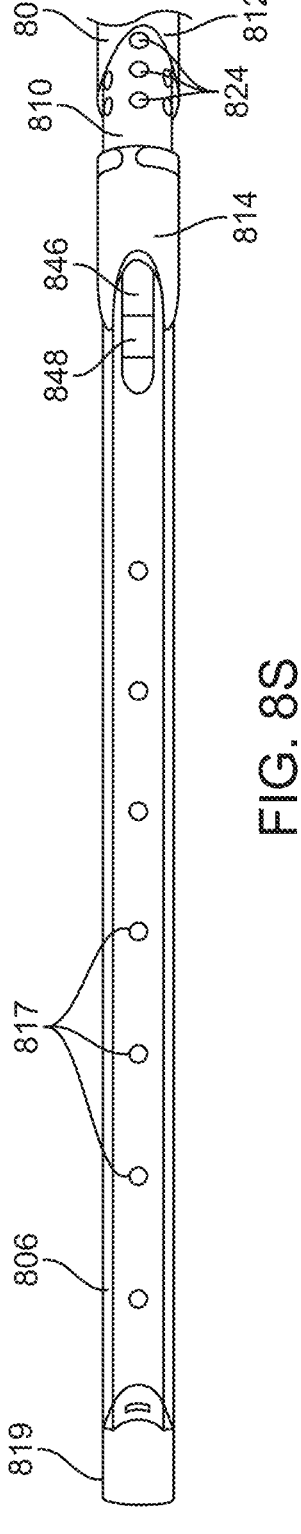
FIG. 8S shows aspiration ports on the distal end of the support in accordance with embodiments.

FIG. 8S shows aspiration ports 817 on the distal end 819 of the support 806 in accordance with embodiments. The distal end of the support comprises a plurality of ports 817 to aspirate material from the surgical site. The plurality of ports can be sized to receive tissue resected with the energy source 848. The ports can be positioned at predetermined locations so as to provide a visual guide to the user. For example, the aspiration ports can be located at one centimeter intervals such that the user can readily determine the size and location of tissue at the target site. The user can also evaluate the accuracy and verify the accuracy of the probe during use, for example. The support may comprise a plurality of ports in number from two to about 10, for example. The plurality of ports can be located on an underside of the support facing the carrier 846. The concave shape of the support can improve alignment and provide a space to receive the probe. The aspiration ports on the distal end of the support can be fluidically coupled to the aspiration port (826 in FIG. 8A) on the proximal end of the support near the hub with a channel extending from the port to the plurality of ports, for example. The carrier of the energy source can slide toward the distal end of the support during treatment. The ports can provide a reference structure to determine the location of the carrier with respect to the energy source and can be helpful during treatment to facilitate alignment. The plurality of ports on the distal end of the support can be seen with ultrasound, for example, and can be seen with the endoscope having the field of view as described herein, for example. The plurality of ports can be located between the ball-shaped portion on the distal end and the fixed portion of the tube. As described herein, the carrier probe can be advanced to the distal end of the support and retracted. As shown in FIG. 8S, the carrier of the energy source is shown in a retracted position. The coupling structure 814 is also shown retracted that couples the endoscope to the elongate tube 808. The proximal portion 812 of the tube is shown with the distal portion 810 of the tube having been received therein such that a portion of the irrigation ports 824 is covered with a proximal portion of the tube. The coupling 814 as described herein can be used to advance the elongate tube and the endoscope as described herein. The carrier comprising the energy source can be moved independently of the endoscope in the tube and the coupling, for example. In at least some embodiments, this independent motion can be helpful for treatment. Alternatively or in combination, the coupling can be positioned over the energy source to act as a shield for users of the system from the energy source. For example, when the system is initially set up, the coupling can be slid over the energy source in order to block the energy source. In many embodiments, the coupling comprises sufficient mechanical strength to withstand the energy source and the energy source is configured to resect tissue and also not to destroy the coupling when the coupling is positioned over the energy source.

Figure 8T:
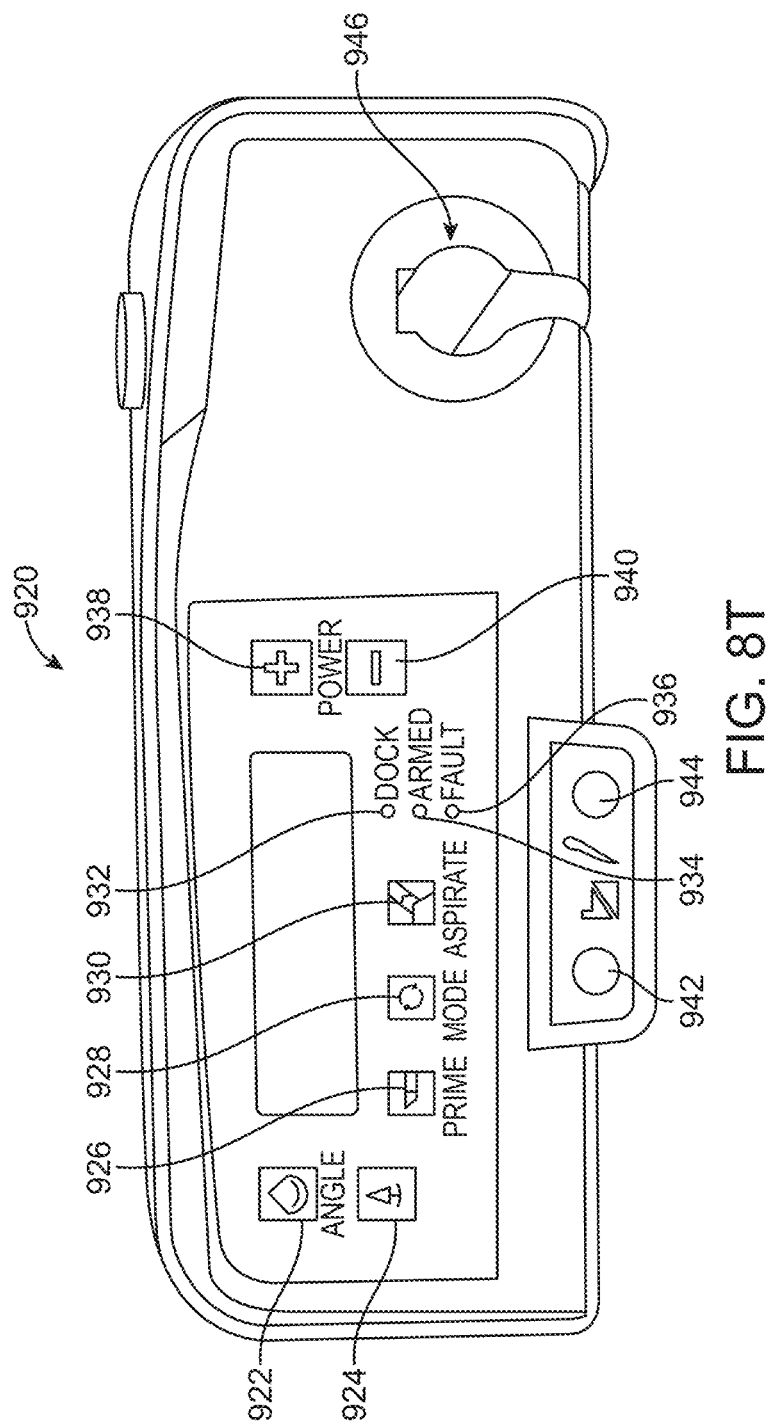
FIG. 8T shows a console in accordance with embodiments.

FIG. 8T shows a console 920 in accordance with embodiments. The console comprises a plurality of inputs and a plurality of outputs of a user interface that allows the user to program the system for treatment. The console comprises an angle input 922 to increase an angle and a second angle input 924 to decrease an angle. The console comprises a prime input 926 to prime a pump. The console comprises a mode input 928 to set a mode. The console comprises an aspiration input 930 to aspirate. The console comprises outputs such as a dock configuration 932, an arm state 934 and a fault state 936. The power can be increased or decreased to the energy source as shown with the plus 938 and the minus 940. Inputs for a foot pedal 942 and a hand control 944 are shown. The foot pedal may comprise a standard commercially available foot pedal and the hand control may comprise a plus and minus control on the arm as described herein. The high pressure tube can be attached to a channel or connector 946 coupled to a high pressure pump.

Figure 9A:
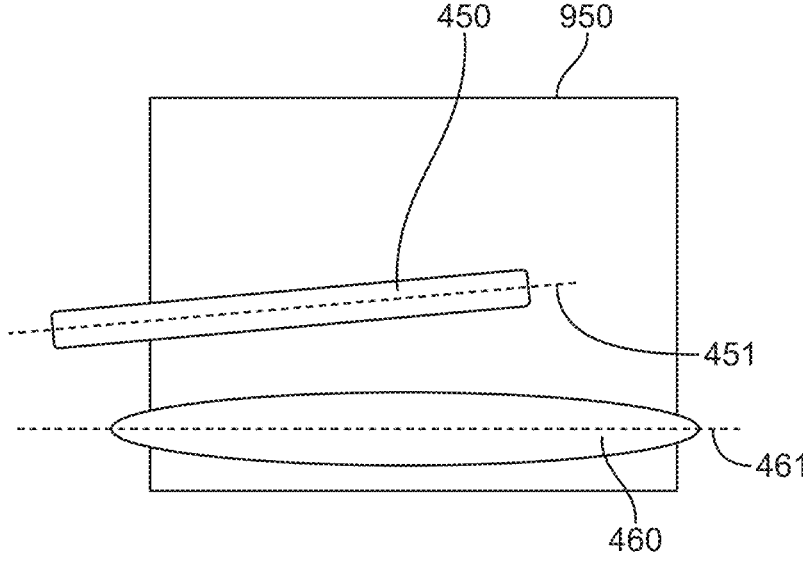
FIGS. 9A and 9B show side and top views, respectively, of alignment of a treatment probe axis with a sagittal plane of an imaging probe, in accordance with embodiments.
Figure 9B:
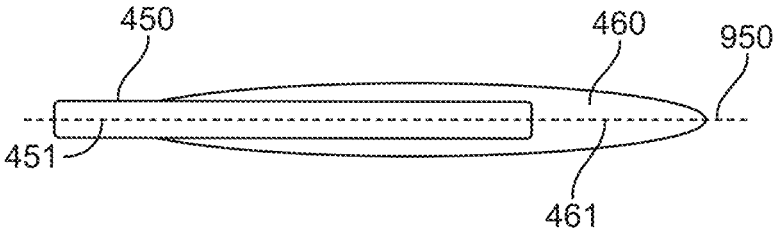

FIGS. 9A and 9B show side and top views, respectively, of alignment of a treatment probe axis with a sagittal plane of an imaging probe. FIG. 9A shows a treatment probe 450 that is inclined relative to an imaging probe 460. The imaging probe comprises an elongate axis 461 that provides a reference for the images. In many embodiments, the imaging probe comprises an elongate axis. The imaging probe may comprise an ultrasound probe having an elongate axis that at least partially defines a sagittal image plane 950. In many embodiments, the imaging probe comprises a sagittal image field of view, and the treatment probe 450 is substantially aligned with the sagittal plane of the imaging probe when the treatment probe is within the field of view of the sagittal image.

Although reference is made herein to a trans-rectal ultrasound (TRUS) imaging probe, the imaging probe may comprise one or more of many known probes such a non-TRUS probe, an ultrasound probe, a magnetic resonance probe, and endoscope or fluoroscopy, for example.

The user can use images of the treatment probe obtained with the imaging probe to align the treatment probe with the imaging probe. In axial mode, the treatment probe can appear distorted when the imaging probe is not sufficiently aligned with the treatment probe. The distortion of the treatment probe can depend on the cross-sectional shape of the treatment probe. For example, a disc shaped cross-sectional profile may appear as a distorted crescent shape in axial mode. In sagittal imaging mode, only a portion of the elongate probe extending through the sagittal field of view will appear in the image. The user can be prompted to align the probes until sufficient alignment is obtained in order to view the treatment probe, for example with inhibited distortion of the treatment probe in the axial mode and with a view of the elongate treatment probe along a substantial axial distance of the probe, e.g. 5 cm, in the sagittal image.

In many embodiments, as shown in FIG. 9B, the elongate axis 451 of the elongate treatment probe 450 is substantially aligned with the sagittal image plane 950 when a substantial portion of the elongate treatment probe is visible in the sagittal image, e.g. 5 mm.

Figures 9C, 9D:
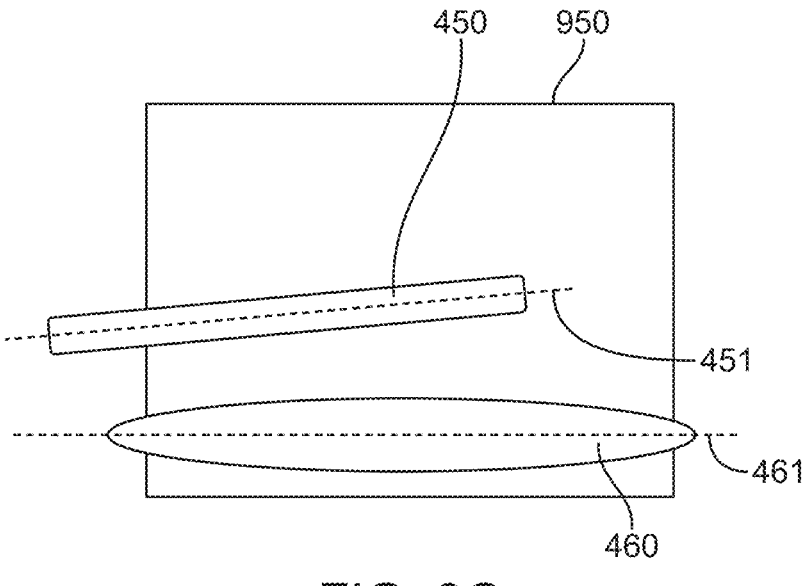
FIGS. 9C and 9D show side and to views, respectively, of a treatment probe traversing a sagittal image plane field of view, in accordance with embodiments.

FIGS. 9C and 9D show side and top views, respectively, of a treatment probe 450 traversing a sagittal image plane 950 field of view. The user can be prompted to improve alignment to a configuration similar to FIGS. 9A and 9B, for example.

There can be residual alignment errors corrected with software instructions of the processor in response to images of the treatment probe measured with the imaging probe. In many embodiments, the elongate axis of the treatment probe can appear rotated in the images. The system software can be configured to measure the rotation and rotate the images. For example, users can be trained to see sagittal images in which the axis of the imaging probe is used as a reference. To plan treatments, however, the users may better visualize the treatment when the elongate axis of treatment probe appears horizontally on the user screen, or vertically, for example. In many embodiments, the software measures an angle of rotation of the treatment probe in the image such as a TRUS image and rotates the image in response to the rotation of the treatment probe. For example, the system software may measure an angle of one degree of rotation and rotate the image accordingly such that the rotation angle appears to be zero degrees to the user.

Figure 10A:
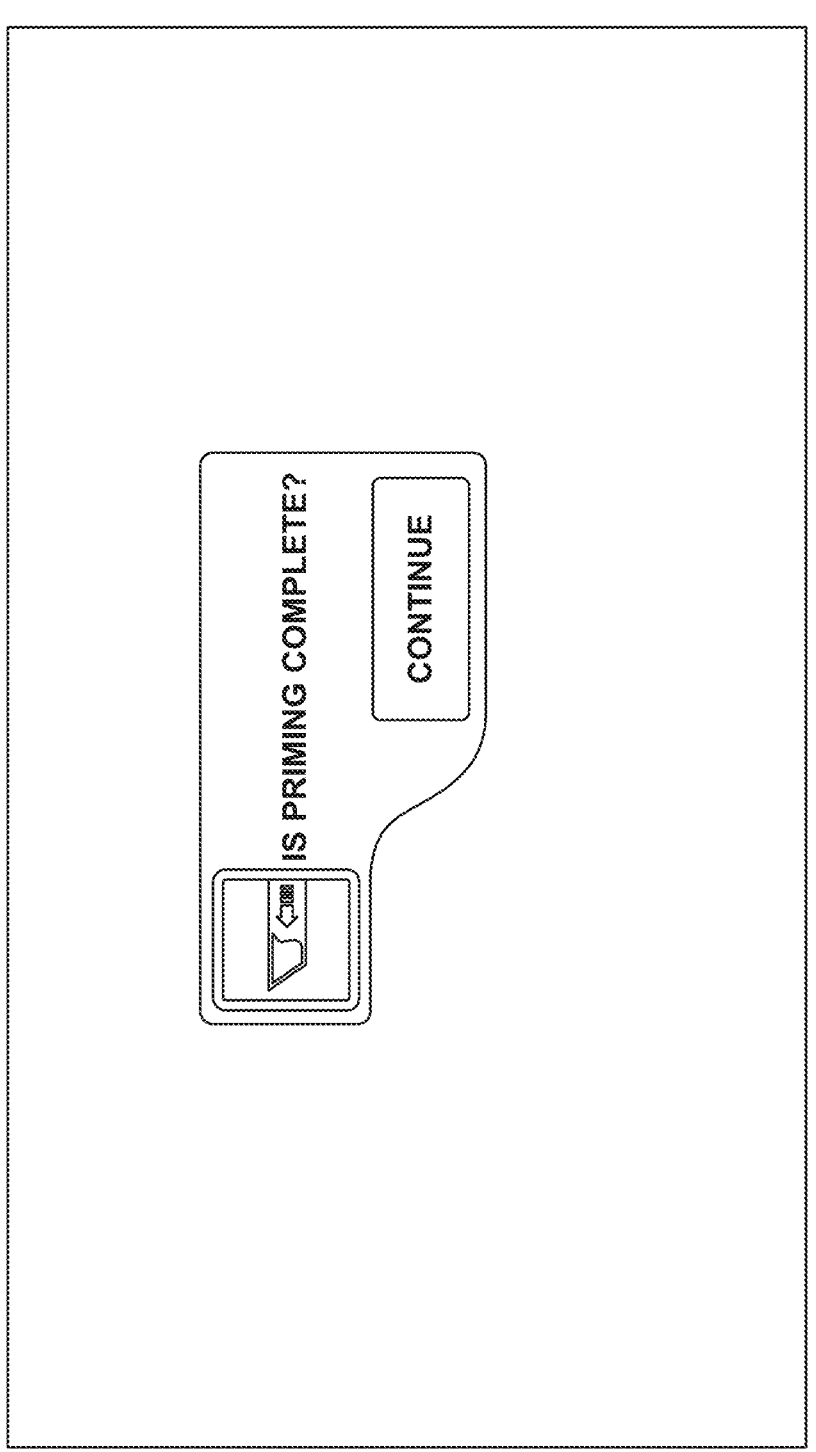
FIGS. 10A-10T show treatment screens of an apparatus, in accordance with embodiments.

FIGS. 10A-TOT show treatment screens of an apparatus, in accordance with embodiments.

FIG. 10A shows a priming verification screen in accordance with embodiments. The priming verification screen comprises a user input for the user to hit a continue button upon completion of the priming. The priming is performed in order to prime the pump. It can be used to provide the energy source such as the fluid stream. While the reference is made to a pump, the energy source could comprise another energy source or an alternative energy source such as an electrical energy source for example. Upon completion of the priming, the user hits continue.

Figure 10B:
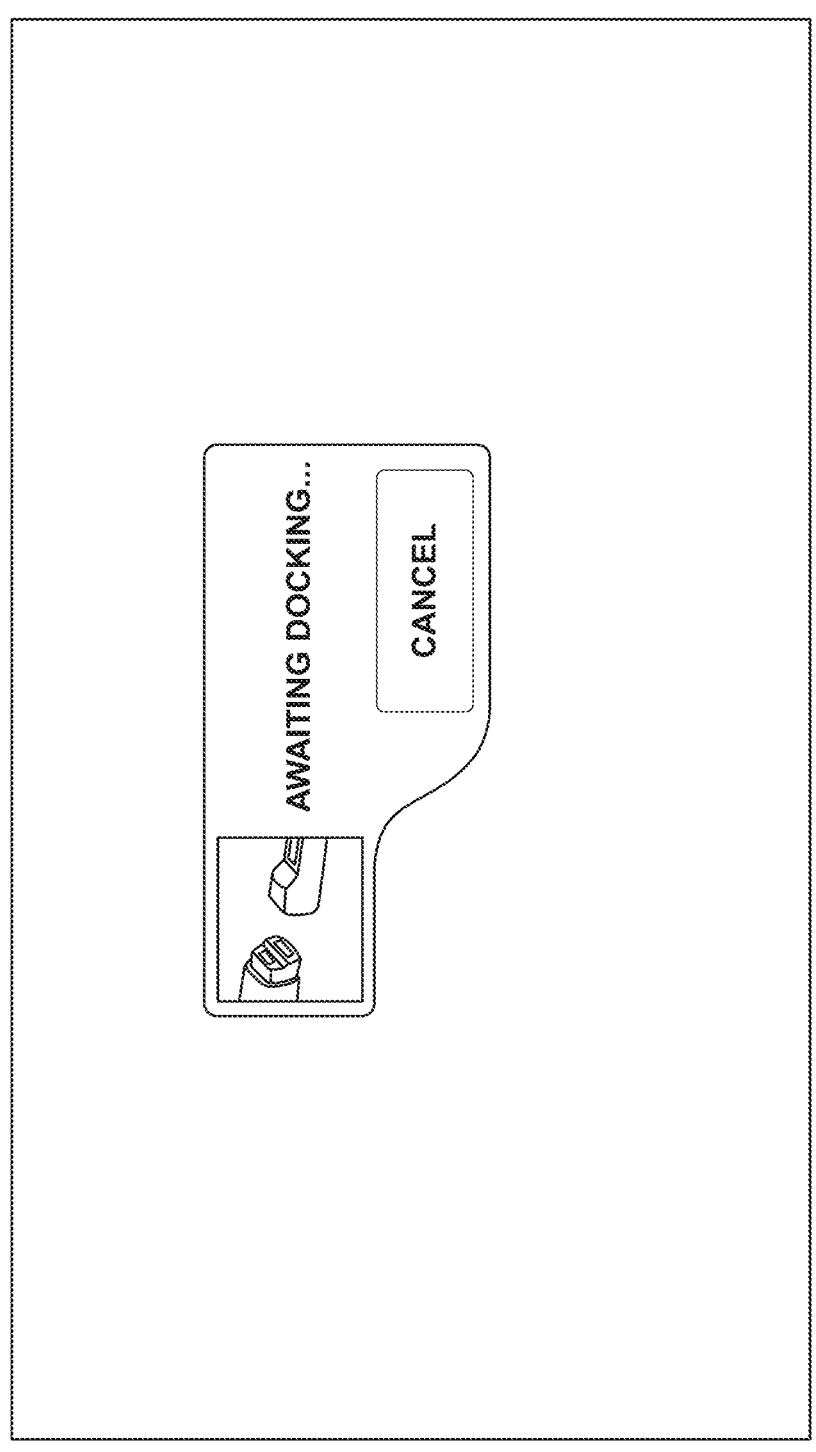

FIG. 10B shows an awaiting docking screen in accordance with embodiments. With FIG. 10B, the user is prompted to dock the system. The system can be docked by placing an attachment onto the arm as described herein. Once the attachment has been docked to the arm, the system automatically advances to the next step.

In many embodiments during the docking step, rotating couplings of the arm are provided in order to align the couplings of the arm with the attachment comprising the hand pieces described herein.

Figure 10C:
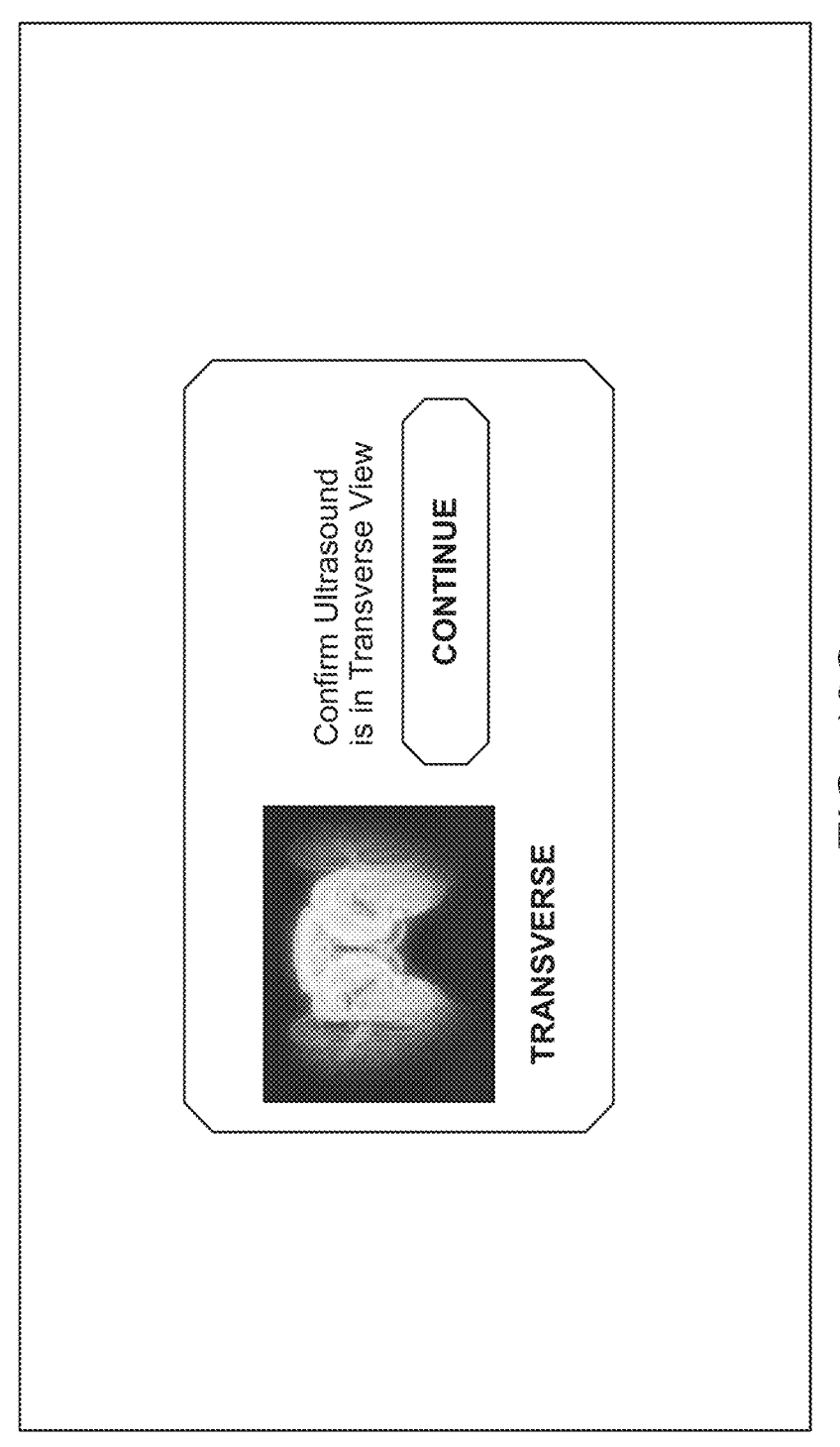

FIG. 10C shows a prompt for the user to confirm that the ultrasound is in transverse view. The screen can provide an ultrasound image of a transverse view in order to orient the user and confirm that the ultrasound probe is in a proper transverse view. Once the user has looked at the ultrasound system and confirmed that the ultrasound is in transverse view, the screen of the user interface provides a continue button for the user to provide input. Upon inputting continue, the user is prompted with the next screen.

Figure 10D:
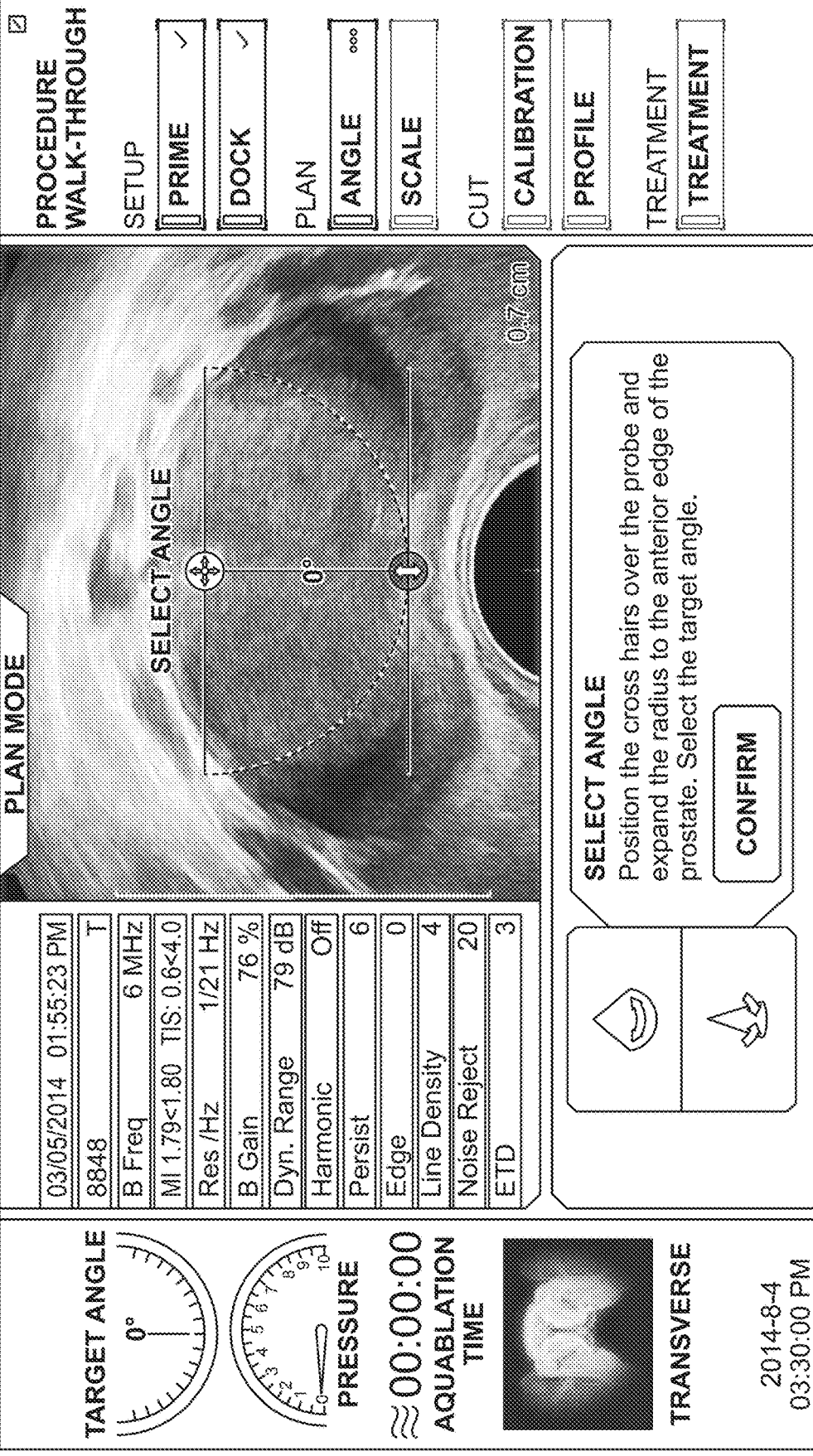

FIG. 10D shows an angle select input screen. The select angle input screen allows the user to select a treatment angle. The input screen comprises a plurality of icons; the first icon showing an increased angle, and the second icon showing a decreased angle. The user uses an input device such as a cursor and a mouse to click on the appropriate icon to increase the angle. For example, if the user desires to increase the angle, the user clicks on the icon comprising the outwardly extending arrows in order to increase the treatment angle. Once a treatment angle has been selected, the user can input confirm by hitting the confirm button. Selecting the angle in the transverse view allows the user to adjust the treatment angle to the patient anatomy. The treatment angle can be within a range from about 1 degree to 180 degrees for example. In many embodiments, the treatment angle is within a range from about 10 degrees to about 170 degrees.

Figure 10E:
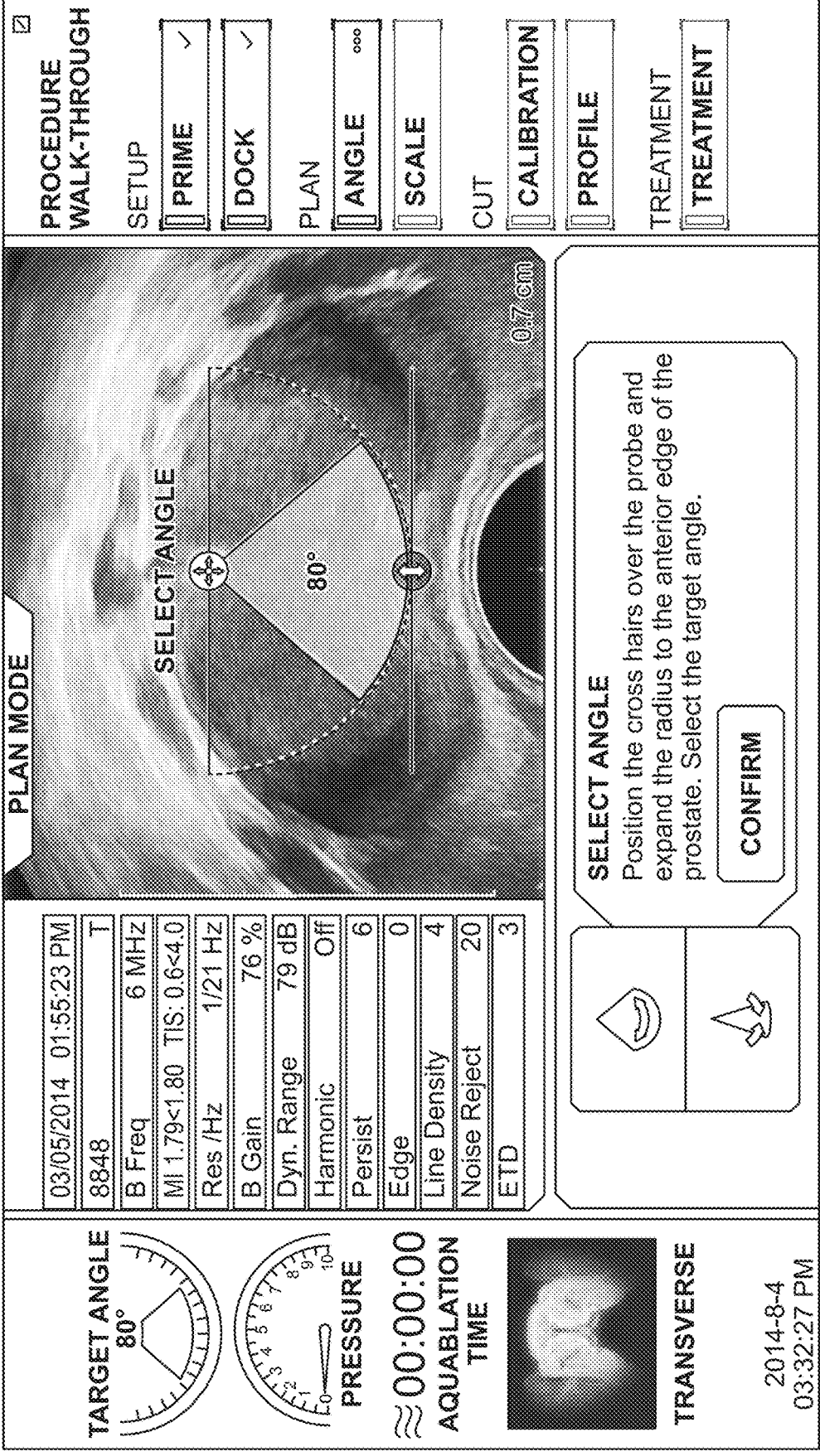

FIG. 10E shows an angle selected in accordance with embodiment. In FIG. 10E, a selected angle of 80 degrees is shown for example. Once the user has selected a desired angle, the user can hit the confirm button to move onto the next user input screen.

Figure 10F:
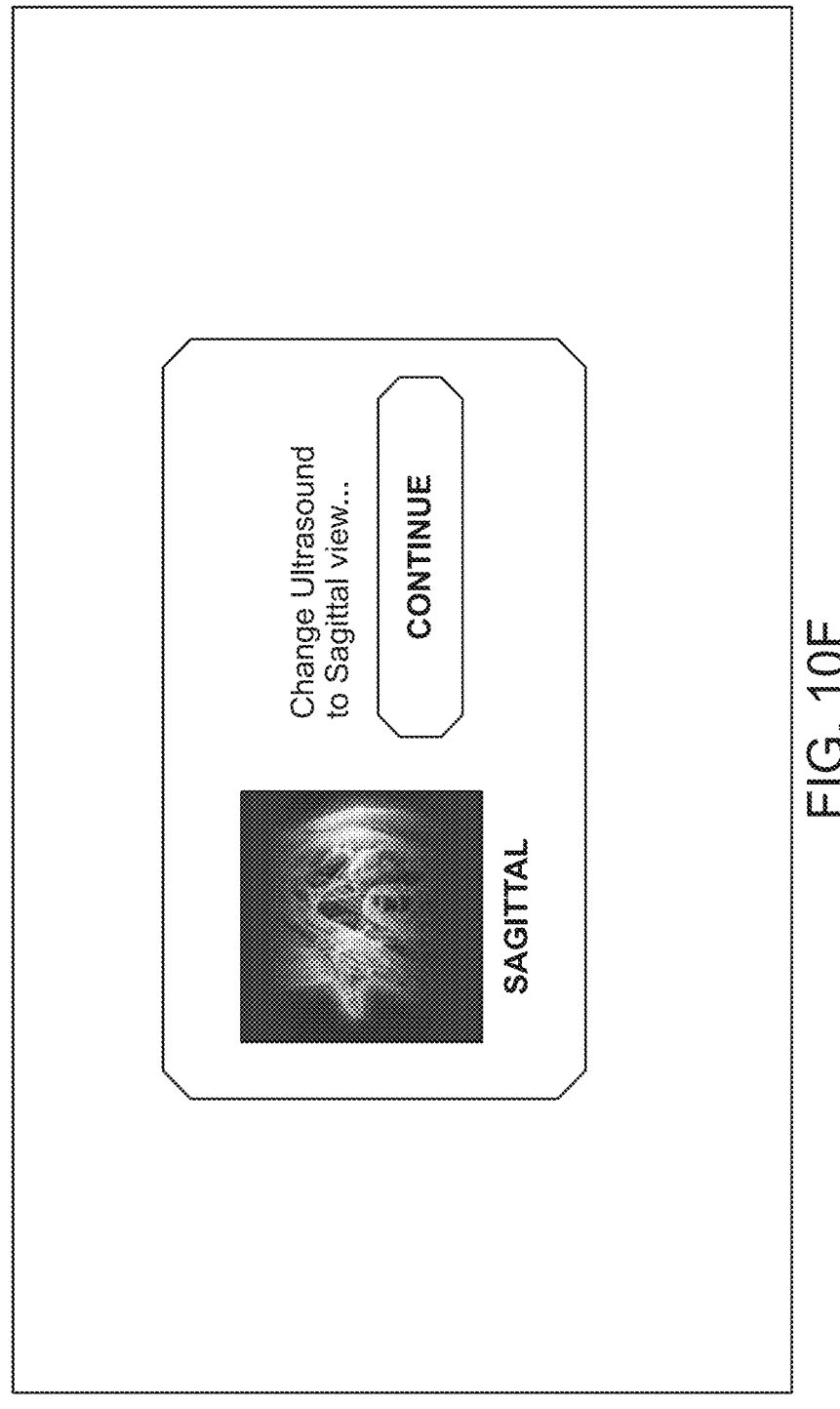

FIG. 10F shows a prompt for the user to change the ultrasound to a sagittal view. Upon changing the ultrasound to the sagittal view, the user can hit the continue button with an input device such as a mouse or touch screen display. The input shown to the user can show an icon showing a sagittal ultrasound view to orient the user with respect to the sagittal view.

Figure 10G:
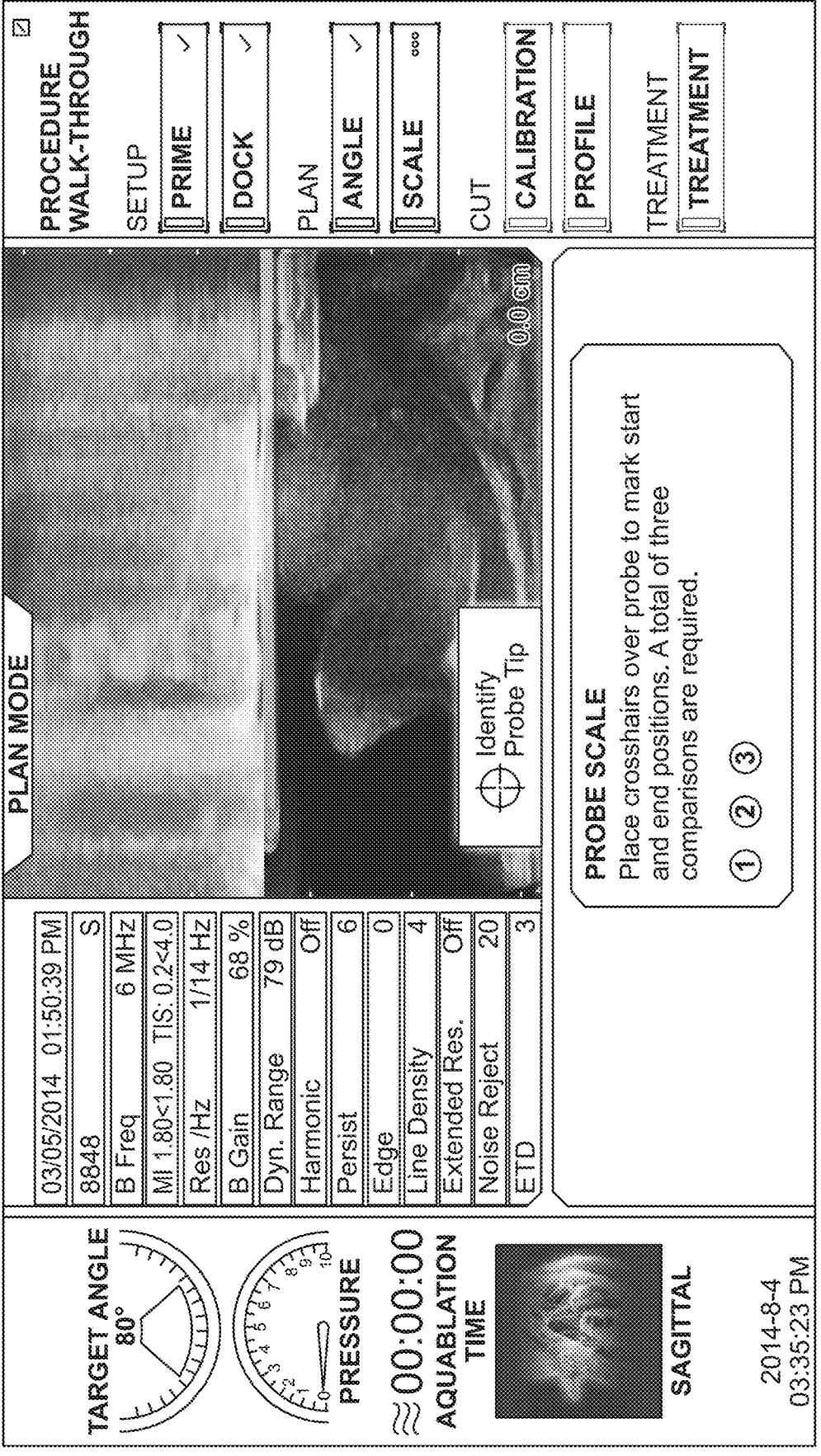

FIG. 10G shows a probe scale user input screen. The probe scaling user input screen can be used to set the scale of the probe in relation to the ultrasound image. The probe can be seen in the upper right hand corner of the sagittal image. The cross hairs can be placed over a movable mark to identify the probe. In many embodiments, the user is prompted to identify the probe tip by placing the cross hair over the probe tip. When the user has placed the cross hair over the probe tip, the instrument receives a command from the input that the probe tip has been identified.

When the probe tip has been identified, the instrument advances the carrier probe to a distal location.

Figure 10H:
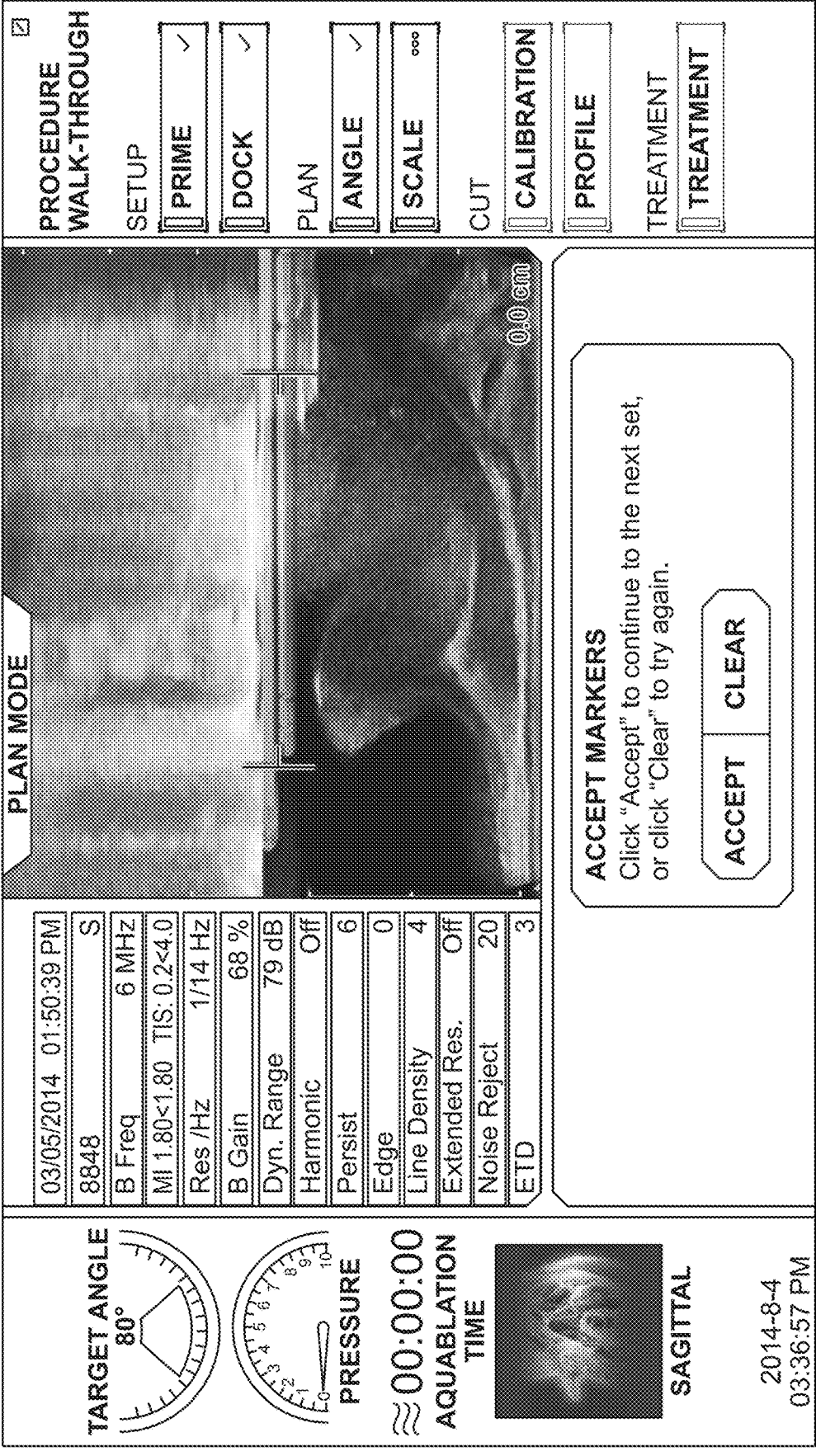

FIG. 10H shows the carrier probe tip advanced to a distal location. The carrier probe tip can be seen with a marker identifying the end of the carrier probe tip. The user can be prompted to identify the carrier probe tip in the second configuration. As shown in FIG. 10H, the first position of the carrier probe tip which is a proximal location as shown with a marker, and the second location of the carrier probe tip which is a distal location as shown with a second marker.

While the carrier can be configured in one or more of many ways to perform the calibration and image guided definition of the treatment as described herein, in many embodiments, a probe comprising a support as described herein is used.

Referring again to FIG. 10G, the probe tip can be seen in a proximal location with the elongate support extending distally a substantial difference. As can be seen in FIG. 10H, the probe tip extends a substantial distance which is closer to the distal end of the elongate support as described herein.

When the user is satisfied with the markers, the user can hit an accept input in order to accept the marks. If the user is not happy with the marks shown in the image, the user can hit the clear button to repeat the step and identify proper marks on the probe in the first and second positions.

Figure 10I:
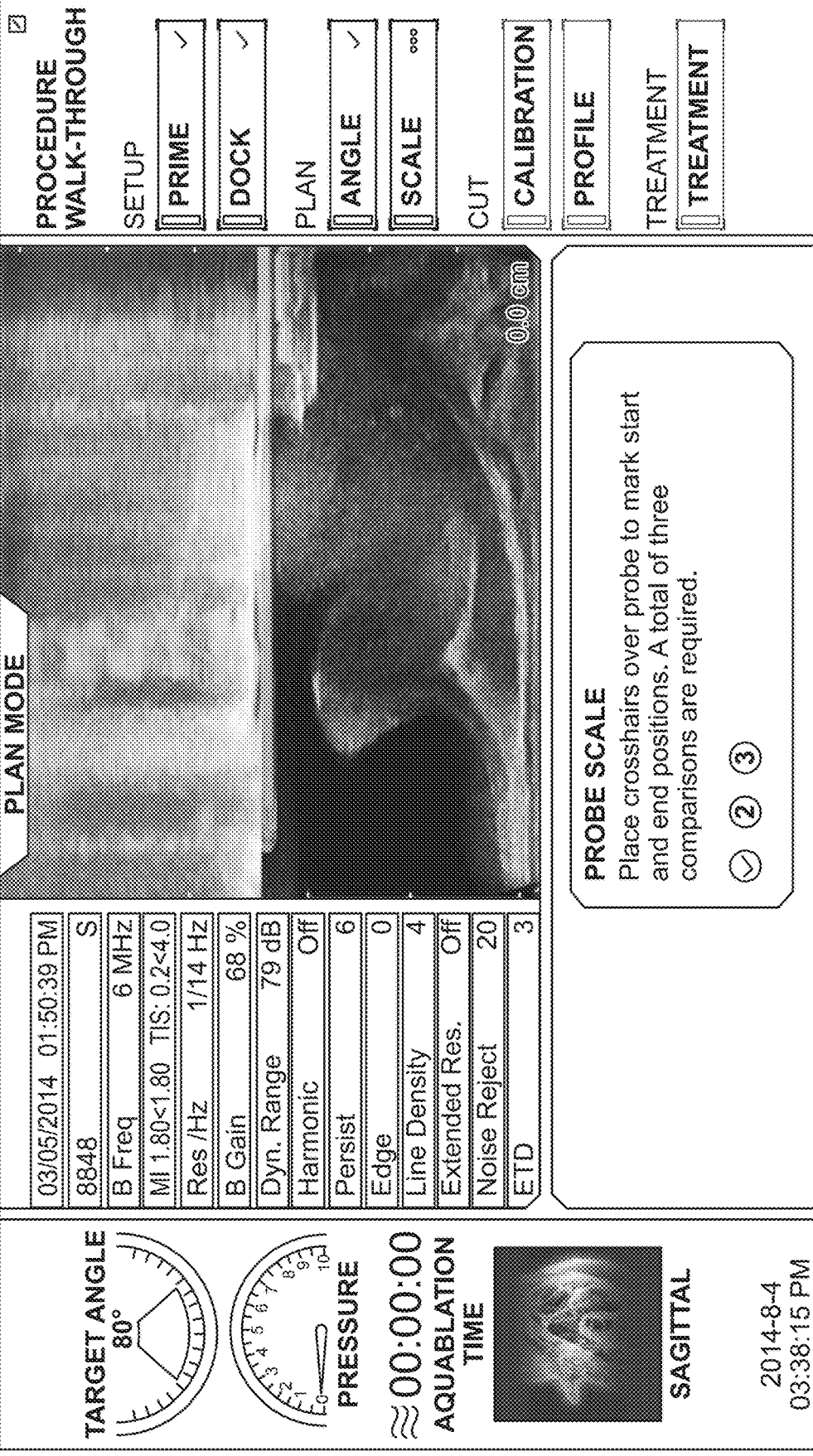

As shown in FIG. 10I, the calibration of the probe is repeated. The user input screen shows a probe scale icon which is used to identify the scaling on the probe, and the user again places the cross hairs over the probe to mark the start and end positions. A total of three comparisons may be required in accordance with some embodiments. Upon successful completion of setting the probe scale for a plurality of times, the scale can be calculated.

Figure 10J:
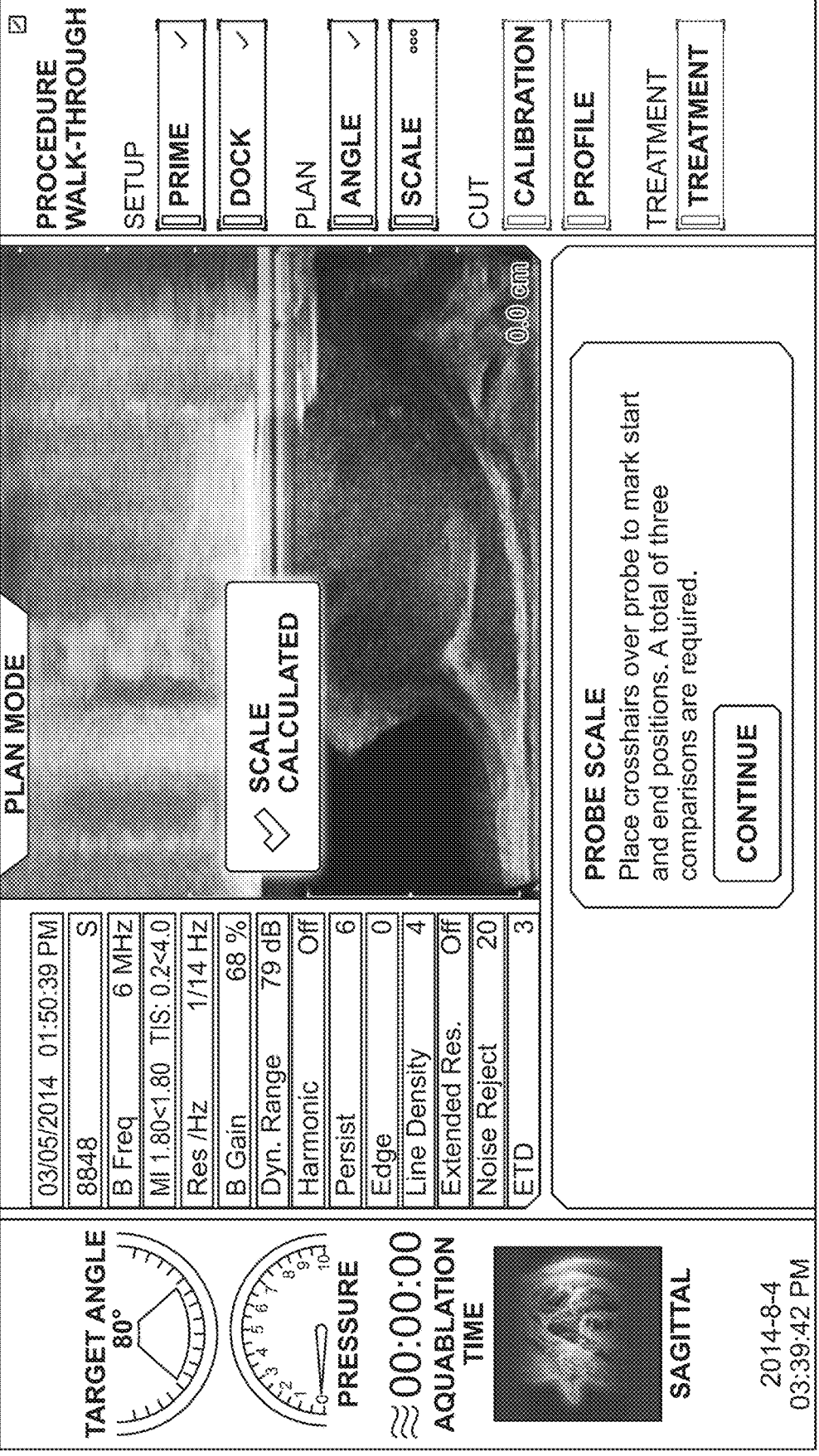

FIG. 10J shows a user input screen in which the user is informed that the scale has been calculated. The user is then prompted to hit a continue button to advance to the next screen.

Figure 10K:
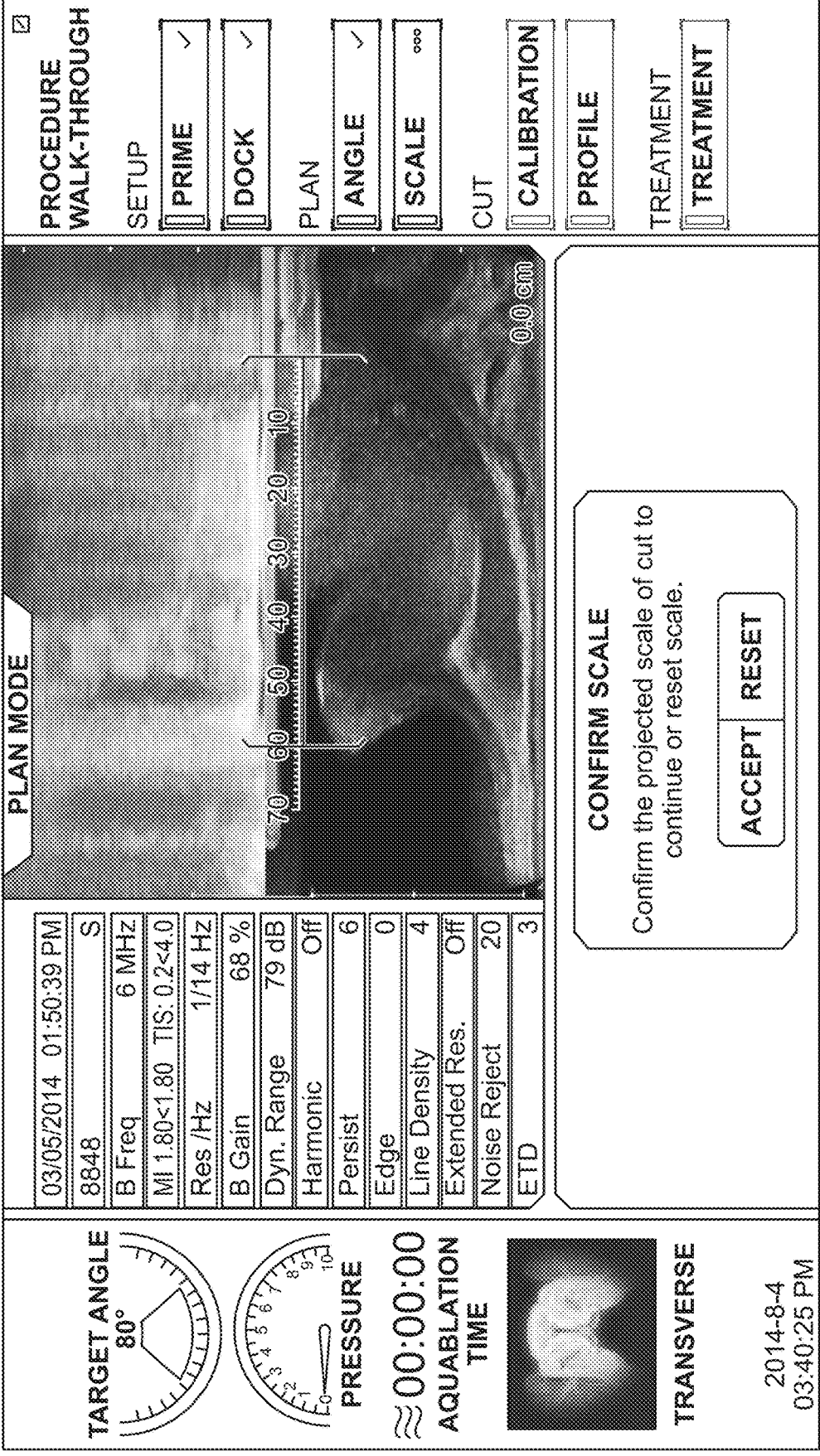

FIG. 10K shows the screen shown on the display in order to confirm the scale. A radical can be shown overlaid on the ultrasound image with the scale determined with the calibration. For example, as shown in FIG. 10K, the scale can extend a distance of 70 millimeters. A calibration and the marks used can also be shown with the radical shown on the display. For example, the proximal mark and the distal mark can be shown on the display. When the distance between the proximal location and the distal location comprises about 60 millimeters, the display can show the marks at a zero location and a 60 millimeter location for example. The radical shown on the ultrasound image is presented to the user, and the user has the opportunity to accept or reset the scale. If the user chooses to reset the scale, the user is prompted to set the scale again. If the user accepts and confirms the scale, the user is allowed to advance to the next screen.

Figure 10L:
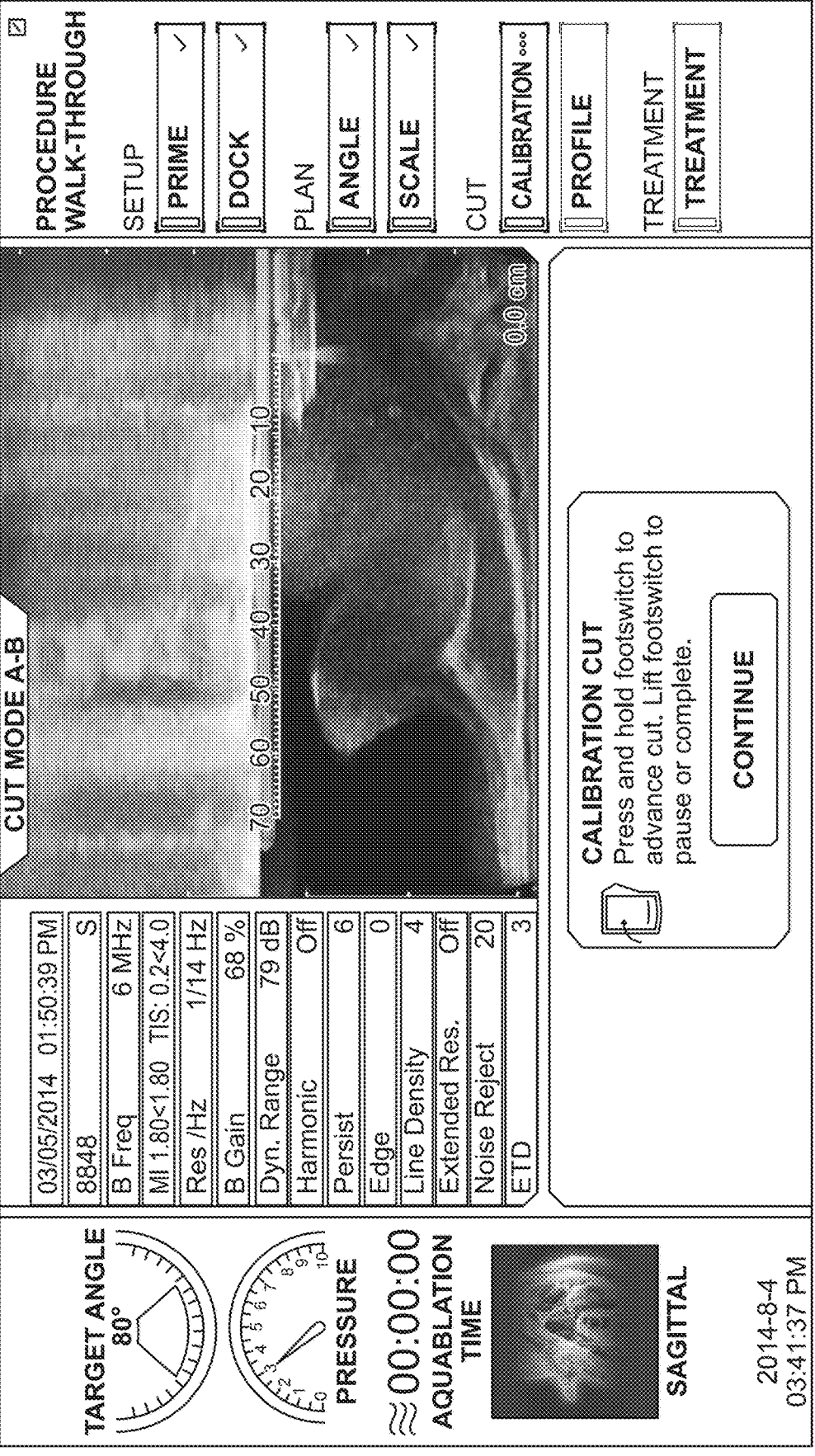

FIG. 10L shows a screen showing a calibration cut in accordance with embodiments. The calibration cut can be performed in order to verify accurate calibration of the system with an initial treatment prior to completing the treatment. The display screen shows a prompt to the user with instructions. The user is prompted to perform the calibration cut. The user can be informed to press and hold the foot switch to advance the cut and to lift the foot switch to pause or to complete the treatment. As shown in FIG. 10L, a radical is shown overlaid with the treatment probe. The treatment carrier probe comprising the nozzle can be initially aligned at a zero reference, for example, over the veramontanum as described herein. The jet can be released from the nozzle and the jet can be visualized with ultrasound as described herein or other imaging modalities, such as the endoscope for example.

Figure 10M:
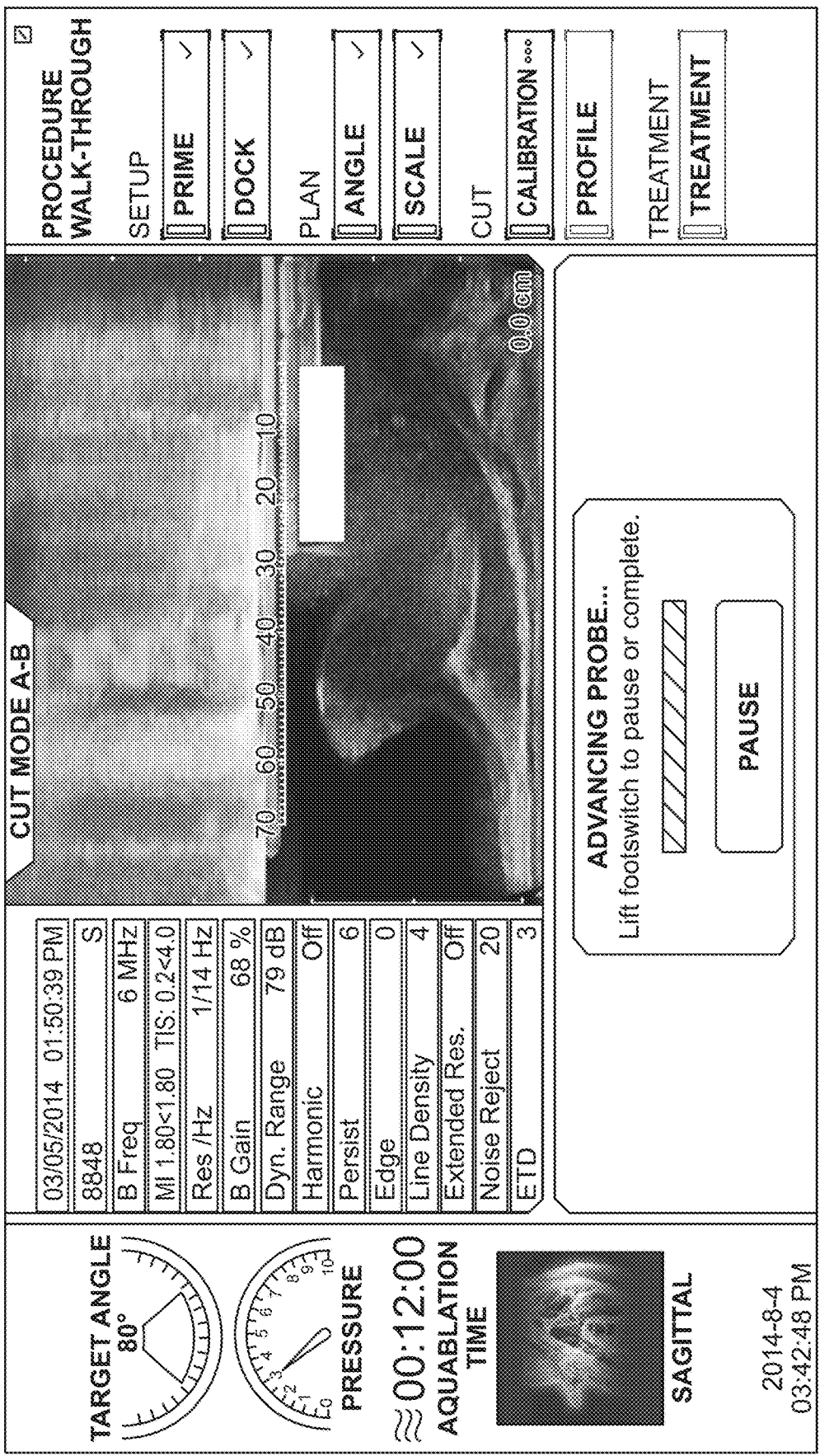

FIG. 10M shows a calibration cut advancing in accordance with embodiments. FIG. 10M shows the image of the calibration cut in real time on the screen. The probe is automatically advanced and the user is instructed to lift the foot switch to pause or to complete the treatment, and a display window indicates that the probe is advancing. The probe can advance in accordance with the treatment profile programmed into the apparatus as described herein. The cut can be shown to extend approximately half way through the treatment for example with reference to Figure TOM, although the real images shown in real time with the user can be provided in relation to the scale. The image of the organ such as the prostate being resected as shown in Figure TOM can help the user determine that the system is accurately set to complete the treatment with tissues that are initially less sensitive to variability in treatment.

Figure 10N:
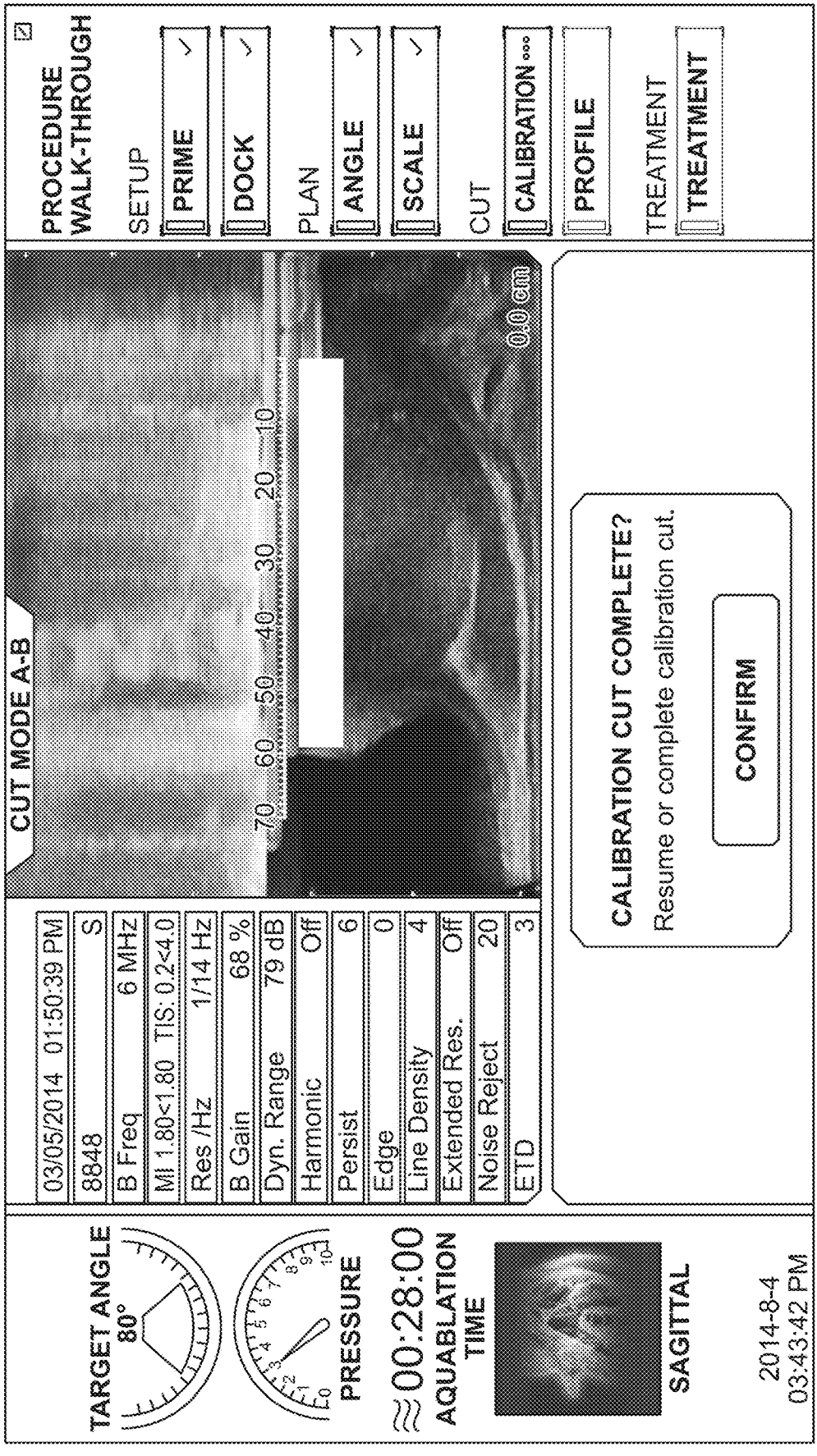

FIG. 10N shows the calibration cut near a distal end of the cut. As shown on the ultrasound image, the jet comprising the cool flame has advanced to a position of approximately 60 millimeters from the zero reference point. As shown in the real time image, the tissue is substantially resected with the target calibration cut. The screen provides the user with an input to confirm the treatment, and the user can indicate the calibration cut is complete by hitting the confirm button. The user is prompted to resume or complete the calibration cut. When the user confirms that the calibration cut is complete, the user is then provided with the next input screen.

Figure 10O:
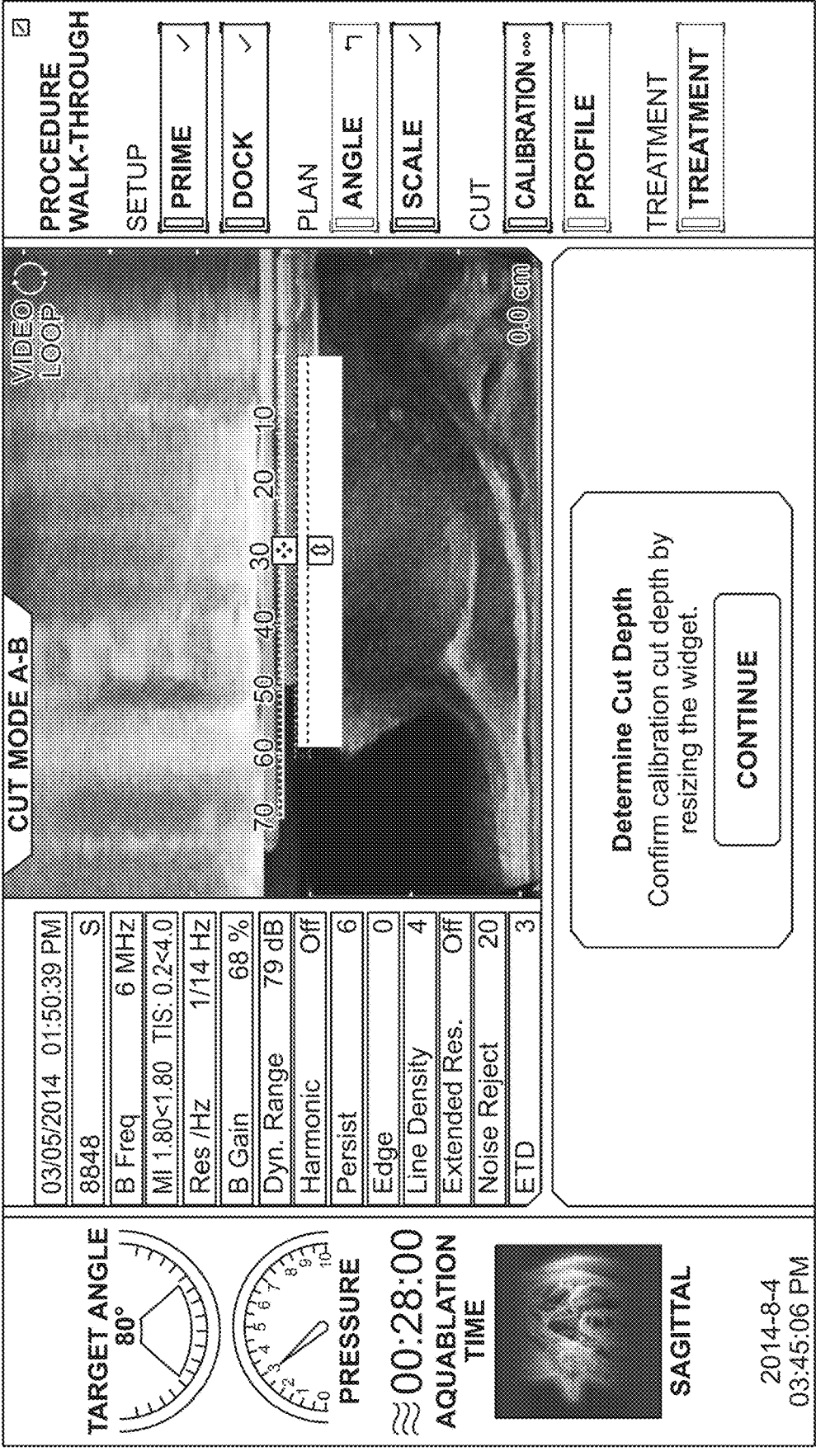

FIG. 10O shows a determine cut depth user interface screen, in accordance with embodiments. The determine cut depth input of the user interface shown on the display allows the user to set the cut depth. As the scaling of the ultrasound image to the treatment probe has been performed previously, the pixel coordinate references of the image can be used to set additional references, such as coordinate references of the treatment profile. The user is prompted with a plurality of lines in order to indicate the cut depth. A first icon showing a vertical arrow in which a first vertical arrow is pointing up and a second vertical arrow is pointing down, the user is allowed to slide an image overlay onto the cut profile to allow the user to approximately estimate the depth of the calibration cut. The user may also be provided with another input screen that allows the user to further adjust the calibration cut measurement. Once the user has confirmed the cut depth, the user is prompted to proceed to the next user input screen. In many embodiments, the system comprises a plurality of thresholds to determine if the calibration cut depth is within appropriate machine boundaries. For example, too shallow of a cut can prompt a warning to the user and too deep of a cut can prompt a similar warning to the user.

The user interface screen may comprise several values that are available to the user. For example, a pressure and a time can be shown to the user along with a target angle. A user may also be shown with the steps of a procedure to complete the procedure, such as setup steps such as priming the pump and docking as described herein. Planning can include an angle and a scale, and the cut can comprise the calibration cut and a profile and the treatment can comprise a treatment profile for example.

Figure 10P:
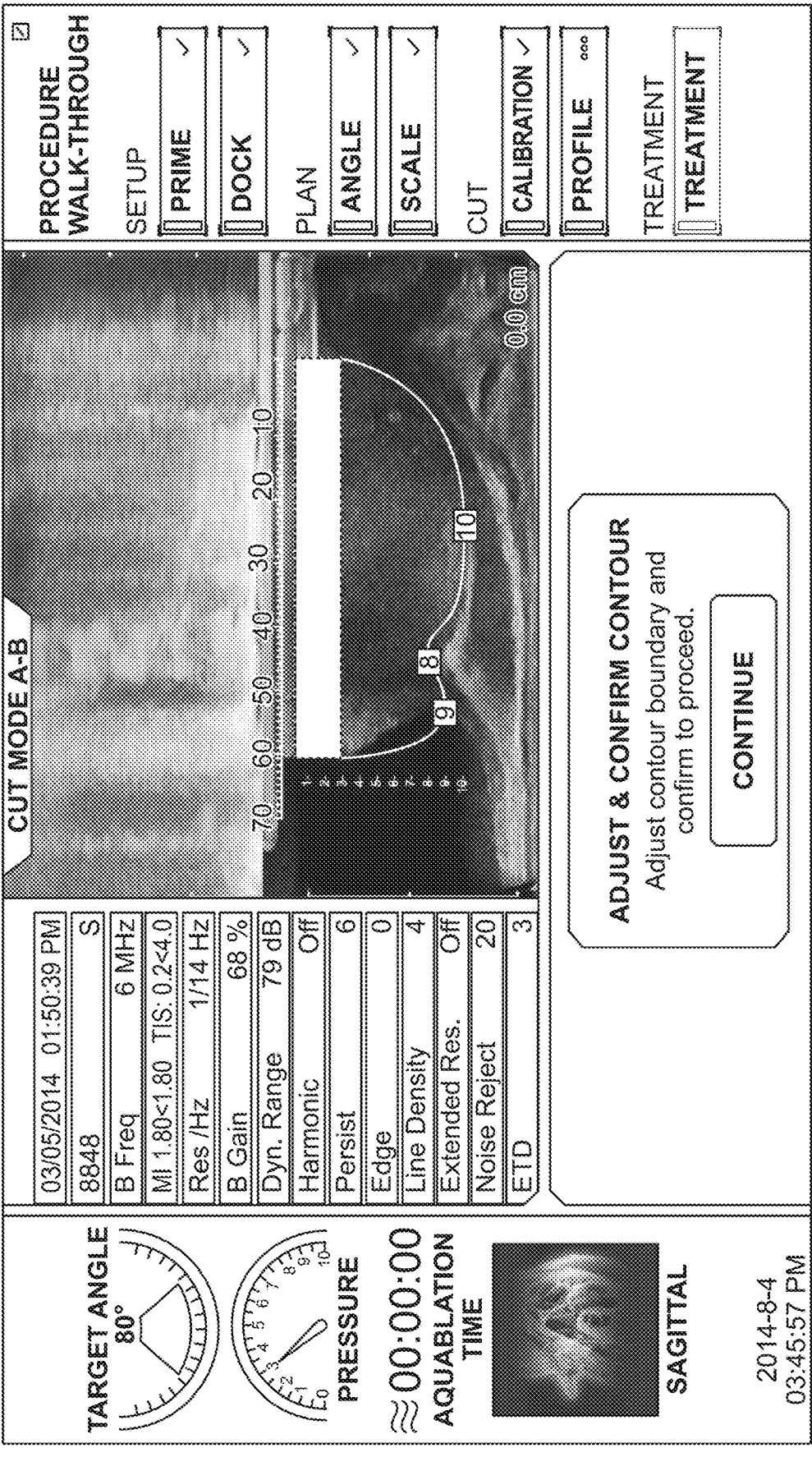

FIG. 10P shows an adjustable profile in accordance with embodiments. FIG. 10P shows a treatment profile shaped to the anatomy of the user. With the ultrasound image of the prostate or other organ shown to the user, the user can select a plurality of locations to adjust the treatment. For example, as shown in FIG. 10P, the treated organ may comprise an enlarged prostate. The enlarged prostate may extend beyond a bladder neck for example or into the bladder neck as indicated with the numeral 9. The narrow restriction of the bladder neck shown at FIG. 8 can be adjusted according to the anatomy of the user and the measurement profile. And FIG. 10 can show, for example, anatomy of the prostate near the capsule and the user can adjust the cut profile accordingly. The user is allowed to adjust and confirm the contour. The user is provided with an adjust and confirm contour menu and instruction. The user is told to adjust the contour boundary and confirm to proceed. When the user has confirmed the treatment profile shown on the ultrasound image, the user hits the continue button in order to proceed.

Figure 10Q:
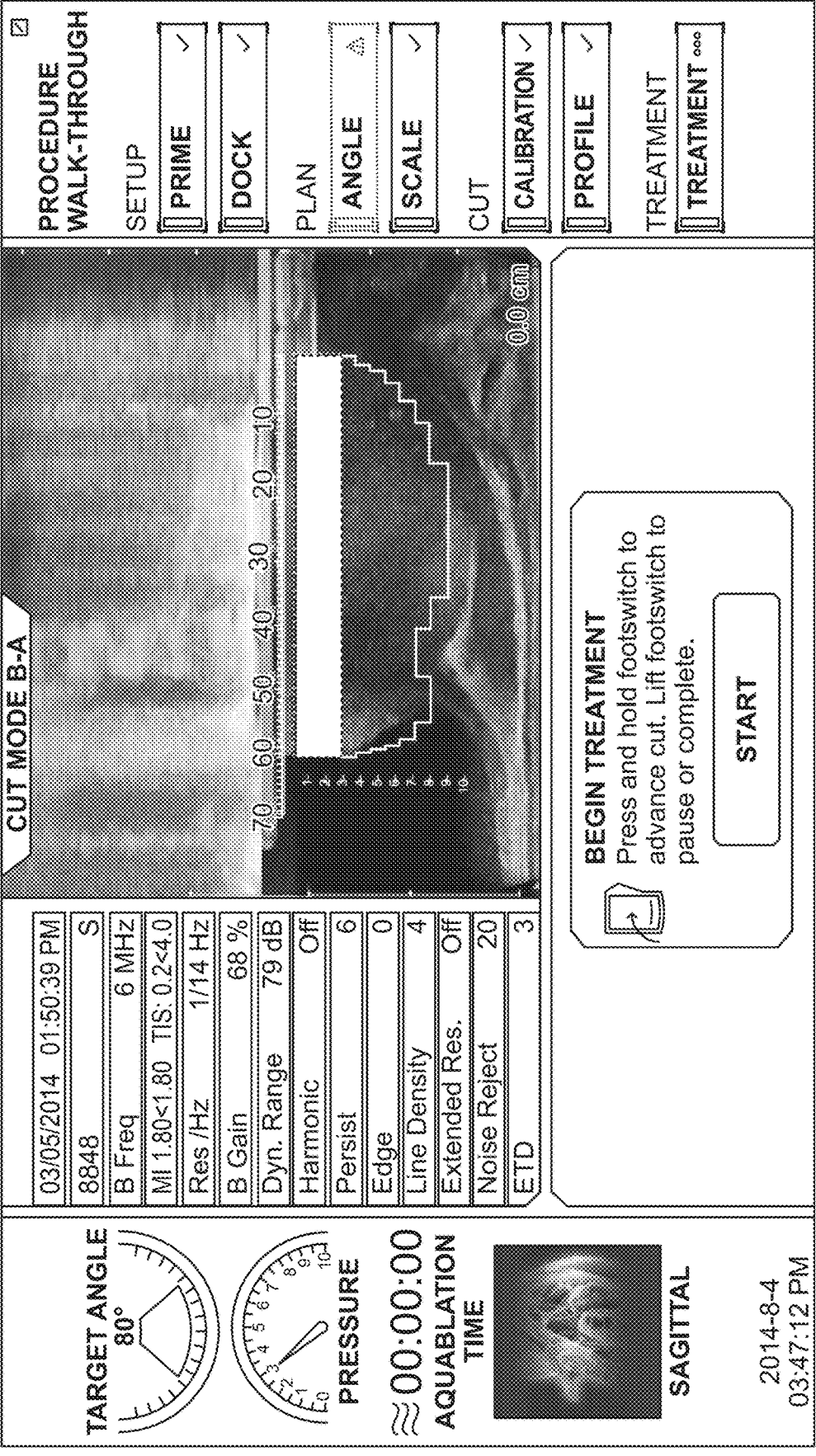

FIG. 10Q shows a begin treatment screen. The begin treatment screen allows the user to begin the treatment. The user is instructed to hit start in order to start the treatment, and the user is instructed to press and hold the foot switch to advance the cut. Lifting this foot switch can pause the treatment. Alternatively, the user can complete the treatment. The cut profile which is fit based on the profile provided by the user is shown to the user. The target cut profile can comprise an approximation of the intended profile provided by the user. While the cut profile of the flame can be configured in many ways, in many embodiments the power of the jet can be increased so that the distance of the white flame and the cavitation as described herein can extend to a desired target distance.

Working relation to embodiments as indicated that a flow rate of the jet can provide a radial cut distance that can be substantially, linearly related to the flow rate of the fluid going into the jet. In many embodiments, the surgical site is irrigated with saline and a fluid stream comprising saline is released with high pressure to form a plurality of shedding pulses as described herein. As the distance of the white cool flame is substantially related to the cutting distance, the user can be provided with visual input as to the cut depth profile. As the cut depth profile changes, the flow rate of the fluid from the jet can be changed so as to correspond to the cut depth profile.

The cut depth profile shown in FIG. 10Q comprising steps may correspond to steps of varying flow rate. For example, the flow rate can be set with arbitrary integer values from 0 to 10 and a calibration cut performed with a flow rate of 3 on the arbitrary scale. Based on the user's anatomy and the cut profile, the system software can determine that a flow rate of 9 is appropriate for the deepest cut, and a flow rate of 8 can be performed near the bladder neck, for example. Near the proximal and distal ends of the cut, the flow rate can increase, for example, from a value of about 3 near the distal end of the cut to a value of about 8 corresponding to tissue in the bladder neck. And the flow rate can decrease, for example, to about 3. As the treatment probe comprising the jet is drawn proximally, the power of the pump can decrease corresponding to the cut profile. For example, the flow rate of the pump in arbitrary units can be decreased from about 8 to a value of about 3 near the proximal end of the cut.

Figure 10R:
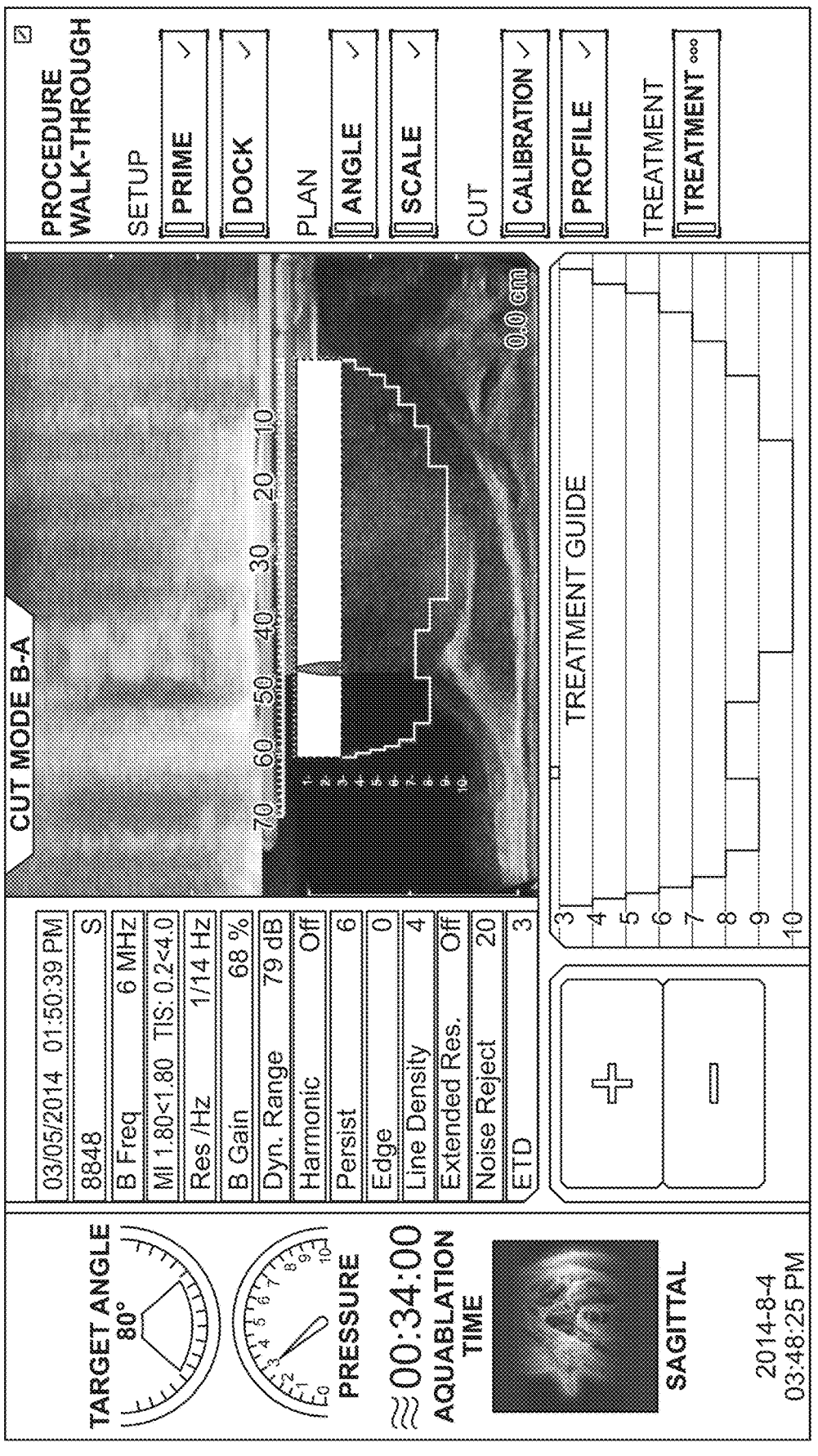

FIG. 10R shows the treatment proceeding with the treatment nozzle carried on the probe being drawn proximally. The drawing of the energy source on the carrier probe proximally can reset tissue as shown in FIG. 10R and other figures. The treatment probe continues to be drawn proximally with rotation and oscillation of the probe tip until a pre-determined volume of tissue has been removed. This removal of the pre-determined volume of tissue in accordance with the cut profile can provide very accurate tissue removal. In many embodiments, delicate structures of the prostate, such as the capsule and nerves can be avoided, for example. In many embodiments, the screen that the user sees can comprise additional screens that may be helpful. For example, a treatment guide window can be provided that shows the position of the energy source on the carrier in relation to the axis of the treatment. The elongated axis of the treatment can extend, based on the program for example, from about 0 to 6 millimeters. As the energy source is drawn proximally, an indicator can be shown on the screen showing the current location of the treatment. This indicator shown on the screen can and should, in many embodiments, correspond to the indicator on the hand piece as described herein. This redundant information allows the user to verify that the instrument is performing correctly.

As described and shown herein, the user can be shown a series of steps that have been completed on the screen, for example, on the right hand side. For example, the user can be shown the current step as the treatment and the user can also be shown several preceding steps. The preceding steps may comprise setup steps, such as priming and docking as described herein. The preceding steps may comprise planning, such as setting the angle and the scale as described herein. And the previous steps may comprise defining the cut profile or parameters related to cutting, such as calibration and definition of the cut profile.

Figure 10S:
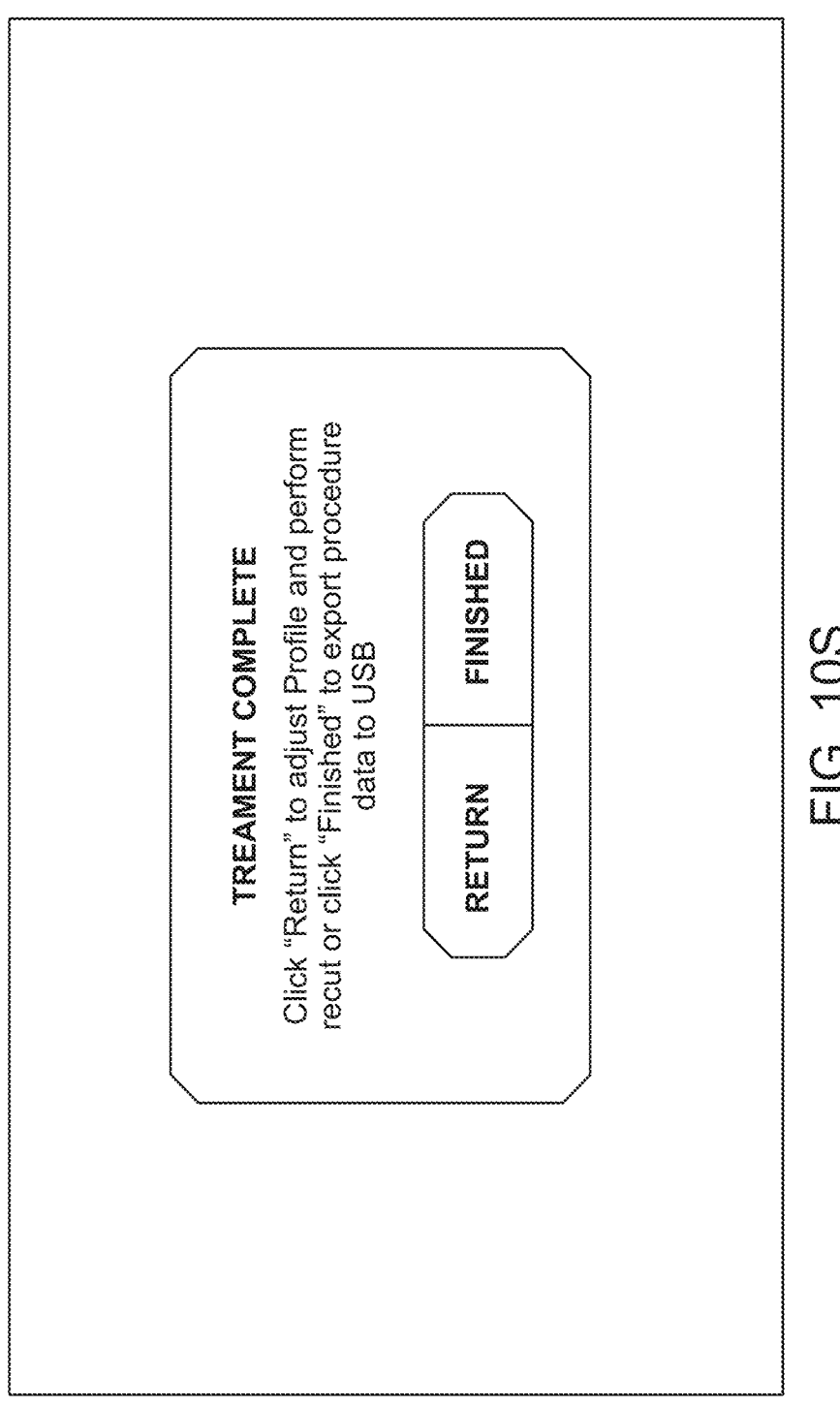
Figure 10T:
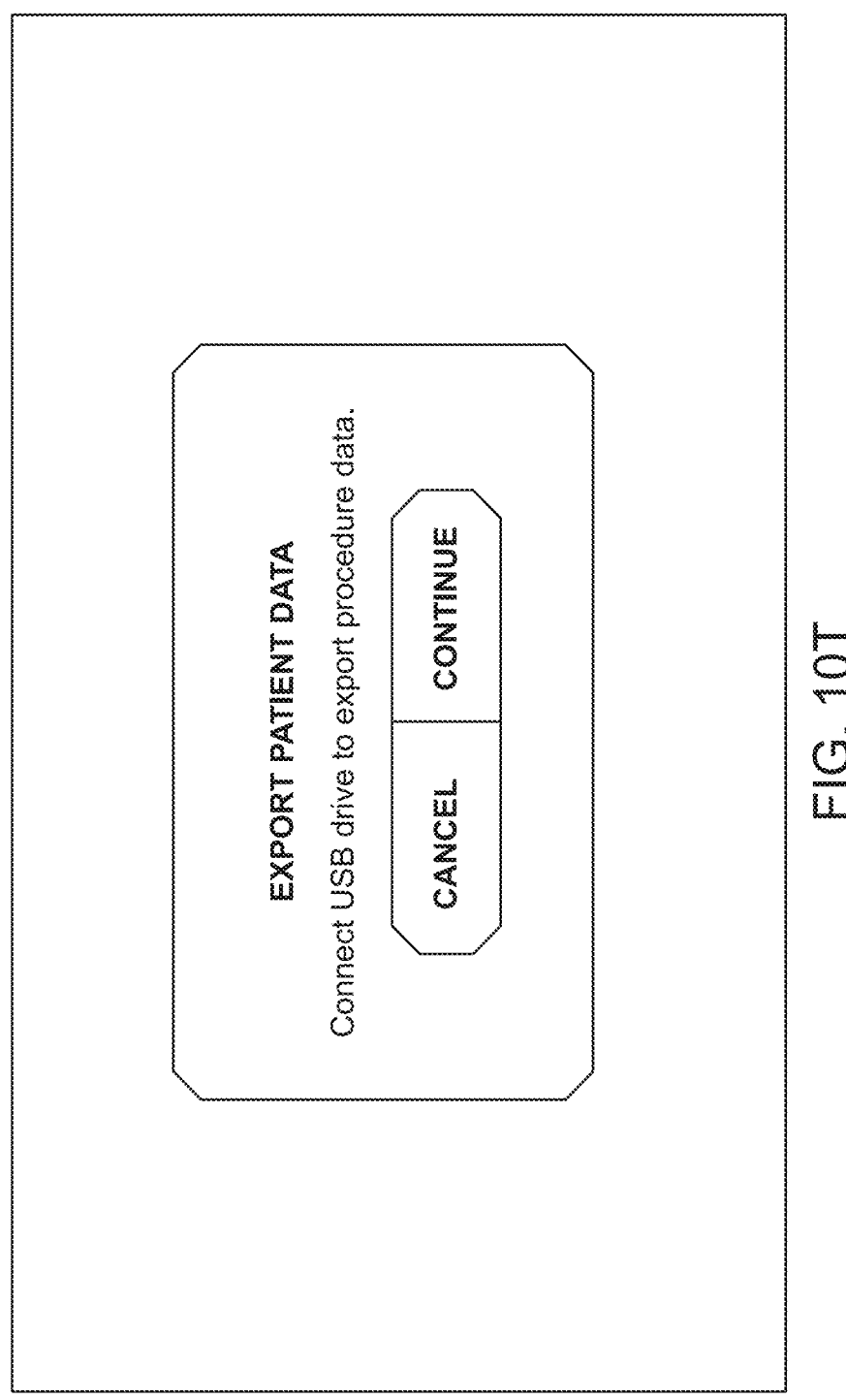

FIG. 10S shows a treatment complete screen. Upon completion of the pre-programmed treatment, the user is presented with the treatment complete screen, and the user has the option of returning to adjust the profile and perform additional resection of tissue, or to input finished and move to the next screen FIG. 10T show shows an export data screen. The user is prompted to export data. The processor may comprise instruction to export the procedure data to a non-volatile memory.

The treatment can be stored in one or more of many ways. For example, the treatment can be stored on a non-volatile memory, such as a flash drive. Alternatively or in combination, the attachment device as described herein may comprise a non-volatile memory to store the treatment. The treatment parameters stored may comprise measured sense parameters, such as the pressure of the treatment, a flow rate of the treatment, and locations of the probe during the treatment. The stored treatment parameters may also comprise a treatment table for example. And the treatment table can provide useful information. For example, when compared to the measured locations of the probe during the treatment in order to verify that the treatment has been performed in accordance with the treatment table. When the user hits the next screen, the user is prompted to move on to the next stage.

The user interface screens of FIGS. 10A to 10T are shown as an example of a series of screens in accordance with embodiments. A person of ordinary skill in the art will recognize many variations based on the teachings provided herein. For example some of the screens can be removed. Other screens can be added. Some of the screens can be combined. Some of the screens may comprise subs-screens. Further the screens may be presented in a different order.

In many embodiments, other alignment screens can be provided. For example, the user can be asked to identify an axis of the treatment probe in order to identify a reference axis of the treatment. The user could be asked to identify marks of the treatment probe, for example, in order to determine translational alignment of the treatment probe axis shown on the image with the mapped treatment shown on the screen.

FIG. 11 shows a method 1100 of treating a patient in accordance with many embodiments.

With a step 1102, an imaging probe is provided having an imaging probe axis.

With a step 1104, a treatment probe is provided having a treatment probe axis.

With a step 1106, an imaging probe axis is aligned with treatment probe axis.

With a step 1110, alignment of treatment probe axis along sagittal plane of imaging probe is verified.

With a step 1112, residual errors are corrected.

With a step 1114 an angle of the treatment probe axis relative to the imaging probe with the imaging probe is measured.

With a step 1116 an image of the patient with the probe inserted therein is rotated in response to the angle With a step 1152, the user interface may query the user if the priming of the treatment probe has been completed.

With a step 1154, the user interface may await the docking of the treatment probe with the computer operating the user interface.

With a step 1156, the user interface may confirm with the user that the ultrasound imaging device is imaging the subject in a transverse view. Upon such confirmation, the main menu screen of the user interface may be shown.

With a step 1158, the user interface may allow the user to select the target angle of the treatment probe when performing the cutting procedure. The target angle may be varied between 0 and 180 degrees.

With a step 1160, the user interface may confirm with the user the selected cutting angle.

With a step 1162, the user interface may confirm with the user that the ultrasound imaging device is imaging the subject in a sagittal view.

With a step 1164, the user interface may facilitate the scaling or calibration of the treatment probe by asking the user to identify the start and end positions of the probe tip as the probe tip is advanced from a retracted position as shown by the ultrasound image. The start and end positions may be identified by the placement of start and end markers, respectively, on the image display portion of the user interface.

With a step 1166, the user interface may confirm with the user the marked start and end positions of the probe tip as acceptable.

With a step 1168, the user interface may repeat the identification and acceptance of start and end positions of the probe tip. In many embodiments, these steps, e.g., steps 1166 and 1168, are repeated three times to verify calibration of the probe tip.

With a step 1170, the user interface may confirm with the user the scaling or calibration of the probe tip.

With a step 1172, the probe tip may perform a calibration cut. The user interface may provide instructions on activating the probe tip to perform the calibration cut. Alternatively or in combination, the user interface may provide a menu or sub-menu to operate the treatment probe to perform the calibration cut. The display portion of the user interface may show the sagittal view of the target tissue as the calibration cut is performed. The treatment probe may be paused and un-paused during the cutting process.

With a step 1174, the user interface may confirm with the user that the calibration cut has been completed.

With a step 1176, the user interface may allow the user to determine and confirm the cut depth of the calibration cut. The user interface may provide markers for the user to drag and place at the cut location and the probe location to confirm cutting depth.

With a step 1178, the user interface may allow the user to adjust and then confirm the contour boundaries of the final cut. The user interface may provide one or more markers for the user to drag and place at desired contour boundary points to modify the contour boundary as desired.

With a step 1180, the treatment probe tip may perform the final cut. The user interface may provide instructions on activating the probe tip to perform the final cut. Alternatively or in combination, the user interface may provide a menu or sub-menu to operate the treatment probe to perform the final cut. The display portion of the user interface may show the sagittal view of the target tissue as the final cut is performed. The treatment probe may be paused and un-paused during the cutting process.

With a step 1182, the treatment may be completed and the user interface may provide an option to repeat and/or modify a treatment and/or export the history, parameters, and other information of the performed treatment to a storage medium, such as a USB drive, a local data storage device, or a cloud-based storage, for example.

The steps of method 1100 can be combined with the screens of FIGS. 10A-10T.

Although the above steps show method 1100 of operating a treatment probe in accordance with many embodiments, a person of ordinary skill in the art will recognize many variations based on the teaching described herein. The steps may be completed in a different order. Steps may be added or omitted. Some of the steps may comprise sub-steps. Many of the steps may be repeated as often as beneficial to the treatment.

For example, steps associated with the performance of a calibration cut (e.g., corresponding to the screens of FIGS. 10L-10O, and/or steps 1172-1176 of method 1100) may be omitted. If there is sufficient data of system performance to provide an accurate correlation between system power and penetration depth of the resultant cuts, the calibration steps may not be necessary, and the system may be configured to proceed directly to the treatment cut.

One or more steps of the method 1100 may be performed with circuitry as described herein, for example, one or more of a processor or a logic circuitry of the systems described herein. The circuitry may be programmed to provide one or more steps of the method 1100, and the program may comprise program instructions stored on a computer readable memory or programmed steps of the logic circuitry such as with programmable array logic or a field programmable gate array, for example FIG. 11 shows a method in accordance with embodiments. A person of ordinary skill in the art will recognize many variations and adaptations in accordance with the teachings disclosed herein. For example, steps of the method can be removed. Additional steps can be provided. Some of the steps may comprise sub-steps. Some of the steps can be repeated. The order of the steps can be changed.

The processor as described herein can be configured to perform one or more of the steps of the method of FIG. 11, and to provide one or more of the user interface screens as described herein. In many embodiments, the processor is configured to perform at least a portion of one or more of the steps in response to user input shown on a display, and the processor may comprise instructions to generate and display the user interface screens as described herein.

The processors can be further configured to record each performed step of the methods described herein with respect to FIGS. 10A-10T and 11. A separate record of use may be kept for each user or operator of the system, wherein all operator inputs provided during each step of the methods can be recorded. The operator records may be configured to be inaccessible for modification by operators (e.g., recorded as read-only files, stored in a restricted access database, backed up to a remote server, etc.). Recordation of all operators inputs and steps performed can provide enhanced operator accountability, and provide useful reference data for system improvements and/or troubleshooting.

EXPERIMENTAL

Figure 12:
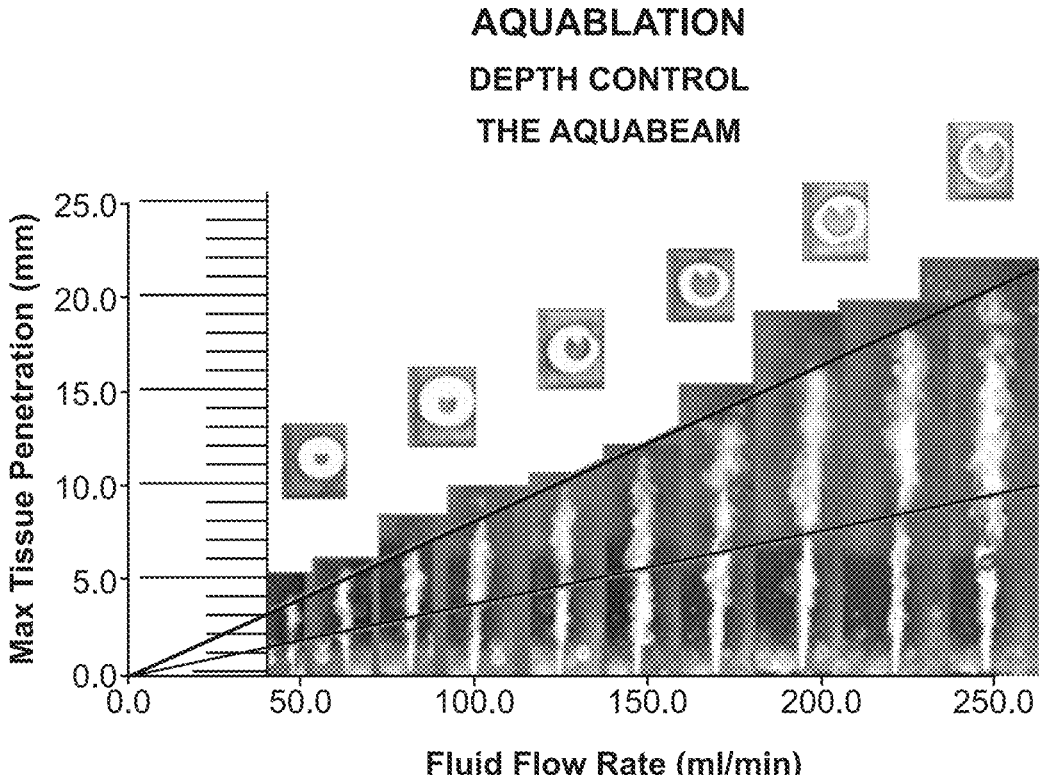
FIG. 12 shows maximum tissue penetration depth of cutting and flow rate through a nozzle in accordance with embodiments.

FIG. 12 shows maximum tissue penetration depth of cutting and flow rate through a nozzle in accordance with embodiments. The maximum penetration depth corresponds substantially to the length of the cavitation bubbles of the jet comprising the "cold" aquablation flame. The maximum tissue penetration depth of ablation corresponds directly to the flow rate and in many embodiments is linearly related to the flow rate.

The inset of FIG. 12 shows cut potato as a model of prostate BPH, in accordance with embodiments. The maximum penetration depth of potato corresponds closely to the maximum cut depth of BPH. The potato is shown cut with 10 different flow settings corresponding to rates within a range from about 50 ml/min to about 250 ml/min with a nozzle and rotating probe as described herein. The maximum penetration depth ranges from about 4 mm at 50 ml/min to about 20 mm at about 250 ml/min.

In many embodiments, the cavitation cloud growth and length comprises a function of flow rate, which is proportional to the injection pressure and vice versa, for an appropriately configured nozzle as described herein. As the pressure increases, the maximum erosive radius appears to increase linearly, which is shown as the maximum penetration depth of FIG. 12.

High velocity cavitating jets can be created by using a known high pressure pump to force the water through a nozzle in either a continuous or pulsatile flow. Despite the flow type produced by a pump, the cavitation phenomenon will be pulsatile due to the unsteady nature of vapor cavities and the cavity formation will be pulsatile even in a continuous flow jet as described herein. Without being bound to a particular theory, it is believed that both pulsatile and continuous flow waterjets will result in equivalent amounts of material erosion over a given amount of time. In many embodiments, nozzle geometry is configured to provide the flow dynamics and cavitation process as described herein. In many embodiments, the nozzle is configured to inhibit tight constriction at the waterjet exit, which can be related cavitation can occur inside the nozzle itself. In many embodiments, the sharp corners cause the water to separate from the wall and converge towards the nozzle centerline, further constricting the waterjet pathway while simultaneously reducing frictional effects caused by the nozzle wall. This results in an increased velocity along with the corresponding pressure drop and the vapor cavities formation. Vapor cavity formation will impact the overall flow dynamics as their eventual collapse results in turbulence and can affect erosion depth. A person of ordinary skill in the art can conduct experiments to determine appropriate nozzle geometry and flow rate to provide tissue removal as described herein without undue experimentation.

Aquablation

Submerged waterjet cutting as described herein has the capability to take advantage of the cavitation phenomenon to treat patients with Benign Prostatic Hyperplasia (BPH). The jet removes the excess soft tissue growth seen in BPH through the pressure pulses and microjets caused by collapsed vapor cavities. The waterjet direction can be manipulated by changing the location and orientation of the devices nozzle, either by translating the nozzle along the anterior-posterior direction or by rotating the nozzle up to 180 degrees, for example.

As vapor cavity formation and its erosive strength is a function of both injection pressure and the flow dynamics, the depth of material can be controlled by configuring the pressure as well as nozzle geometry. A greater injection pressure will result in a faster exit velocity. As discussed herein, the nozzle geometry can further increase the velocity depending on the constriction and will affect the degree of pressure drop as the waterjet exits through the Venturi effect. These factors can result in longer distances the cavitation clouds can grow to and travel before collapsing and releasing pressure pulses and microjets. The nozzle geometry and pressure settings of the Aquablation system have been optimized to give the user precise control and ensure the cavitating jet removes only the desired benign tissue growth.

The images provided herein show the how tissue erosion depth is a function of pressure, in accordance with embodiments. The images show the smaller cavitation cloud length and corresponding tissue resection depth for a lower injection pressure as compared with other images.

In many embodiments, Aquablation as described herein is capable of removing the excess tissue growth, e.g. BPH, with inhibited removal and damage of arteries and veins. The pressure pulses and microjets caused by cavitation exceed the threshold energy required to erode the soft tissue growth, and may cause minimal damage to other structures like vessels which have a much higher threshold energy. Repeated and concentrated pressure pulses and microjets may cause fatigue stress on the vasculature and result in bleeding, but the Aquablation system algorithm and treatment instructions as described herein are configured designed to inhibit such damage.

In many embodiments, generation of harmful emboli are inhibited. Vapor cavity formation may benefit from a minute nucleus of air already present in the blood stream, for example. Cavitation can result in the growth of the nucleus without any additional air being introduced into the system. Furthermore, the cavity will collapse once the local jet pressure exceeds the vapor pressure, such that the air pockets may reduce back to their original nucleus size. In many embodiments, embolus formation is inhibited as cavitation depends on and can be limited to micro amounts of air native to the saline solution surrounding the urethra, and the vapor cavities quickly dissipate as the jet pressure begins to rise.

Aquablation as described herein takes advantage of this phenomenon. The naturally self-limiting erosive radius and unique ability to precisely ablate tissue with a low damage threshold energy while minimizing damage to nearby structures with a more dense cellular structure, such as arteries, make Aquablation as described herein a useful surgical tool for treating BPH. Coupled with the nearly isothermal property of cavitation as described herein, which can mitigate collateral damage and provide improved healing and an improved safety profile.

Figure 13:
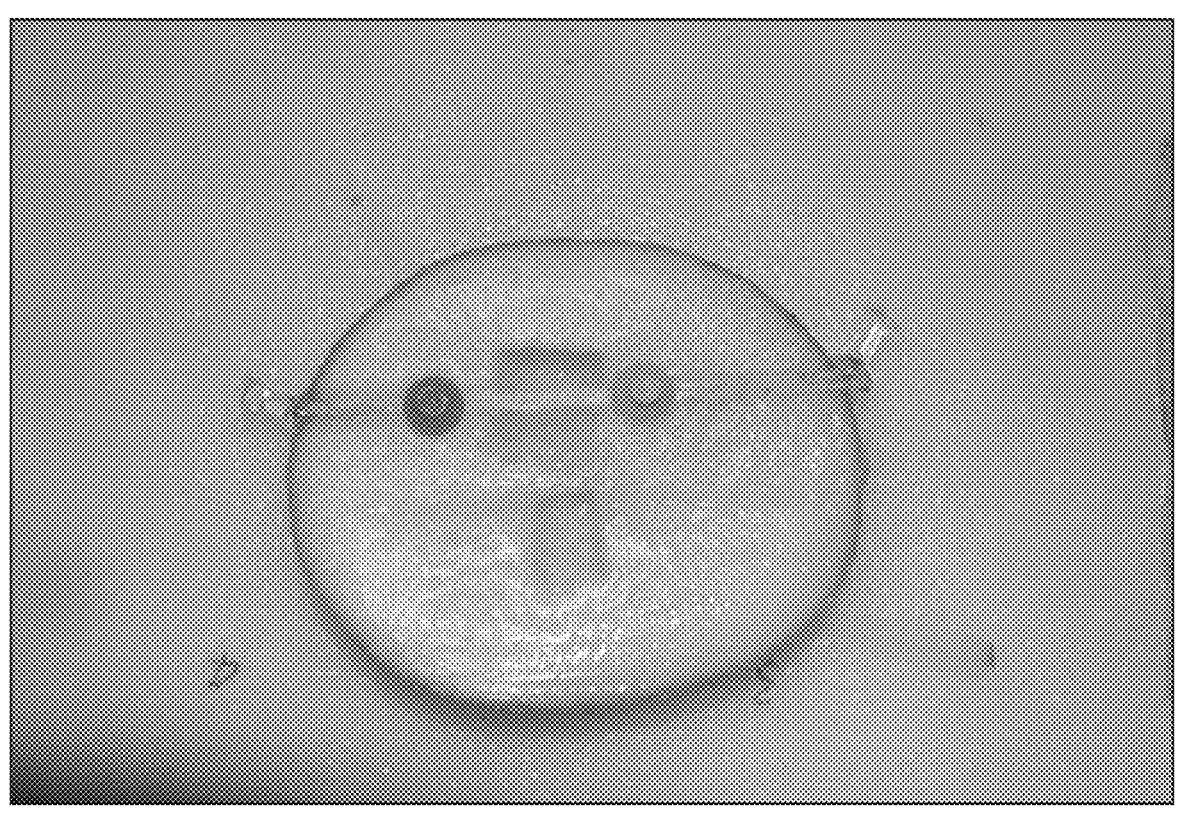
FIG. 13 shows selective removal of potato with a porcine blood vessel positioned over the incision of the potato as a model for selective removal of tissue in accordance with embodiments.

FIG. 13 shows selective removal of potato with a porcine blood vessel positioned over the incision of the potato as a model for selective removal of tissue. The porcine blood vessel was placed on the potato prior to the incision, such that the porcine blood vessel was exposed to the water jet with cavitation in order to remove the potato. Aquablation resected the soft potato tissue model, which is a close proxy for the benign tissue growth seen in BPH, without causing severe damage to the porcine vessel.

Figure 14:
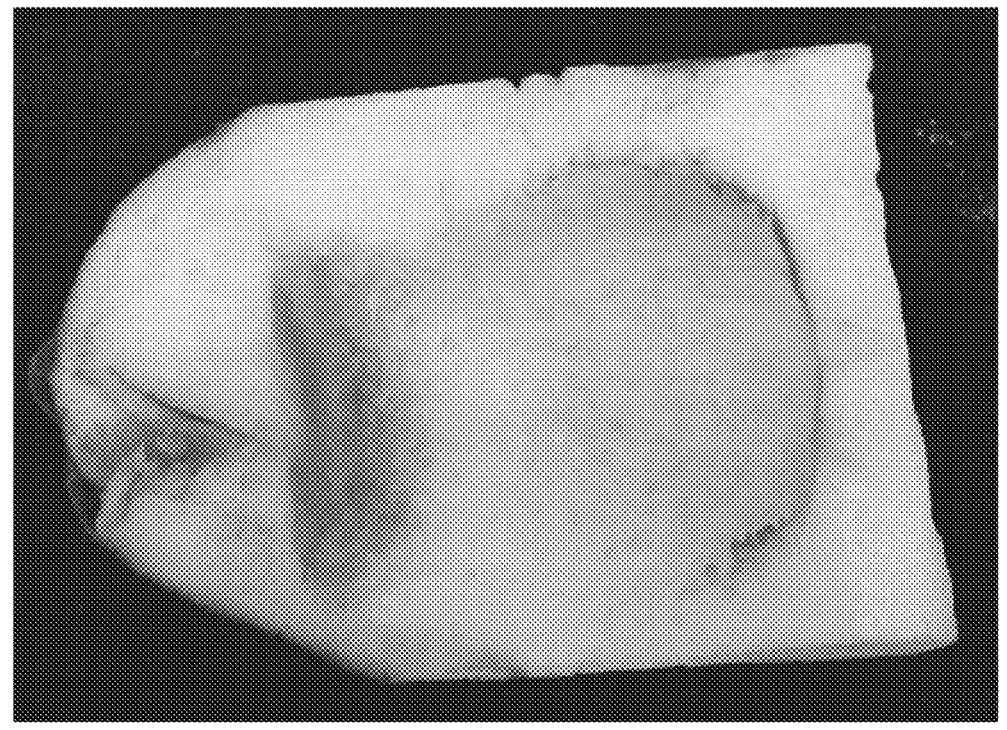
FIG. 14 shows a potato treated with a predetermined treatment profile and treatment table based on user input in accordance with embodiments.

FIG. 14 shows a potato treated with a predetermined treatment profile and treatment table based on user input.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus to treat a patient, comprising:
an elongate support comprising a tip for insertion into the patient;
an elongate carrier tube supported by the elongate support and configured to direct energy to a target site from an energy source affixed to a distal portion of the elongate carrier tube;
a handpiece configured to receive an endoscope and support the elongate carrier tube, the handpiece comprising a first plurality of connectors configured to couple to a second plurality of connectors in order to control rotation and translation of the elongate carrier tube; and
a coupling supported by the elongate support, the coupling comprising:
one or more openings configured to receive the endoscope and the elongate carrier tube; and
a slot configured to engage with the endoscope to lock the endoscope in position,
wherein the coupling is configured to move with the endoscope relative to the elongate carrier tube and the elongate support, the elongate carrier tube is configured to move independently of the endoscope and the coupling, and the tip of the elongate support extends past the coupling.

2. The apparatus of claim 1, further comprising an elongate tube, and wherein the elongate tube has an internal diameter sized to receive the endoscope and the elongate carrier tube and wherein the elongate support extends axially outside the elongate tube and wherein the elongate support extends beyond a distal end of the elongate tube.

3. The apparatus of claim 1, wherein the first plurality of connectors comprise a first rotatable connector to control an angle of rotation of the energy source around a longitudinal axis of the elongate carrier tube and a second rotatable connector to control an axial location of the energy source.

4. The apparatus of claim 3, wherein the energy source comprises a nozzle and the first rotatable connector is configured to control an angle of rotation of the nozzle around the longitudinal axis and the second rotatable connector is configured to control an axial location of the nozzle.

5. The apparatus of claim 4, wherein the second plurality of connectors comprises a plurality of torque transmitters to rotate and translate the elongate carrier tube.

6. The apparatus of claim 1, further comprising an elongate tube, wherein each of the endoscope, the elongate carrier tube and the elongate support are sized for insertion into a patient and wherein the elongate carrier tube and the endoscope are slidably disposed within the elongate tube with the elongate support extending axially outside the elongate tube.

7. The apparatus of claim 1, wherein the elongate support comprises an axially extending aspiration channel extending to at least one aspiration opening oriented perpendicularly to the elongate carrier tube, the at least one aspiration opening configured to receive tissue from the target site.

8. The apparatus of claim 1, wherein the handpiece further comprises an encoder configured to determine an angle of rotation of the energy source around a longitudinal axis of the elongate carrier tube and one or more detectors configured to measure the angle of rotation of the energy source.

9. The apparatus of claim 8, wherein the encoder comprises an optical encoder.

10. The apparatus of claim 8, wherein the encoder provides an absolute angular orientation of the elongate carrier tube in relation to the one or more detectors.

11. The apparatus of claim 8, wherein the encoder comprises an annular structure extending circumferentially around a proximal portion of the elongate carrier tube.

12. The apparatus of claim 1, further comprising a plurality of detectors distributed around the elongate carrier tube at a plurality of fixed angular and radial locations to measure rotation of the elongate carrier tube and wherein the fixed angular locations correspond to an angular orientation of the elongate carrier tube around a longitudinal axis of the elongate carrier tube.

13. The apparatus of claim 1, wherein the handpiece further comprises an input to increase or decrease a power setting of the energy source.

14. The apparatus of claim 1, wherein the handpiece comprises a connector configured to electronically couple to an arm and transmit data to the arm.

15. The apparatus of claim 1, further comprising an arm, wherein the arm comprises one or more of a manually movable arm or a robotic arm.

16. The apparatus of claim 1, further comprising an arm, wherein the handpiece is configured to couple to the arm.

17. The apparatus of claim 1, wherein the energy source is directed transverse to a longitudinal axis of the elongate carrier tube.

18. The apparatus of claim 1, wherein the energy source comprises a nozzle, the nozzle comprising a jewel mounted on the elongate carrier tube.

19. The apparatus of claim 1, wherein the slot is configured to engage with a protrusion on the endoscope.

* * * * *